(12) United States Patent
Ismagilov et al.

(10) Patent No.: US 10,585,091 B2
(45) Date of Patent: Mar. 10, 2020

(54) DIGITAL ASSAY FOR QUANTIFYING AND CONCENTRATING ANALYTES

(71) Applicants: CALIFORNIA INSTITUTE OF TECHNOLOGY, Pasadena, CA (US); UNIVERSITY OF CHICAGO, Chicago, IL (US)

(72) Inventors: Rustem F. Ismagilov, Altadena, CA (US); Stephanie McCalla, Pasadena, CA (US); Travis Schlappi, Pasadena, CA (US); Toan Huynh, Chicago, IL (US); Justin Rolando, Pasadena, CA (US); Weishan Liu, Pasadena, CA (US); Shencheng Ge, Pasadena, CA (US); Jason E. Kreutz, Marysville, WA (US)

(73) Assignees: The University of Chicago, Chicago, IL (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 15/000,864

(22) Filed: Jan. 19, 2016

(65) Prior Publication Data
US 2016/0266105 A1 Sep. 15, 2016

Related U.S. Application Data

(63) Continuation of application No. PCT/US2014/047092, filed on Jul. 17, 2014.
(Continued)

(51) Int. Cl.
*G01N 35/08* (2006.01)
*G01N 33/543* (2006.01)
(Continued)

(52) U.S. Cl.
CPC ...... *G01N 33/54366* (2013.01); *B01L 3/5023* (2013.01); *B01L 3/502715* (2013.01);
(Continued)

(58) Field of Classification Search
CPC ............... G01N 35/08; G01N 21/6428; B01L 3/502784
(Continued)

(56) References Cited

U.S. PATENT DOCUMENTS

| 5,718,509 A | 2/1998 | Dunfee |
| 2002/0055167 A1 | 5/2002 | Pourahmadi et al. |

(Continued)

FOREIGN PATENT DOCUMENTS

| WO | WO 2007/089777 A2 | 8/2007 |
| WO | WO 2009/015390 A2 | 1/2009 |

(Continued)

OTHER PUBLICATIONS

PCT International Search Report and Written Opinion, International Application No. PCT/US2014/047092, dated Nov. 7, 2014, 11 Pages.
(Continued)

*Primary Examiner* — Natalia Levkovich
(74) *Attorney, Agent, or Firm* — Goodwin Procter LLP

(57) ABSTRACT

Provided herein are methods, compositions, and devices for the identification and quantification of analytes, such as nucleic acids, proteins, cells or other biological samples. The methods, compositions, and devices are suited for accurate, portable analysis of small amounts of analyte.

23 Claims, 59 Drawing Sheets

Related U.S. Application Data

(60) Provisional application No. 61/856,155, filed on Jul. 19, 2013, provisional application No. 61/880,399, filed on Sep. 20, 2013, provisional application No. 61/969,008, filed on Mar. 21, 2014.

(51) Int. Cl.
*B01L 3/00* (2006.01)
*C12Q 1/6844* (2018.01)

(52) U.S. Cl.
CPC ... *B01L 3/502738* (2013.01); *B01L 3/502761* (2013.01); *C12Q 1/6844* (2013.01); *G01N 33/54386* (2013.01); *B01L 3/502753* (2013.01); *B01L 2200/0668* (2013.01); *B01L 2200/0673* (2013.01); *B01L 2300/069* (2013.01); *B01L 2300/0627* (2013.01); *B01L 2300/0803* (2013.01); *B01L 2300/0816* (2013.01); *B01L 2300/0819* (2013.01); *B01L 2300/0893* (2013.01); *B01L 2300/12* (2013.01); *B01L 2300/165* (2013.01); *B01L 2400/0644* (2013.01)

(58) Field of Classification Search
USPC .................................. 436/53, 52; 422/82, 93
See application file for complete search history.

(56) References Cited

U.S. PATENT DOCUMENTS

| | | |
|---|---|---|
| 2007/0122819 A1 | 5/2007 | Wu et al. |
| 2010/0221762 A1 | 9/2010 | Sterling et al. |
| 2011/0124130 A1 | 5/2011 | Wagner et al. |
| 2012/0021527 A1 | 1/2012 | Salzer et al. |
| 2012/0028342 A1* | 2/2012 | Ismagilov ......... B01L 3/502738 435/283.1 |
| 2012/0045765 A1* | 2/2012 | Curran ................ B01F 13/0071 435/6.12 |
| 2012/0214707 A1 | 8/2012 | Ymeti et al. |

FOREIGN PATENT DOCUMENTS

| | | |
|---|---|---|
| WO | WO 2009/048673 A2 | 4/2009 |
| WO | WO 2010/111265 | 9/2010 |
| WO | WO 2013/036598 A1 | 3/2013 |

OTHER PUBLICATIONS

PCT International Preliminary Report on Patentability, International Application No. PCT/US2014/047092, dated Jan. 19, 2016, 7 Pages.

Ge, S., et al., "Digital, Ultrasensitive, End-Point Protein Measurements with Large Dynamic Range via Brownian Trapping with Drift," Journal of the American Chemical Society, 2014, pp. 14662-14665, vol. 136, No. 42.

Huynh, T., et al., "Chemical Analog-to-Digital Signal Conversion Based on Robust Threshold Chemistry and Its Evaluation in the Context of Microfluidics-Based Quantitative Assays," Journal of the American Chemical Society, 2013, pp. 14775-14783, vol. 135, No. 39.

Sun, B., "Mechanistic studies of reactions at the single-molecule level using microfluidics with applications in molecular diagnostics," Dissertation (Ph.D.), California Institute of Technology, 2014, 102 Pages, available at <URL:http://resolver.caltech.edu/CaltechTHESIS:05052014-142031176>.

* cited by examiner

- 211 Wicking layer
- 212 Gel Pad layer (slip layer)
- 213 Sample/Reagent Wells 221  222  223

224  225  226

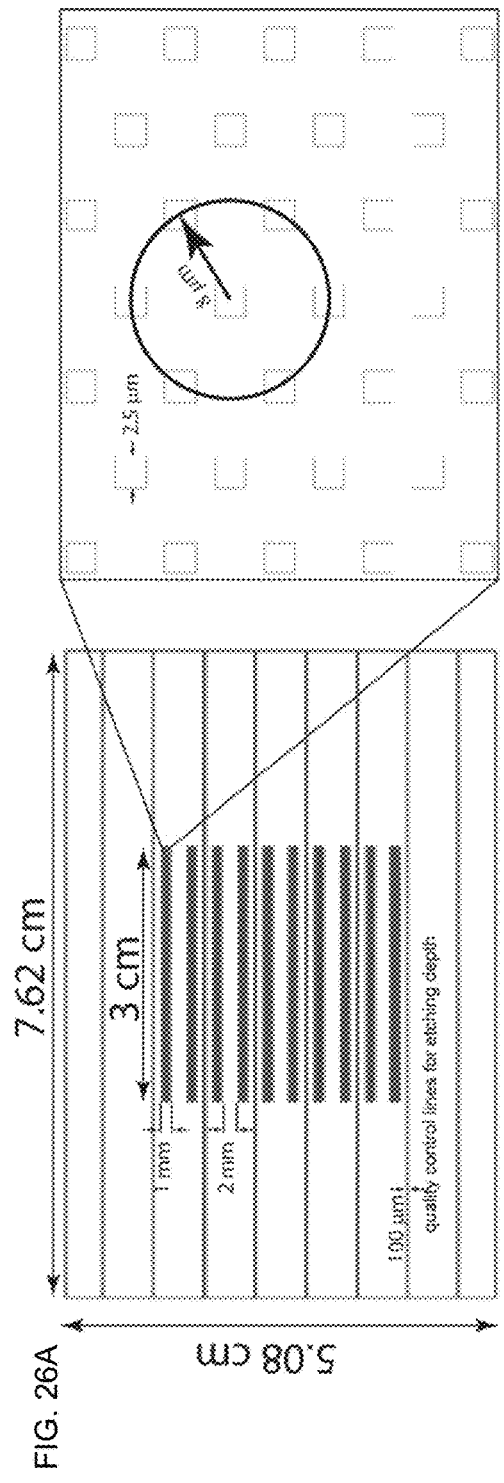
FIG. 26A Photomask for microwells
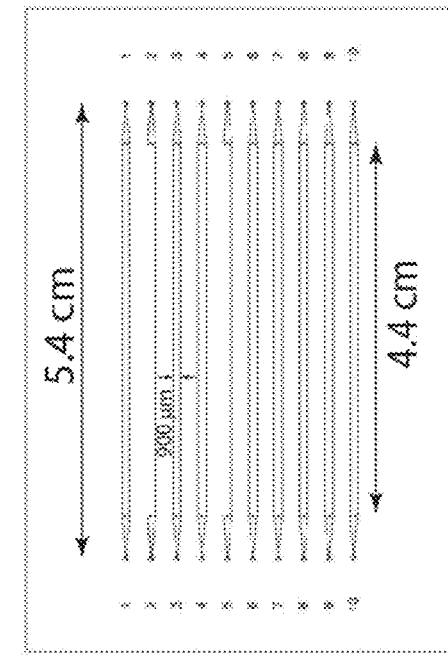
FIG. 26B Photomask for channels FIG. 27A
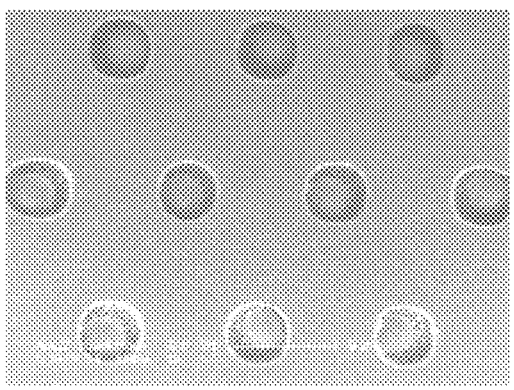
FIG. 27B
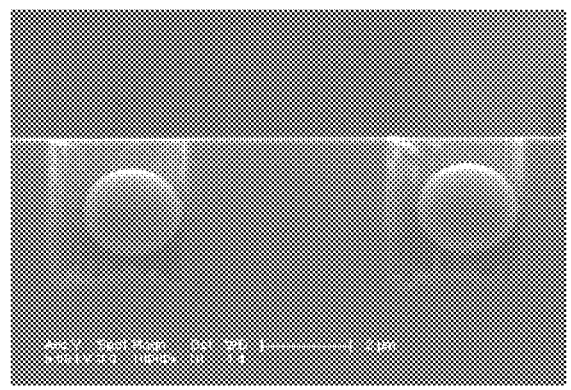
FIG. 27C
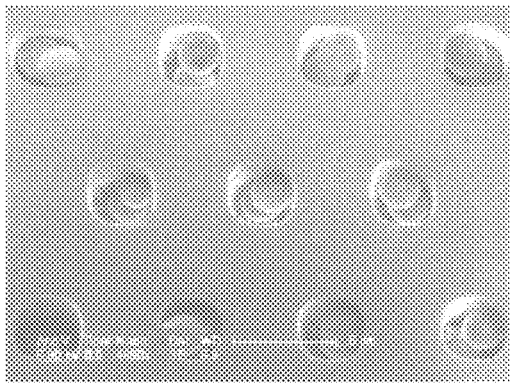
FIG. 27D
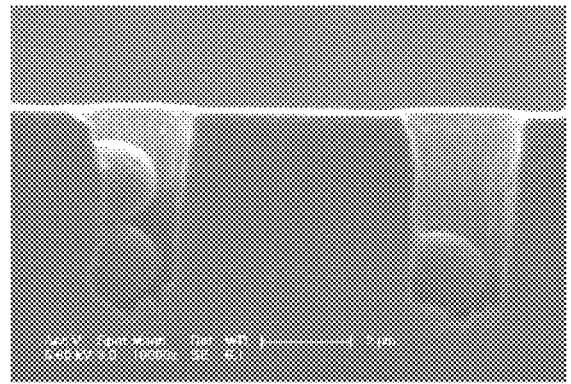
FIG. 27

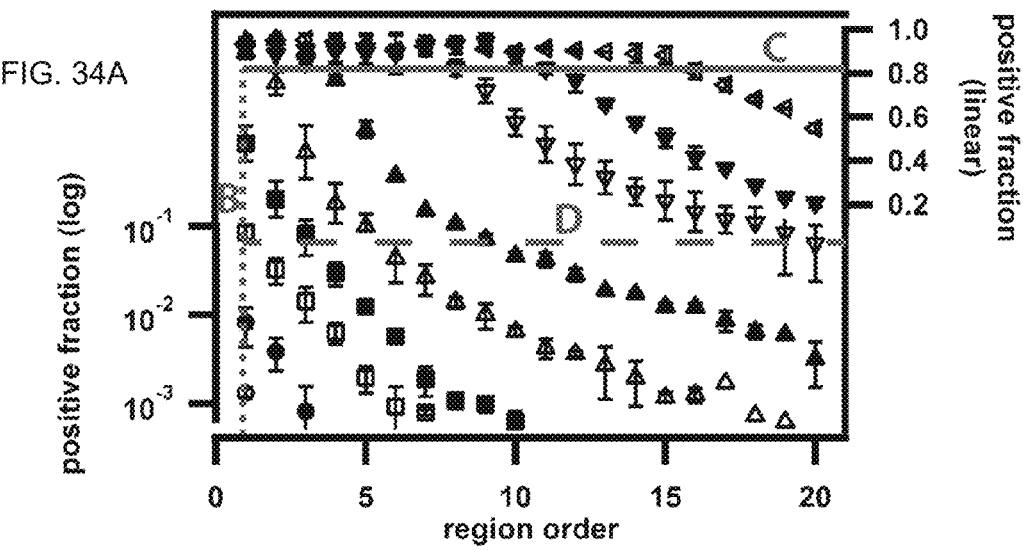
FIG. 34A
FIG. 34B
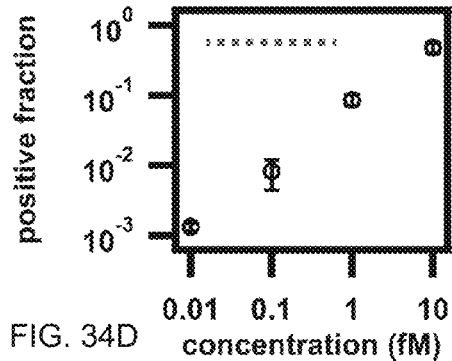
FIG. 34C
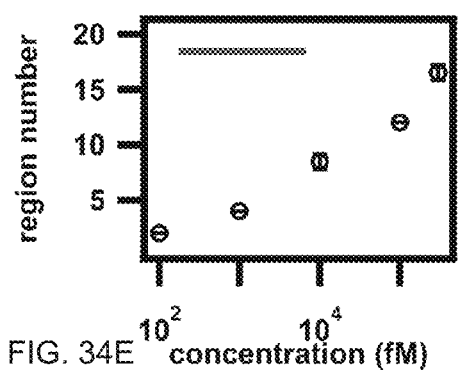
FIG. 34D
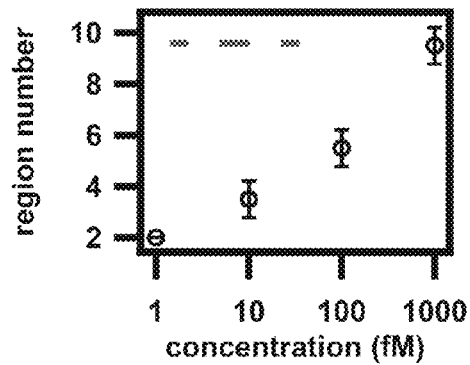
FIG. 34E
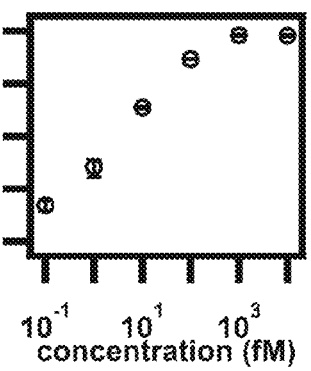

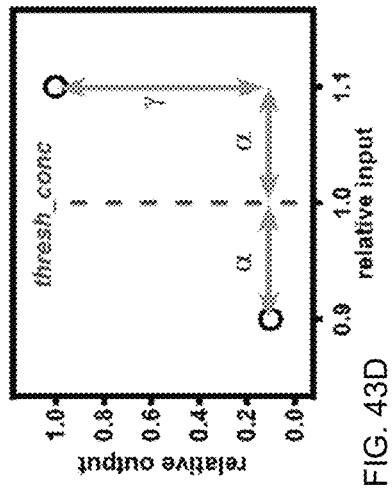
FIG. 43A
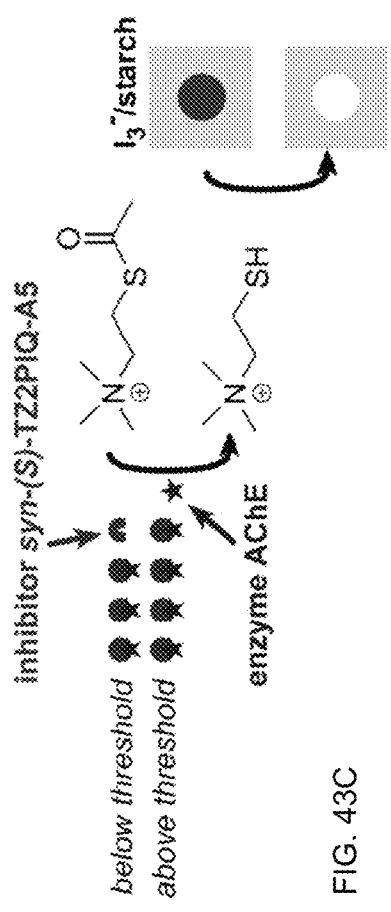
FIG. 43B
FIG. 43C
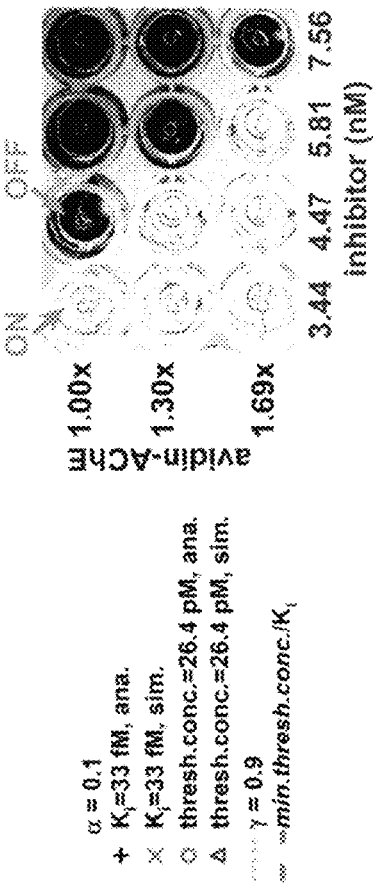
FIG. 43D
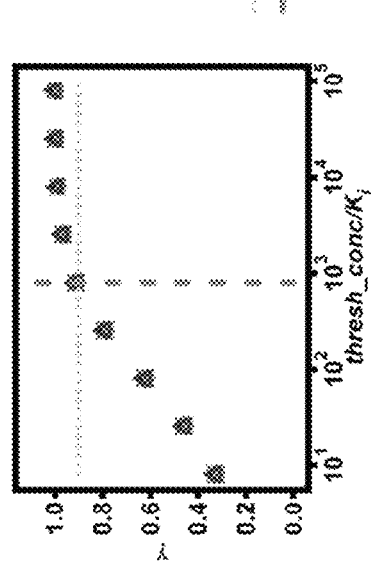

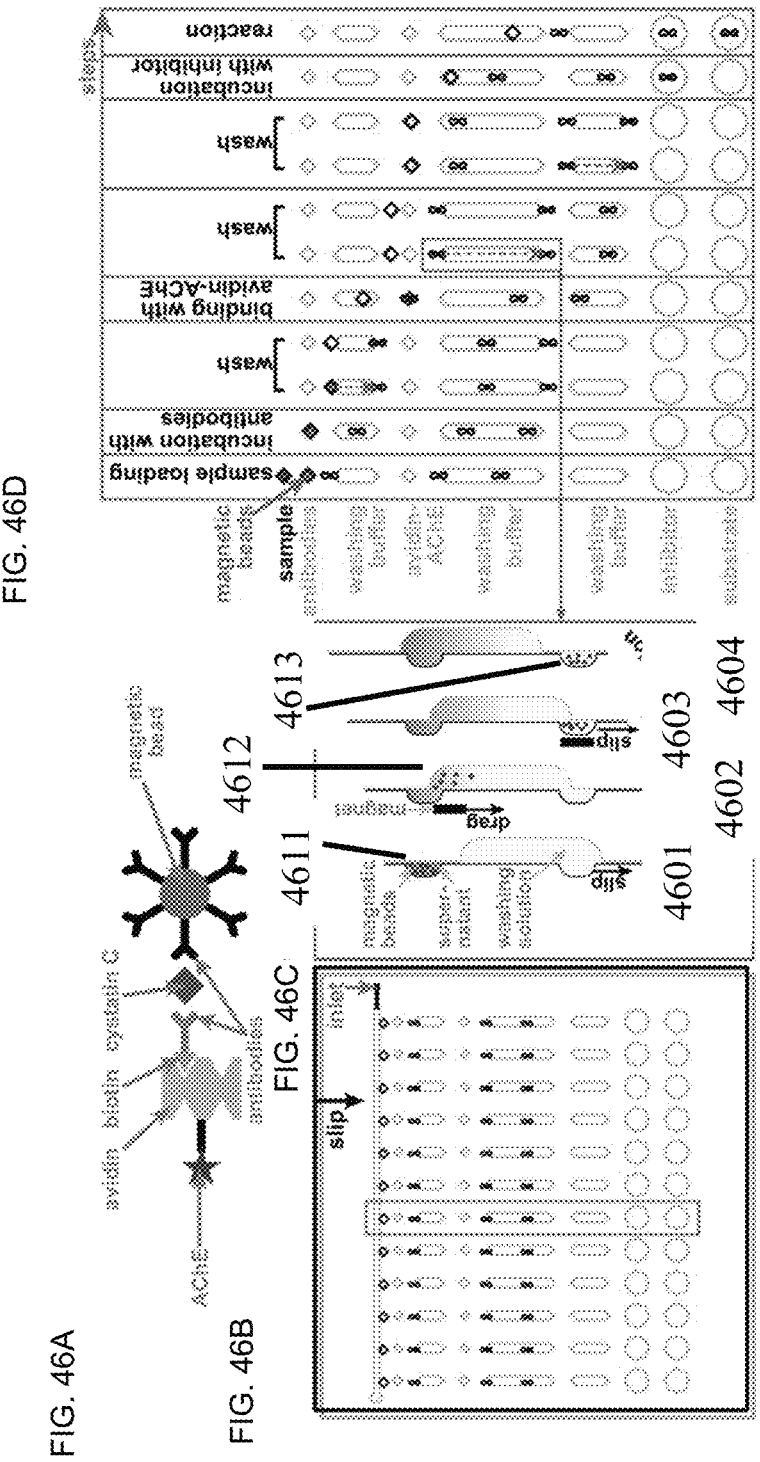

DIGITAL ASSAY FOR QUANTIFYING AND CONCENTRATING ANALYTES

CROSS-REFERENCE

This application is a Continuation of U.S. National Phase patent application PCT/US2014/047092, filed Jul. 17, 2014, which claims the benefit of U.S. Provisional Application No. 61/856,155, filed Jul. 19, 2013, and the benefit of U.S. Provisional Application No. 61/880,399, filed Sep. 20, 2013, and the benefit of U.S. Provisional Application No. 61/969,008, filed Mar. 21, 2014, which applications are incorporated herein by reference.

STATEMENT AS TO FEDERALLY SPONSORED RESEARCH

This invention was made with government support under Grant No. OD003584 awarded by the National Institutes of Health, and under Contract number Cooperative Agreement HR0011-11-2-0006 awarded by the Defense Advanced Research Projects Agency (DARPA), and under Grant No. N00014-08-1-0936 awarded by the Office of Naval Research. The government has certain rights in the invention.

BACKGROUND

The identity and amount analytes, including but not limited to nucleic acids, proteins, and cells, can provide valuable information about the samples and subjects from which they are taken. For example, the presence or severity of an infection can be measured. Markers for a wide range of conditions, from HIV to traumatic brain injury, can be assessed and quantified. In particular, portable methods for measuring and characterizing analytes are useful. Devices capable of analyzing samples can permit use of diagnostics and assays in remote locations, in resource-poor settings, or at the point of care.

SUMMARY

Disclosed herein are methods, devices, systems, and kits for the analysis of samples and analytes. In some cases, digital units are used, which are capable of capturing or binding analytes. Positive signal can be generated in response to the analytes, and the number, identity, and/or position of digital units from which positive signal is generated can be used to determine the identity and/or concentration of the analytes.

An aspect of the present disclosure provides a method for analyzing a sample, comprising providing a device comprising a fluid inlet, a fluid receiving structure, a fluid path connecting said fluid inlet and said receiving structure, and a plurality of digital units located along said fluid path, each digital unit capable of capturing at least one analyte; flowing a fluid sample along said fluid path, said fluid sample comprising analytes; binding a subset of said analytes to said digital units; and determining the concentration or identity of said analytes in said fluid sample.

In an embodiment, prior to said determining, a first subset of said plurality of digital units is isolated from a second subset of said plurality of digital units.

In an embodiment, a fluid receiving structure comprises one or more of an outlet; an absorbent, a dead-end filling structure, a chamber, a reservoir, or a well.

In an embodiment, said determining is conducted based on signal generated from said digital units.

In an embodiment, each of said digital units generates signal if the number of analytes captured thereby exceeds a threshold number.

In an embodiment, said threshold number is different between a first digital unit of said plurality of digital units and a second digital unit of said plurality of digital units.

In an embodiment, said threshold number is greater than one.

In an embodiment, said threshold number is greater than zero.

In an embodiment, the probability of signal being generated from each of said plurality of digital units depends of the number of analytes captured thereby.

In an embodiment, said probability is different between a first digital unit of said plurality of digital units and a second digital unit of said plurality of digital units.

In an embodiment, a first digital unit of said plurality of digital units and a second digital unit of said plurality of digital units are exposed to different amounts of sample.

In an embodiment, said different probability results from different surface areas.

In an embodiment, said different probability results from different binding affinities.

In an embodiment, said different probability results from different amounts of said fluid sample provided to said first digital unit and said second digital unit.

In an embodiment, said different probability results from different positions in said flow path of said first digital unit and said second digital unit.

In an embodiment, said probability is the same for each of said plurality of digital units.

In an embodiment, said determining comprises generating a profile of said signal versus location along said flow path and comparing said profile to a calibration profile.

In an embodiment, said determining comprises measuring the number of said digital units after which said signal decreases below a threshold value.

In an embodiment, said signal is generated by fluorescent labeling of analytes.

In an embodiment, said signal is generated by enzymatic reaction.

In an embodiment, said signal is optically detectable.
In an embodiment, said signal is electronically detectable.
In an embodiment, said signal is magnetically detectable.
In an embodiment, said signal is electromagnetic.

In an embodiment, said signal comprises the presence of a bead.

In an embodiment, said determining comprises a reaction.
In an embodiment, said determining comprises isothermal or non-isothermal gene amplification techniques.

In an embodiment, said determining comprises polymerase chain reaction (PCR), nucleic acid based sequencing (NASBA), self sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR.

In an embodiment, said determining comprises PCR.
In an embodiment, said determining comprises sequence determination.

In an embodiment, said sequence determination is performed using a method selected from the list consisting of Sanger sequencing, Illumina (Solexa) sequencing, pyrosequencing, next generation sequencing, maxam-gilbert sequencing, chain termination methods, shotgun sequencing, bridge PCR. Next generation sequencing methodologies may comprise Massively parallel signature sequencing, Polony sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Microscopy-based techniques, RNA Polymerase sequencing and In vitro virus high-throughput sequencing.

In an embodiment, said determining comprises genotyping.

In an embodiment, said determining comprises ELISA.

In an embodiment, said determining comprises enzyme multiplied immunoassay technique (EMIT), enzyme-linked immunosorbent assay (ELISA), sandwich ELISA, competitive ELISA, IgM antibody capture ELISA (MAC ELISA), microparticle enzyme immunoassay (MEIA), capillary electrophoresis immunoassays (CEIA); radioimmunoassays (RIA), immunoradiometric assays (IRMA), fluorescence polarization immunoassays (FPIA), or chemiluminescence assays (CL).

In an embodiment, said determining comprises antibody binding.

In an embodiment, said determining comprises an enzymatic reaction.

In an embodiment, said determining comprises hybridization.

In an embodiment, said plurality of digital units is organized into a plurality of capture regions.

In an embodiment, said determining comprises classifying each of said plurality of capture regions as positive or negative.

In an embodiment, said classifying comprises measuring signal from digital units in each of said capture regions.

In an embodiment, the relationship between the concentration of said analytes and the number of said capture regions classified as positive is non-linear.

In an embodiment, a doubling in the concentration of said analytes results in less than double the number of said capture regions classified as positive.

In an embodiment, said determining comprises comparing signal from said first subset of said digital units to signal from said second subset of said digital units.

In an embodiment, said isolating is achieved by physical motion of said digital units.

In an embodiment, said isolating is achieved by physical manipulation of said digital units.

In an embodiment, said isolating is achieved by introduction of an isolation fluid into said fluid path.

In an embodiment, said isolation fluid does not substantially enter said digital units.

In an embodiment, said isolation fluid is immiscible with said fluid sample.

In an embodiment, said isolation fluid does not preferentially wet said digital units.

In an embodiment, said isolation is achieved by flowing said isolation fluid over a pattern of wettable regions and non-wettable regions that cause said isolation fluid to be preferentially maintained by said wettable regions.

In an embodiment, said flowing comprises flow by capillary pressure.

In an embodiment, said flowing comprises flow by applied pressure.

In an embodiment, said flowing comprises flow by suction.

In an embodiment, said flowing comprises flow by applied vacuum.

In an embodiment, said flowing comprises flow by electric field.

In an embodiment, said flowing comprises flow by wicking.

In an embodiment, said flowing comprises flow by gravity.

In an embodiment, said flowing comprises flow by centrifugal force.

In an embodiment, said flowing comprises flow by magnetic force.

In an embodiment, said flowing comprises flow by surface tension gradient.

In an embodiment, said flowing comprises flow through said plurality of digital units.

In an embodiment, the method further comprises, after said capturing, washing said digital units.

In an embodiment, the method further comprises, after said capturing, neutralizing said digital units.

In an embodiment, prior to said determining, said analytes are released from said digital units.

In an embodiment, said digital units comprise a well.

In an embodiment, said digital units comprise a filter.

In an embodiment, said digital units comprise a reservoir.

In an embodiment, said digital units comprise a region of a substrate.

In an embodiment, said digital units comprise a bead.

In an embodiment, said digital units comprise a membrane.

In an embodiment, said digital units comprise pores.

In an embodiment, said digital units comprise gel.

In an embodiment, said digital units comprise a post.

In an embodiment, said digital units comprise charge-switch matrix.

An aspect of the present disclosure provides a method for analyzing a sample, comprising providing a device comprising a fluid inlet, a fluid receiving structure, a fluid path connecting said fluid inlet and said receiving structure, and a plurality of digital units located along said fluid path, each digital unit capable of capturing at least one analyte; flowing a fluid sample along said fluid path, said fluid sample comprising analytes; binding a subset of said analytes to said digital units; isolating a first subset of said digital units from a second subset of said digital units; and determining the concentration or identity of said analytes in said fluid sample.

In an embodiment, a fluid receiving structure comprises one or more of an outlet; an absorbent, a dead-end filling structure, a chamber, a reservoir, or a well.

In an embodiment, said determining is conducted based on signal generated from said digital units.

In an embodiment, each of said digital units generates signal if the number of analytes captured thereby exceeds a threshold number.

In an embodiment, said threshold number is different between a first digital unit of said plurality of digital units and a second digital unit of said plurality of digital units.

In an embodiment, said threshold number is greater than one.

In an embodiment, said threshold number is greater than zero.

In an embodiment, the probability of signal being generated from each of said plurality of digital units depends of the number of analytes captured thereby.

In an embodiment, said probability is different between a first digital unit of said plurality of digital units and a second digital unit of said plurality of digital units.

In an embodiment, a first digital unit of said plurality of digital units and a second digital unit of said plurality of digital units are exposed to different amounts of sample.

In an embodiment, said different probability results from different surface areas.

In an embodiment, said different probability results from different binding affinities.

In an embodiment, said different probability results from different amounts of said fluid sample provided to said first digital unit and said second digital unit.

In an embodiment, said different probability results from different positions in said flow path of said first digital unit and said second digital unit.

In an embodiment, said probability is the same for each of said plurality of digital units.

In an embodiment, said determining comprises generating a profile of said signal versus location along said flow path and comparing said profile to a calibration profile.

In an embodiment, said determining comprises measuring the number of said digital units after which said signal decreases below a threshold value.

In an embodiment, said signal is generated by fluorescent labeling of analytes.

In an embodiment, said signal is generated by phosphorescence labeling of analytes.

In an embodiment, said signal is generated by enzymatic reaction.

In an embodiment, said signal is optically detectable.

In an embodiment, said signal is electronically detectable.

In an embodiment, said signal is magnetically detectable.

In an embodiment, said signal is electromagnetic.

In an embodiment, said signal comprises the presence of beads.

In an embodiment, said determining comprises a reaction.

In an embodiment, said determining comprises isothermal or non-isothermal gene amplification techniques.

In an embodiment, said determining comprises polymerase chain reaction (PCR), nucleic acid based sequencing (NASBA), self sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR.

In an embodiment, said determining comprises PCR.

In an embodiment, said determining comprises sequence determination.

In an embodiment, said sequence determination is performed using the method selected from the list consisting of Sanger sequencing, Illumina (Solexa) sequencing, pyrosequencing, next generation sequencing, maxam-gilbert sequencing, chain termination methods, shotgun sequencing, bridge PCR. Next generation sequencing methodologies may comprise Massively parallel signature sequencing, Polony sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Microscopy-based techniques, RNA Polymerase sequencing and In vitro virus high-throughput sequencing.

In an embodiment, said determining comprises genotyping.

In an embodiment, said determining comprises enzyme multiplied immunoassay technique (EMIT), enzyme-linked immunosorbent assay (ELISA), sandwich ELISA, competitive ELISA, IgM antibody capture ELISA (MAC ELISA), microparticle enzyme immunoassay (MEIA), capillary electrophoresis immunoassays (CEIA); radioimmunoassays (RIA), immunoradiometric assays (IRMA), fluorescence polarization immunoassays (FPIA), or chemiluminescence assays (CL).

In an embodiment, said determining comprises ELISA.

In an embodiment, said determining comprises antibody binding.

In an embodiment, said determining comprises an enzymatic reaction.

In an embodiment, said determining comprises hybridization.

In an embodiment, said plurality of digital units is organized into a plurality of capture regions.

In an embodiment, said determining comprises classifying each of said plurality of capture regions as positive or negative.

In an embodiment, said classifying comprises measuring signal from digital units in each of said capture regions.

In an embodiment, the relationship between the concentration of said analytes and the number of said capture regions classified as positive is non-linear.

In an embodiment, a doubling in the concentration of said analytes results in less than double the number of said capture regions classified as positive.

In an embodiment, said determining comprises comparing signal from said first subset of said digital units to signal from said second subset of said digital units.

In an embodiment, said isolating is achieved by physical motion of said digital units.

In an embodiment, said isolating is achieved by physical manipulation of said digital units.

In an embodiment, said isolating is achieved by introduction of an isolation fluid into said fluid path.

In an embodiment, said isolation fluid does not substantially enter said digital units.

In an embodiment, said isolation fluid is immiscible with said fluid sample.

In an embodiment, said isolation fluid does not preferentially wet said digital units.

In an embodiment, said isolation is achieved by flowing said isolation fluid over a pattern of wettable regions and non-wettable regions that cause said isolation fluid to be preferentially maintained by said wettable regions.

In an embodiment, said flowing comprises flow by capillary pressure.

In an embodiment, said flowing comprises flow by applied pressure.

In an embodiment, said flowing comprises flow by applied vacuum.

In an embodiment, said flowing comprises flow by suction.

In an embodiment, said flowing comprises flow by electric field.

In an embodiment, said flowing comprises flow by wicking.

In an embodiment, said flowing comprises flow by gravity.

In an embodiment, said flowing comprises flow by centrifugal force.

In an embodiment, said flowing comprises flow by magnetic force.

In an embodiment, said flowing comprises flow by surface tension gradient.

In an embodiment, said flowing comprises flow through said plurality of digital units.

In an embodiment, the method further comprises, after said capturing, washing said digital units.

In an embodiment, prior to said determining, said analytes are released from said digital units.

In an embodiment, said digital units comprise a well.

In an embodiment, said digital units comprise a filter.

In an embodiment, said digital units comprise a region of a substrate.

In an embodiment, said digital units comprise a bead.

In an embodiment, said digital units comprise a membrane.

In an embodiment, said digital units comprise pores.

In an embodiment, said digital units comprise gel.

In an embodiment, said digital units comprise a post.

In an embodiment, said digital units comprise charge-switch matrix.

An aspect of the present disclosure provides a device for analyzing a sample comprising analytes, comprising: a fluid inlet, a fluid receiving structure, a fluid path connecting said fluid inlet and said fluid receiving structure, a plurality of digital units, wherein each digital unit is capable of capturing said at least one analyte; and a signal generator for generating signal from said digital units.

In an embodiment, said signal generator generates a signal from each of said digital units if the number of analytes bound thereto exceeds a threshold number.

In an embodiment, said threshold number is greater than one.

In an embodiment, said threshold number is greater than zero.

In an embodiment, said threshold number for a first digital unit of said digital units is different than said threshold number for a second digital unit of said digital units.

In an embodiment, the probability of said signal generator generating a signal from a digital depends on the number of analytes captured by that digital unit.

In an embodiment, the number of digital units from which signal is generated is correlated to the amount of said analytes in said sample.

In an embodiment, the number of digital units along said flow path after which said signal decreases below a threshold value is correlated to the amount of said analytes in said sample.

In an embodiment, said generating signal comprises a reaction.

In an embodiment, said generating signal comprises fluorescent labeling of said analytes.

In an embodiment, said generating signal comprises an enzymatic reaction.

In an embodiment, said signal is fluorescent.

In an embodiment, said signal is phosphorescent.

In an embodiment, said signal is colorimetric.

In an embodiment, said signal is optically detectable.

In an embodiment, said signal is electronically detectable.

In an embodiment, said signal is magnetically detectable.

In an embodiment, said signal comprises the presence of a bead.

In an embodiment, said signal generator comprises a fluorescent label.

In an embodiment, said signal generator comprises an antibody.

In an embodiment, said signal generator comprises a nucleic acid.

In an embodiment, said signal generator comprises an aptamer.

In an embodiment, said signal generator comprises an enzyme.

In an embodiment, said signal generator comprises metal.

In an embodiment, said signal generator comprises a protein.

In an embodiment, said signal generator comprises a peptide.

In an embodiment, said signal generator comprises a protein mimic.

In an embodiment, at least part of said sample flows through said digital units.

In an embodiment, said sample flows through said digital units.

In an embodiment, at least part of said sample flows over said digital units.

In an embodiment, said sample flows over said digital units.

In an embodiment, at least part of said sample flows around said digital units.

In an embodiment, said sample flows around said digital units.

In an embodiment, said digital units comprise a well.

In an embodiment, said digital units comprise a reservoir.

In an embodiment, said digital units comprise a filter.

In an embodiment, said digital units comprise a region of a substrate.

In an embodiment, said digital units comprise a bead.

In an embodiment, said digital units comprise a membrane.

In an embodiment, said digital units comprise pores.

In an embodiment, said digital units comprise gel.

In an embodiment, said digital units comprise a post.

In an embodiment, said digital units comprise charge-switch matrix.

In an embodiment, the smallest dimension of each of said digital units is less than or equal to about 1 mm.

In an embodiment, the smallest dimension of each of said digital units is less than or equal to about 500 µm.

In an embodiment, the smallest dimension of each of said digital units is less than or equal to about 300 µm.

In an embodiment, the smallest dimension of each of said digital units is less than or equal to about 100 µm.

In an embodiment, the smallest dimension of each of said digital units is less than or equal to about 50 µm.

In an embodiment, the smallest dimension of each of said digital units is less than or equal to about 20 µm.

In an embodiment, the smallest dimension of each of said digital units is less than or equal to about 10 µm.

In an embodiment, the smallest dimension of each of said digital units is less than or equal to about 5 µm.

In an embodiment, the smallest dimension of each of said digital units is less than or equal to about 1 µm.

In an embodiment, the volume of each of said digital units is less than or equal to 20 µL.

In an embodiment, the volume of each of said digital units is less than or equal to 5 µL.

In an embodiment, the volume of each of said digital units is less than or equal to 1 µL.

In an embodiment, the volume of each of said digital units is less than or equal to 100 nL.

In an embodiment, the volume of each of said digital units is less than or equal to 1 nL.

In an embodiment, the volume of each of said digital units is less than or equal to 30 pL.

In an embodiment, the volume of each of said digital units is less than or equal to 1 pL.

In an embodiment, the volume of each of said digital units is less than or equal to 30 fL.

In an embodiment, the volume of each of said digital units is less than or equal to 1 fL.

In an embodiment, said receiving structure comprises a hydrophobic element.

In an embodiment, the volume of said sample contacted to each of said digital units is fixed.

In an embodiment, the volume of said sample contacted to each of said digital units is fixed by the volume of fluid delivered to each of said digital units.

In an embodiment, the volume of said sample contacted to each of said digital units is fixed by the volume of fluid received by each of said digital units.

In an embodiment, said receiving structure comprises a hydrophobic element which allows flow of non-aqueous fluid and which blocks flow of aqueous fluid.

An aspect of the present disclosure provides a method, comprising providing a microfabricated device, said microfabricated device comprising a separation conduit comprising separation media, said separation media capable of binding or separating analytes; introducing a fluid sample comprising analytes into said separation conduit; contacting an access structure with said separation media; and transferring reagent from said access structure to said separation media.

In an embodiment, the method further comprises conducting a reaction with said reagent and said analytes.

In an embodiment, said separation media comprises chromatography media.

In an embodiment, said separation media comprises immunochromatography media.

In an embodiment, said separation media comprises electrophoresis media.

In an embodiment, said separation media comprises gel electrophoresis media.

In an embodiment, said reagent comprises an affinity reagent.

In an embodiment, said reagent comprises an antibody.

In an embodiment, said reagent comprises an aptamer.

In an embodiment, said reagent comprises a nucleic acid.

In an embodiment, said access structure is not in contact with the separation conduit prior to said contacting.

In an embodiment, said access structure is not in contact with the separation conduit after said transferring.

In an embodiment, the volume of said access structure is fixed.

In an embodiment, said access structure and said separation conduit are in co-planar microfabricated structures.

In an embodiment, said co-planar microfabricated structures remain coupled during said providing, said introducing, said contacting, and said transferring.

In an embodiment, said access structure remains within 30 mm of said separation conduit during said providing, said introducing, said contacting, and said transferring.

In an embodiment, said access structure remains within 10 mm of said separation conduit during said providing, said introducing, said contacting, and said transferring.

In an embodiment, said access structure remains within 3 mm of said separation conduit during said providing, said introducing, said contacting, and said transferring.

In an embodiment, said access structure remains within 1 mm of said separation conduit during said providing, said introducing, said contacting, and said transferring.

In an embodiment, the smallest dimension of said access structure is less than about 1 mm.

In an embodiment, the smallest dimension of said access structure is less than about 500 μm.

In an embodiment, the smallest dimension of said access structure is less than about 300 μm.

In an embodiment, the smallest dimension of said access structure is less than about 100 μm.

In an embodiment, the smallest dimension of said access structure is less than about 50 μm.

In an embodiment, the volume of said access structure is less than about 500 μL.

In an embodiment, the volume of said access structure is less than about 100 μL.

In an embodiment, the volume of said access structure is less than about 20 μL.

In an embodiment, the volume of said access structure is less than about 5 μL.

In an embodiment, the volume of said access structure is less than about 1 μL.

In an embodiment, the volume of said access structure is less than about 100 nL.

In an embodiment, said transferring comprises diffusion.

In an embodiment, said transferring comprises electric field-driven flow.

In an embodiment, said transferring comprises magnetic-field driven flow.

In an embodiment, said transferring comprises capillary pressure-driven flow.

In an embodiment, said transferring comprises applied pressure-driven flow.

In an embodiment, said transferring comprises applied vacuum-driven flow.

In an embodiment, said separation conduit remains substantially isolated from the ambient environment during said transferring.

In an embodiment, said separation media comprises a bead.

In an embodiment, said separation media comprises gel.

In an embodiment, said separation media comprises a solid-phase matrix.

In an embodiment, said separation media comprises an affinity matrix capable of preferentially binding said analytes.

In an embodiment, said separation media comprises an antibody.

In an embodiment, said separation media comprises an aptamer.

In an embodiment, said separation media comprises a nucleic acid.

In an embodiment, said separation media comprises magnetic material.

In an embodiment, said contacting comprises contacting multiple access structures.

In an embodiment, the amount of analyte contacted by a first access structure is different than the amount of analyte contacted by a second access structure.

In an embodiment, said introducing occurs by an applied pressure gradient.

In an embodiment, said introducing occurs by an electric field.

In an embodiment, said introducing occurs by a magnetic field.

In an embodiment, said introducing occurs by capillary pressure.

In an embodiment, the method further comprises analyzing said analytes.

In an embodiment, said determining comprises enzyme multiplied immunoassay technique (EMIT), enzyme-linked immunosorbent assay (ELISA), sandwich ELISA, competitive ELISA, IgM antibody capture ELISA (MAC ELISA), microparticle enzyme immunoassay (MEIA), capillary electrophoresis immunoassays (CEIA); radioimmunoassays (RIA), immunoradiometric assays (IRMA), fluorescence polarization immunoassays (FPIA), or chemiluminescence assays (CL).

In an embodiment, said analyzing comprises ELISA.

In an embodiment, said determining comprises isothermal or non-isothermal gene amplification techniques.

In an embodiment, said determining comprises polymerase chain reaction (PCR), nucleic acid based sequencing (NASBA), self sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR.

In an embodiment, said analyzing comprises PCR.

In an embodiment, said analyzing comprises isothermal amplification.

In an embodiment, said analyzing comprises sequencing.

In an embodiment, said sequence determination is performed using the method selected from the list consisting of Sanger sequencing, Illumina (Solexa) sequencing, pyrosequencing, next generation sequencing, maxam-gilbert sequencing, chain termination methods, shotgun sequencing, bridge PCR. Next generation sequencing methodologies may comprise Massively parallel signature sequencing, Polony sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Microscopy-based techniques, RNA Polymerase sequencing and In vitro virus high-throughput sequencing.

In an embodiment, said analyzing comprises hybridization.

In an embodiment, said analyzing comprises mass spectrometry.

In an embodiment, said mass spectrometry comprises chromatography coupled to mass spectroscopy (LC-MS) and two-dimensional liquid chromatography coupled to tandem mass spectroscopy (2D-LC-MS/MS), matrix-assisted laser desorption/ionisation time-of-flight (MALDI-TOF) MS; MALDI-TOF post-source-decay (PSD), surface-enhanced laser desorption/ionization time-of-flight mass spectrometry (SELDI-TOF) MS, electrospray ionization mass spectrometry (ESI-MS, ESI-MS/MS, ESI-MS/$(MS)^n$ (n is an integer greater than zero)), ESI 3D or linear (2D) ion trap MS, ESI triple quadrupole MS, ESI quadrupole orthogonal TOF (Q-TOF), ESI Fourier transform MS systems, desorption/ionization on silicon (DIOS), secondary ion mass spectrometry (SIMS), atmospheric pressure chemical ionization mass spectrometry (APCI-MS, APCI-MS/MS or APCI-$(MS)^n$) or atmospheric pressure photoionization mass spectrometry (APPI-MS, APPI-MS/MS, or APPI-$(MS)^n$)

An aspect of the present disclosure provides a method, comprising providing a microfabricated device, said microfabricated device comprising a separation conduit comprising separation media, said separation media capable of binding or separating analytes; introducing a fluid sample comprising analytes into said separation conduit; contacting an access structure with said separation media; and transferring said analytes from said separation media to said access structure.

In an embodiment, the method further comprises analyzing said analytes.

In an embodiment, the method further comprises conducting a reaction with said analytes.

In an embodiment, said access structure is not in contact with the separation conduit prior to said contacting.

In an embodiment, said access structure is not in contact with the separation conduit after said transferring.

In an embodiment, the volume of said access structure is fixed.

In an embodiment, said access structure and said separation conduit are in co-planar microfabricated structures.

In an embodiment, said co-planar microfabricated structures remain coupled during said providing, said introducing, said contacting, and said transferring.

In an embodiment, said access structure remains within 30 mm of said separation conduit during said providing, said introducing, said contacting, and said transferring.

In an embodiment, said access structure remains within 10 mm of said separation conduit during said providing, said introducing, said contacting, and said transferring.

In an embodiment, said access structure remains within 3 mm of said separation conduit during said providing, said introducing, said contacting, and said transferring.

In an embodiment, said access structure remains within 1 mm of said separation conduit during said providing, said introducing, said contacting, and said transferring.

In an embodiment, the smallest dimension of said access structure is less than about 1 mm.

In an embodiment, the smallest dimension of said access structure is less than about 500 µm.

In an embodiment, the smallest dimension of said access structure is less than about 300 µm.

In an embodiment, the smallest dimension of said access structure is less than about 100 µm.

In an embodiment, the smallest dimension of said access structure is less than about 50 µm.

In an embodiment, the volume of said access structure is less than about 20 µL.

In an embodiment, the volume of said access structure is less than about 5 µL.

In an embodiment, the volume of said access structure is less than about 1 µL.

In an embodiment, the volume of said access structure is less than about 100 nL.

In an embodiment, said transferring comprises diffusion.

In an embodiment, said transferring comprises electric field-driven flow.

In an embodiment, said transferring comprises magnetic-field driven flow.

In an embodiment, said transferring comprises capillary pressure-driven flow.

In an embodiment, said transferring comprises applied pressure-driven flow.

In an embodiment, said transferring comprises applied vacuum-driven flow.

In an embodiment, said separation conduit remains substantially isolated from the ambient environment during said transferring.

In an embodiment, said separation media comprises beads.

In an embodiment, said separation media comprises gel.

In an embodiment, said separation media comprises a solid-phase matrix.

In an embodiment, said separation media comprises an affinity matrix capable of preferentially binding said analytes.

In an embodiment, said separation media comprises an antibody.

In an embodiment, said separation media comprises an aptamer.

In an embodiment, said separation media comprises a nucleic acid.

In an embodiment, said separation media comprises a magnetic material.

In an embodiment, said contacting comprises contacting multiple access structures.

In an embodiment, the amount of analyte contacted by a first access structure is different than the amount of analyte contacted by a second access structure.

In an embodiment, said introducing occurs by an applied pressure gradient.

In an embodiment, said introducing occurs by an electric field.

In an embodiment, said introducing occurs by a magnetic field.

In an embodiment, said introducing occurs by capillary pressure.

In an embodiment, the method further comprises analyzing said analytes.

In an embodiment, said determining comprises enzyme multiplied immunoassay technique (EMIT), enzyme-linked immunosorbent assay (ELISA), sandwich ELISA, competitive ELISA, IgM antibody capture ELISA (MAC ELISA), microparticle enzyme immunoassay (MEIA), capillary electrophoresis immunoassays (CEIA); radioimmunoassays (RIA), immunoradiometric assays (IRMA), fluorescence polarization immunoassays (FPIA), or chemiluminescence assays (CL).

In an embodiment, said analyzing comprises ELISA.

In an embodiment, said determining comprises isothermal or non-isothermal gene amplification techniques.

In an embodiment, said determining comprises polymerase chain reaction (PCR), nucleic acid based sequencing (NASBA), self sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR.

In an embodiment, said analyzing comprises PCR.

In an embodiment, said analyzing comprises isothermal amplification.

In an embodiment, said analyzing comprises sequencing.

In an embodiment, said sequence determination is performed using the method selected from the list consisting of Sanger sequencing, Illumina (Solexa) sequencing, pyrosequencing, next generation sequencing, maxam-gilbert sequencing, chain termination methods, shotgun sequencing, bridge PCR. Next generation sequencing methodologies may comprise Massively parallel signature sequencing, Polony sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Microscopy-based techniques, RNA Polymerase sequencing and In vitro virus high-throughput sequencing.

In an embodiment, said analyzing comprises hybridization.

In an embodiment, said analyzing comprises mass spectrometry.

In an embodiment, said mass spectrometry comprises chromatography coupled to mass spectroscopy (LC-MS) and two-dimensional liquid chromatography coupled to tandem mass spectroscopy (2D-LC-MS/MS), matrix-assisted laser desorption/ionisation time-of-flight (MALDI-TOF) MS; MALDI-TOF post-source-decay (PSD), surface-enhanced laser desorption/ionization time-of-flight mass spectrometry (SELDI-TOF) MS, electrospray ionization mass spectrometry (ESI-MS, ESI-MS/MS, ESI-MS/(MS)$^n$ (n is an integer greater than zero)), ESI 3D or linear (2D) ion trap MS, ESI triple quadrupole MS, ESI quadrupole orthogonal TOF (Q-TOF), ESI Fourier transform MS systems, desorption/ionization on silicon (DIOS), secondary ion mass spectrometry (SIMS), atmospheric pressure chemical ionization mass spectrometry (APCI-MS, APCI-MS/MS or APCI-(MS)$^n$) or atmospheric pressure photoionization mass spectrometry (APPI-MS, APPI-MS/MS, or APPI-(MS)$^n$)

An aspect of the present disclosure provides a method comprising: introducing a volume of fluid sample into a sample chamber; introducing a volume of amplification reagents into said sample chamber; and conducting a detection reaction in said sample chamber; wherein said volume of fluid sample is at least about 100 times larger than said volume of detection reagents.

In an embodiment, said volume of fluid sample is at least about 1000 times larger than said volume of detection reagents.

In an embodiment, said detection reaction comprises nucleic acid amplification.

In an embodiment, said volume of fluid sample comprises less than or equal to about 10 analytes.

In an embodiment, said method is performed in parallel in at least two sample chambers.

In an embodiment, said method is performed in parallel in at least ten sample chambers.

In an embodiment, said sample chamber comprises separation media capable of capturing said analytes.

In an embodiment, said separation media is compatible with said detection reaction.

In an embodiment, said volume of fluid is greater than or equal to about 100 µL and less than or equal to about 10 mL.

In an embodiment, said volume of fluid is greater than or equal to about 1 mL and less than or equal to about 1000 mL.

In an embodiment, said sample comprises norovirus.

In an embodiment, said sample comprises hepatitis C virus.

In an embodiment, said sample comprises HIV.

An aspect of the present disclosure provides a method comprising: providing a first area comprising an analyte and a transfer agent; providing a second area; providing a third area; coupling said analyte to said transfer agent; bringing said first area into fluid contact with said second area; applying a force capable of moving said transfer agent at a greater rate than said analyte; moving said analyte coupled to said transfer agent from said first area to said second area via said force; bringing said second area into fluid contact with said third area; moving said analyte coupled to said transfer agent from said second area to said third area via said force; and isolating said third area from said second area.

In an embodiment, said force is electric.
In an embodiment, said force is magnetic.
In an embodiment, said force is optical.
In an embodiment, said force is from an applied pressure.
In an embodiment, said first area, said second area, and said third area do not change in volume during said moving.
In an embodiment, said second area is formed in a different substrate than said first area.
In an embodiment, said second area is formed in a different substrate than said third area.
In an embodiment, said first area is formed in a different substrate than said third area.
In an embodiment, said second area has length greater than its width or its depth.

An aspect of the present disclosure provides a method comprising: providing a first area comprising an analyte; providing a second area; providing a third area; bringing said first area into fluid contact with said second area; moving said analyte from said first area to said second area via said force; bringing said second area into fluid contact with said third area; moving said analyte from said second area to said third area via said force; and isolating said third area from said second area.

In an embodiment, said moving comprises diffusion of said analyte.
In an embodiment, said moving comprises application of a force to said analyte.
In an embodiment, said force is electric.
In an embodiment, said force is magnetic.
In an embodiment, said force is optical.
In an embodiment, said force is from an applied pressure.
In an embodiment, said first area, said second area, and said third area do not change in volume during said moving.
In an embodiment, said second area is formed in a different substrate than said first area.
In an embodiment, said second area is formed in a different substrate than said third area.
In an embodiment, said first area is formed in a different substrate than said third area.
In an embodiment, said second area has length greater than its width or its depth.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 26A shows an exemplary design of a photomask for fabricating microwells for use as digital units.

FIG. 26B shows an exemplary design of a photomask for fabricating channels to deliver sample to digital units.

FIG. 27A shows an exemplary electron micrograph of single beads loaded into wells, from an above view.

FIG. 27B shows an exemplary electron micrograph of single beads loaded into wells, from a cross-section view.

FIG. 27C shows an exemplary electron micrograph of single and pairs of beads loaded into wells, from an above view.

FIG. 27D shows an exemplary electron micrograph of single and pairs of beads loaded into wells, from a cross-section view.

FIG. 34A shows an exemplary experimental plot of the fraction of positive digital units per capture region for different analyte concentrations.

FIG. 34B shows an exemplary experimental plot of the fraction of positive digital units in the first capture region as a function of analyte concentration FIG. 34C shows an exemplary experimental plot of the number of regions that deplete samples of different analyte concentrations, with a threshold for a positive capture region set at 0.8 fraction of positive digital units.

FIG. 34D shows an exemplary experimental plot of the number of regions that deplete samples of different analyte concentrations, with a threshold for a positive capture region set at 0.07 fraction of positive digital units.

FIG. 34E shows an exemplary experimental logarithmic plot of the fraction of digital units with at least one captured analyte versus sample analyte concentration.

FIG. 39B).

FIG. 43A shows an exemplary schematic of the thresholding effect of inhibitors.

FIG. 43B shows an exemplary graph of parameters used to characterize threshold-controlled signal response.

FIG. 43C shows an exemplary graph of the effect of concentration compared to the threshold on the signal magnitude.

FIG. 43D shows an exemplary photograph of digital units producing positive signal (clear units) or negative signal (dark units) under the effect of different inhibitor and analyte concentrations.

FIG. 46A shows an exemplary schematic of a complex used in a magnetic bead-based immunoassay.

FIG. 46B shows an exemplary schematic of an overall device design for multiple threshold assays.

FIG. 46C shows an exemplary schematic of a washing technique.

FIG. 46D shows an exemplary schematic of steps for conducting an assay.

DETAILED DESCRIPTION OF THE INVENTION

Related Applications

Figure 1:
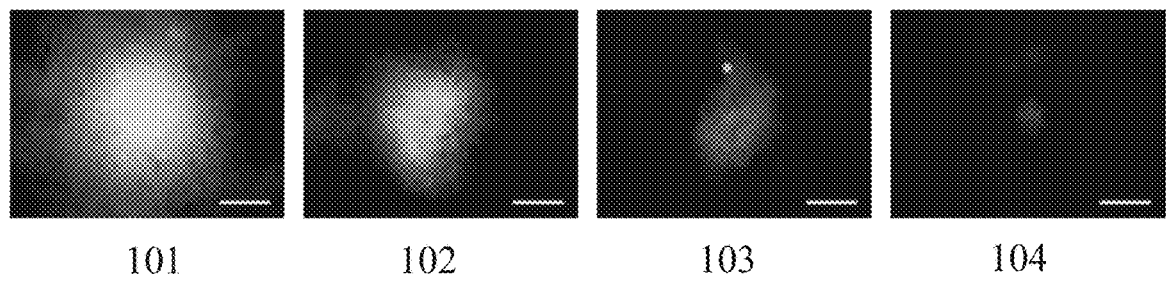
FIG. 1 shows exemplary fluorescent DNA bound to four layers of polymer membrane after DNA solution was flowed through the membrane stack.

We describe a number of devices and methods in this disclosure that can be used individually or in various combinations for applications including but not limited to those listed above. Furthermore, they can be used in various combinations with previously disclosed devices and methods for previously-described applications. The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011, and also to U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011. That United States application is a national stage entry of international application PCT/US2010/028361, "Slip Chip Device and Methods," filed on Mar. 23, 2010, which international application claimed priority to U.S. Application 61/262,375, "Slip Chip Device and Methods," filed on Nov. 18, 2009, to U.S. Application 61/162,922, "Sip Chip Device and Methods," filed on Mar. 24, 2009, and to U.S. Application 61/340,872, "Slip Chip Device and Methods," filed on Mar. 22, 2010.

We describe a number of devices and methods in this disclosure that can be used individually or in various combinations for applications including but not limited to those listed below. Furthermore, they can be used in various combinations with previously disclosed devices and methods for previously described applications. The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011, and also to U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011. That United States application is a national stage entry of international application PCT/US2010/028361, "Slip Chip Device and Methods," filed on Mar. 23, 2010, which international application claimed priority to U.S. Application 61/262,375, "Slip Chip Device and Methods," filed on Nov. 18, 2009, to U.S. Application 61/162,922, "Sip Chip Device and Methods," filed on Mar. 24, 2009, to U.S. Application 61/340,872, "Slip Chip Device and Methods," filed on Mar. 22, 2010, to U.S. application Ser. No. 13/440,371, "Analysis Devices, Kits, And Related Methods For Digital Quantification Of Nucleic Acids And Other Analytes," filed on Apr. 5, 2012, and to U.S. application Ser. No. 13/467,482, "Multivolume Devices, Kits, and Related Methods for Quantification and Detection of Nucleic Acids and Other Analytes," filed on May 9, 2012.

The following references are incorporated herein by reference: (a) Hoffmann, J., Solid-phase PCR in a picowell array for immobilizing and arraying 100,000 PCR products to a microscope slide. Lab on a Chip 2012; (b) Zhu, Z.; Zhang, W.; Leng, X.; Zhang, M.; Guan, Z.; Yang, C. J., Highly Sensitive and Quantitative Detection of Rare Pathogens through Agarose Droplet Microfluidic Emulsion PCR at the Single-Cell Level. Lab on a Chip 2012.

The term "about" or "nearly" as used herein refers to within plus or minus (+/−) 10%, 9%, 8%, 7%, 6%, 5%, 4%, 3%, 2%, or 1% of the designated amount.

This disclosure describes devices and methods for detection and quantification of analytes using digital units for capture, labeling, and subsequent detection of the analyte. Digital units can generate a positive signal based on capturing analyte. The number, identity, and/or location of positive digital units can be used to determine the identity, concentration, or amount of analyte in a sample.

The digital units can be continuous or discrete. These methods and devices can employ flow through digital units to allow a large effective binding area and capture agent concentration, which can be required by some assays. The probability of capture in each digital unit can be manipulated in a variety of ways to both detect and quantify analyte concentration in the sample. In some examples, the devices and methods can process large amounts of fluid in a short period of time by flowing through parallel units, further increasing sensitivity of the assay and decreasing total assay time.

The devices and methods can include components including but not limited to the following: 1) An array of digital units to isolate the analyte, 2) fluid reservoirs to store reagents and sample, and 3) a component that can create a flow. Furthermore, this disclosure describes elements and components that can be used for sample concentration, sample preparation, sample separation, and similar techniques. In some cases, the device can comprise a plurality of digital units that can each capture less than or equal to one analyte, followed by signal generation and detection to determine the number of digital units that contained an analyte. In some cases, the device comprises a plurality of digital units, which can process different sample volumes, and a threshold level of analyte is required to generate a positive signal; then the concentration of analyte can be determined by analyzing which digital units generated a positive signal. In some cases, the assay is based on the depletion of the sample as it flows through or over a series of digital units, and the concentration of analyte can be determined by analyzing which digital units generated a signal. In some examples the signal is a positive signal. In some instances, the signal is a negative signal. Sometimes, the signal is a zero signal (i.e. no signal).

Applications of these methods include, but are not limited to, determination of viral loads (e.g. HIV and HCV), identification of rare nucleic acids and rare cells (e.g. those indicative of cancer), diagnosis of infectious diseases, and monitoring treatments.

It should be understood that the methods, approaches and components described herein can be used individually or in combination.

Digital Units

The present disclosure provides for digital units. A binary signal (e.g., positive/negative, yes/no, on/off) can be produced from digital units in response to the presence or absence of analytes.

Figure 8A:
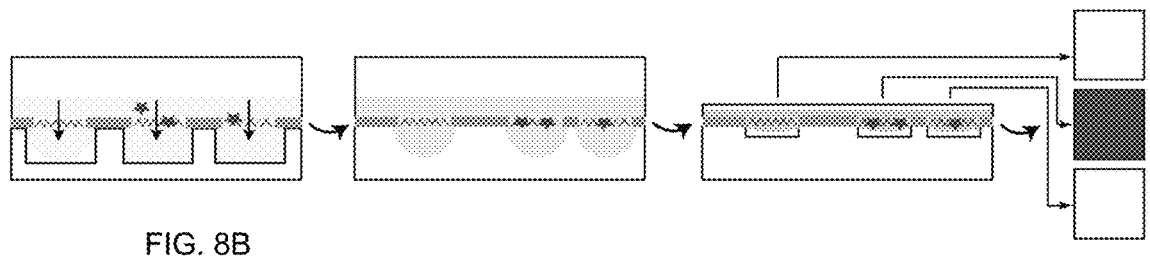
FIG. 8A shows exemplary binding of analyte, washing of capture matrix, elution into wells, and production of signal from wells.
Figure 8B:
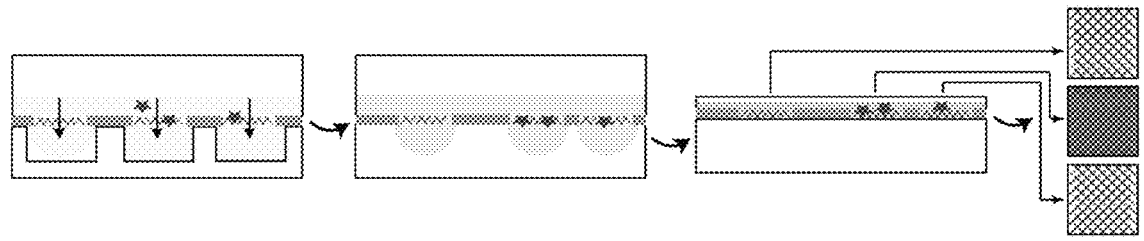
FIG. 8B shows exemplary of analyte, washing of capture matrix, on-matrix reaction, and production of signal from capture regions and elements.
Figure 9A:
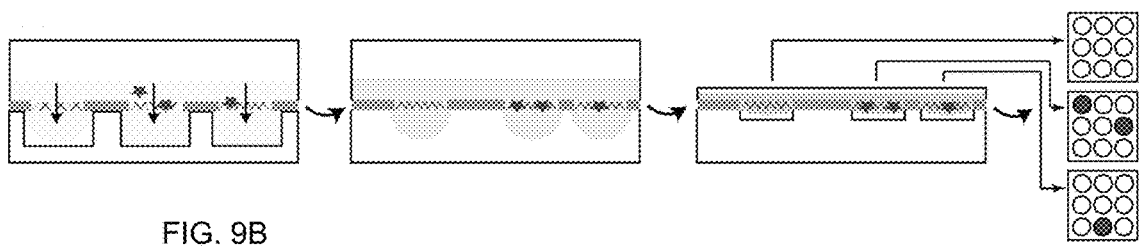
FIG. 9A shows exemplary binding of analyte, washing of capture matrix, elution into wells, and production of signal from wells.
Figure 9B:
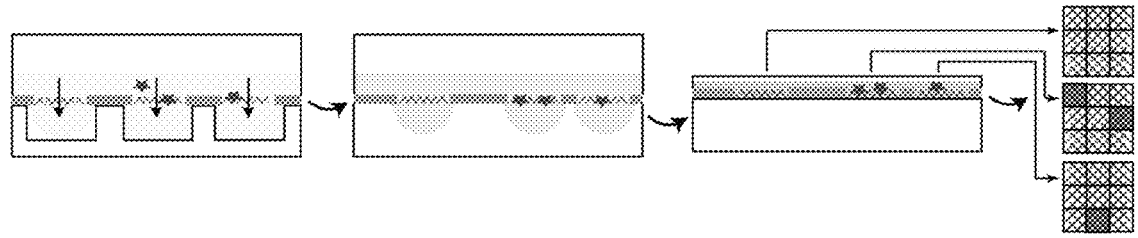
FIG. 9B shows exemplary binding of analyte, washing of capture matrix, on-matrix reaction, and production of signal from capture regions and elements.
Figure 10A:
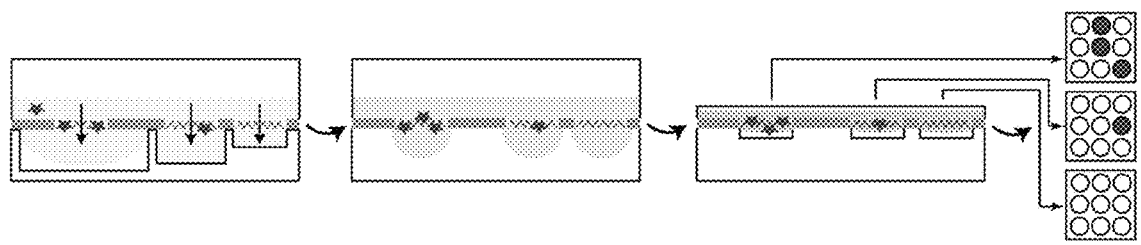
FIG. 10A shows exemplary binding of analyte, washing of capture matrix, elution into wells, and production of signal from wells.
Figure 10B:
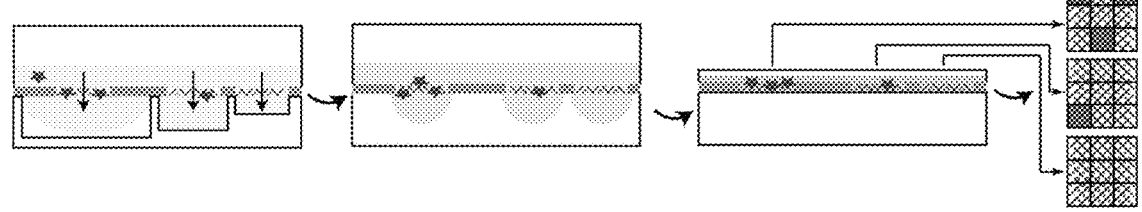
FIG. 10B shows exemplary binding of analyte, washing of capture matrix, on-matrix reaction, and production of signal from capture regions and elements.
Figure 20:
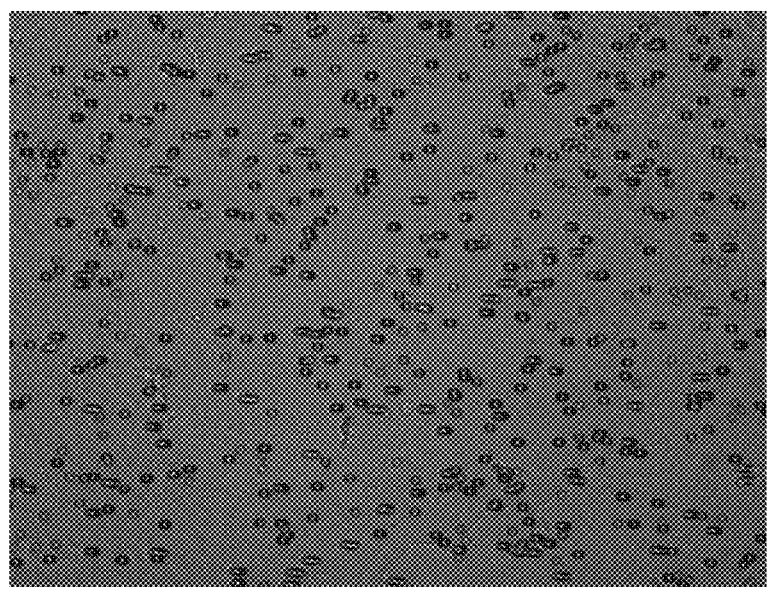
FIG. 20 shows exemplary digital units comprising pores in a membrane with gel.
Figure 22A:
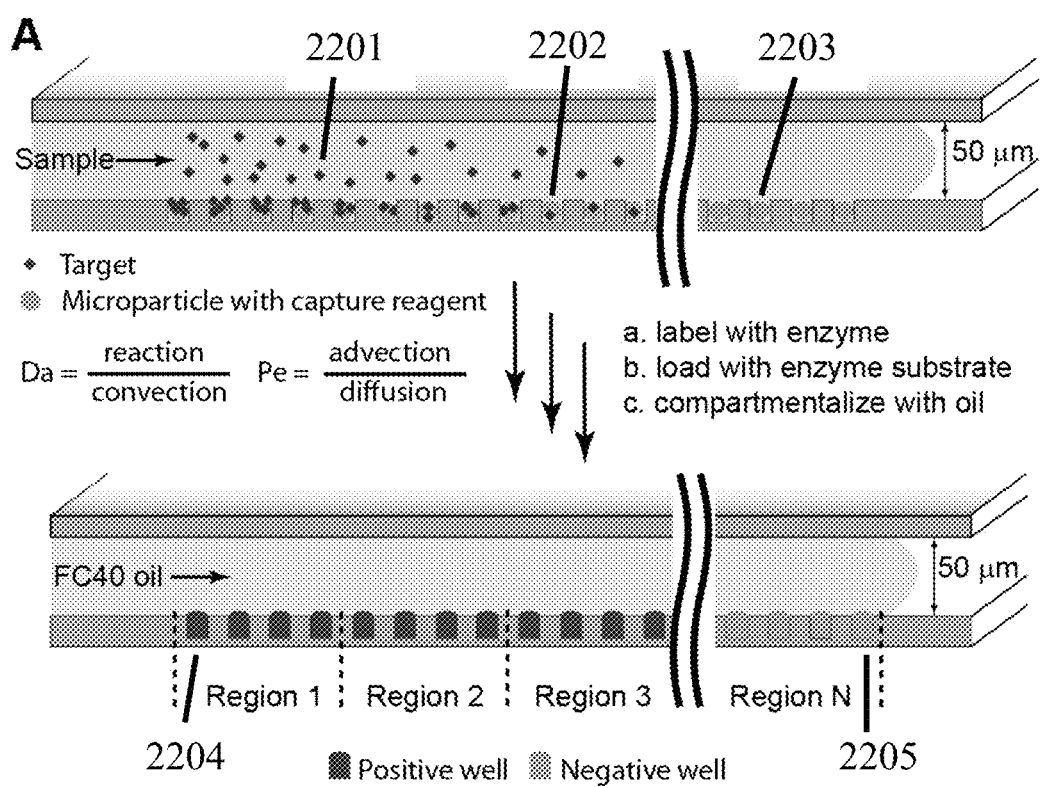
FIG. 22A shows an exemplary schematic of target analyte being captured in digital units.

Digital units can comprise a variety of structures or shapes, including but not limited to one or more wells (e.g., FIG. 38A), filters, membranes, gels, beads (e.g., magnetic, paramagnetic, nonmagnetic, metal, plastic), posts, pores (e.g., membrane pores), channels, or spots of a larger substrate. Digital units can comprise multiple structures or shapes, for example a well with an associated filter (e.g. FIG. 8, FIG. 9, FIG. 10), a gel inside a membrane pore (e.g., FIG. 20), or a bead inside a well (e.g., FIG. 22A, FIG. 27). For example, FIG. 22A shows sample with analyte 2201 being captured in digital units 2202, with empty digital units 2203 farther downstream; digital units with captured analyte 2204 generate positive signals while digital units without captured analyte 2205 do not.

Digital units can be arranged or organized in different configurations or patterns. For example, digital units can comprise a line, a curve, a flow path, a stack, a grid, an arc, an array, a disc, or a wedge arrangement. For example, FIG. 26 shows a schematic design of microwell digital units (FIG. 26A) which can be located along the flowpath of channels (FIG. 26B) Digital units can be organized or arranged into regions, which can be called capture regions or subsets. Capture regions or subsets can comprise one or more digital units. Digital units in different capture regions or subsets can be organized in the same or different arrangements. In some cases, digital units can be organized in multiple capture regions or subsets, each of which comprises a rectangular array of digital units. In some cases, digital units can be organized in multiple capture regions or subsets, some of which comprise rectangular arrays of digital units and some of which comprise wedge arrangements of digital units. Capture regions or subsets can be arranged or organized in different configurations or patterns. For example, capture regions can comprise a line, a curve, a flow path, a stack, a grid, an arc, an array, a disc, or a wedge arrangement. The capture regions can be arranged in parallel. In some instances, at least two of the capture regions are arranged in parallel. In some cases, at least two of the capture regions are arranged perpendicular to each other. In some cases, at least two of the capture rations are stacked in parallel. For example, FIG. 6 shows a schematic of a disc of capture material which can be divided into digital units and capture regions for analysis.

Digital units can be of different dimensions. The smallest linear dimension of a digital unit can be less than or equal to about 1 mm, 500 µm, 300 µm, 100 µm, 50 µm, 20 µm, 10 µm, 5 µm, or 1 µm. The smallest linear dimension of a digital unit can be greater than or equal to about 1 mm, 500 µm, 300 µm, 100 µm, 50 µm, 20 µm, 10 µm, 5 µm, or 1 µm. The volume of a digital unit can be less than or equal to about 20 µL, 5 µL, 1 µL, 100 nL, 1 nL, 30 pL, 1 pL, 30 fL, or 1 fL. The volume of a digital unit can be greater than or equal to about 20 µL, 5 µL, 1 µL, 100 nL, 1 nL, 30 pL, 1 pL, 30 fL, or 1 fL. Different digital units on a device can have different dimensions or the same dimensions. Different digital units within a capture region can have different dimensions or the same dimensions.

Figure 17:
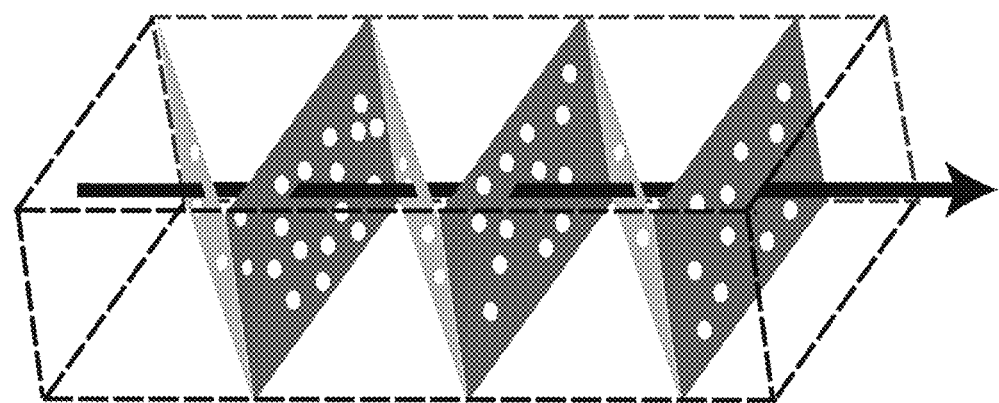
FIG. 17 shows exemplary digital units comprising pores with capture agent in a membrane, with the membrane folded into capture regions.
Figure 18:
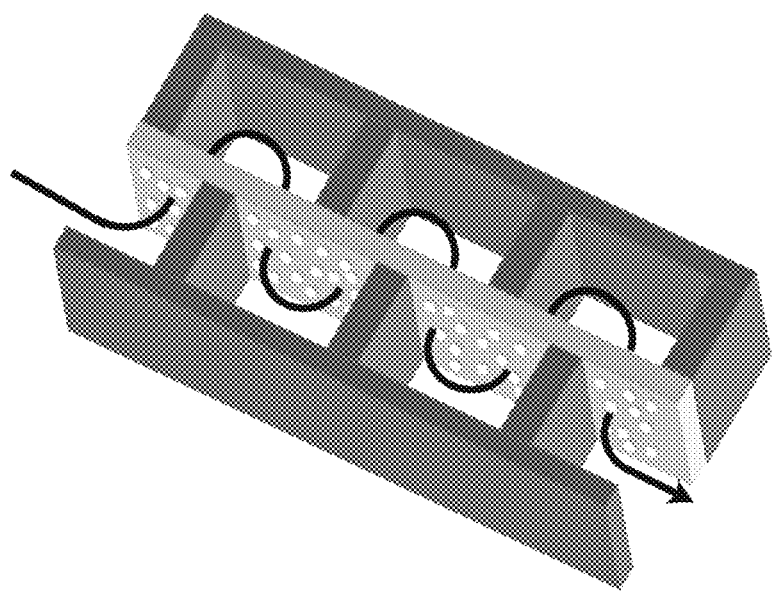
FIG. 18 shows exemplary digital units comprising pores with capture agent in a membrane, located inside a configuration of channels.

Sample can be flowed over, around, into, or through at least one digital unit or capture region. The sample can flow perpendicular or parallel to at least one digital unit or capture region. For example: sample can be flowed over at least one spot; sample can be flowed around at least one post or bead; sample can be flowed through at least one filter, membrane, or gel; sample can be flowed into at least one well. Digital units or capture regions can be arranged in parallel (e.g. flowing sample or reagents through multiple digital units or capture regions simultaneously), in series (e.g. flowing sample or reagents through digital units or capture regions sequentially), or a combination of the two. In some examples, at least two capture regions are arranged in parallel to each other. In some instances, at least two capture regions are arranged perpendicular to each other. In some cases, at least two capture regions are stacked in parallel to each other. In some examples, at least two digital units are arranged in parallel to each other. In some instances, at least two digital units are arranged perpendicular to each other. In some cases, at least two digital units are stacked in parallel to each other. For example, FIG. 1 shows images of analyte bound to four membranes 101, 102, 103, 104 which were arranged in a stack and flowed through in series with sample comprising analyte. Digital units and capture regions can have multidimensional structures, including rough surfaces, nanostructures or nanotubes, or dense oriented arrays. Digital units and capture regions can be present on multiple surfaces of a channel. For example, FIG. 17 shows digital units comprising pores with capture agent in a membrane, with the membrane folded into capture regions, allowing flow of sample through them in series. For another example, FIG. 18 shows digital units comprising pores with capture agent in a membrane, located inside a configuration of channels which divide the membrane into capture regions and allow flow through the capture regions sequentially. Analyte can move relative to digital units or capture regions. For example, analyte can move by methods including but not limited to diffusion, Brownian motion, convection, pumping, applied pressure, gravity-driven flow, density gradients, temperature gradients, chemical gradients, pressure gradients, gas-producing chemical reactions (e.g. decomposition of $H_2O_2$), centrifugal flow, capillary pressure, wicking, electric fields, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, or combinations thereof.

Digital units can comprise a reagent. The reagent can comprise amplification reagents, detection reagents, and/or other reagents. The reagent can comprise enzymes, cofactors, monomers, oligomers, nucleotides, dNTPs, rNTPs, oligonucleotides, or other reagents. In some cases, the reagent can be immobilized on or in the digital unit. Various fluids can be flowed through the digital units or capture regions. Flow can be of a sample fluid comprising analyte. As sample fluid flows through the capture matrix, analyte can bind to the capture matrix. The flow can be of a solution comprising reagent. The flow can be of a buffer, such as a wash buffer. Digital units can comprise multiple reagents.

Digital units can capture, trap, or bind analytes. Digital units can comprise a capture, binding, or affinity agent, including but not limited to one or more metal ions, gels (e.g., agarose, polyacrylamide) or filters (e.g., nitrocellulose, styrene/butadiene copolymer), aptamers (incorporating any of DNA, RNA, PNA, and/or modified bases), SOMAmers, engineered affinity proteins, carbohydrates, small molecules, synthetic peptides, repeat proteins (e.g., designed ankyrin-repeat proteins), affybody binding proteins, lipocalin, fibronectin, affinity reagent chimeras, nucleotides, oligonucleotides, DNA oligomers, RNA oligomers, PNA oligomers, antibody fragments, single chain antibody fragments (ScFv), full antibodies, proteins and protein mimics, recognition peptides, reverse-phase hydrophobic resins (e.g. C18 resin), or charge-switching ligands (e.g. chitosan, (poly) histidines) where the material charge can switch in response to pH changes. In some cases, a high density of capture agent can be achieved by incorporating the agent into a matrix with a high surface area to volume ratio. Digital units can comprise elements including, but not limited to, one or more magnetic beads coated with capture agent, polystyrene beads coated with capture agent, gel beads or particles loaded with capture agent (e.g., [Srinivas et al. "Aptamer-Functionalized Microgel Particles for Protein Detection." *Analytical Chemistry* (2007) 83, 9138-9145], [Appleyard et al. "Bar-coded hydrogel microparticles for protein detection: synthesis, assay and scanning." (2011) Vol 6, No 11, 1761-1774], [Appleyard et al, "Multiplexed Protein Quantification with Barcoded Hydrogel Microparticles." *Analytical Chemistry* (2011) 83, 193-1991), wicking hydrogel with imbedded capture agent, carbon nanotube forests with immobilized capture agent on the surface, pillar arrays with immobilized capture agent on the surface (non-porous) or within the pillar (porous) (e.g., [Srinivas et al, "Oil Isolated Hydrogel Microstructures for Sensitive Bioassays On-Chip." *Analytical Chemistry* (2013) 85, 12099-12107]), and/or a membrane with immobilized capture agent.]) Digital units can comprise multiple capture, binding, or affinity agents.

Membranes that contain different digital units can be fabricated on different ways. For example, membranes from different materials such as nitrocellulose, cellulose acetate, Loprodyne, or others can be functionalized with capture agents such as antibodies by directly spotting (printing) the capture agents onto the membrane, thereby forming digital units. These membranes can also be patterned for obtaining controlled spots of capture agents by using printing methods for controlled delivery of hydrophobic materials to the membrane material. These hydrophobic materials can selectively block flow on particular sections, while all liquid flows through the remaining sections of the membrane (e.g., as shown in [F. Deiss, W. L. Matochko, N. Govindasamy, E. Y. Lin and R. Derda, Angewandte Chemie International Edition, 2014, 53, 6374-6377]). In another example, membranes can be fabricated by using photolithographic techniques. Materials such as Parylene, Teflon or Cytop, among others, can be deposited onto a carrier substrate and subsequently be patterned with standard photolithography and dry etching techniques such as oxygen plasma etching to obtain through-holes of mm to μm-sized dimensions. An example of such a microfabrication method can be found in [S. Sakakihara, S. Araki, R. Iino and H. Noji, Lab Chip, 2010, 10, 3355-3362]. Capture agents such as antibodies can be deposited inside of through-holes in different ways. In some cases, micro- to nanometer-sized beads can be trapped inside of these through-holes. In some cases, hydrogel materials such as poly-ethylene glycol (PEG) can be deposited inside of these through-holes and subsequently be functionalized for capture agents such as antibodies. In some cases, the capture matrix comprises a polypropylene membrane. In some cases, digital units can comprise LoProdyne membrane functionalized with chitosan. In some cases, digital units can comprise LoProdyne membrane functionalized with a chitosan hydrogel. In some cases, the capture matrix comprises membranes of Parylene, polyimide, polycarbonate, cyclic olefin polymer, polymethylmethacrylate, and/or polypropylene. In some cases, the membranes are microfabricated for example, but not limited to, methods utilizing photolithography, microcontact printing, wet etching and/or dry etching. In some cases, membranes are track etched. In some cases, these membranes are functionalized with nitrocellulose, organogel, xerogel, or hydrogel (e.g., PEG, Chitosan, Polyvinyl alcohol). In some cases, the membranes contain packed beads and/or particles. In some cases, digital units can comprise polypropylene membrane functionalized with chitosan. In some cases, digital units can comprise polypropylene membrane functionalized with a chitosan hydrogel. Digital units can comprise multiple capture, binding, or affinity agents, for example a filter with associated nucleic acids, or a gel with associated antibodies. Capture, binding, or affinity agents can be present in sufficient number so as to prevent saturation of capture, binding, or affinity agents with analyte.

The capture, trapping, or binding probability of a digital unit can be controlled. Methods to control the probability of capture between digital units include, but are not limited to, varying element geometry (e.g. thickness, width, shape, size, and/or volume), varying capture agent affinity strength, varying capture agent concentration, and varying volumetric flow rate through the digital units. The volume of sample delivered to each digital unit can be controlled. The delivered volume can be controlled by controlling the volume of fluid contacted with the digital unit, for example by pipette, microfluidic droplet, contact with wells of defined volume, actuation of a SlipChip device, or other fluid handling methods. The delivered volume can be controlled by controlling the volume of fluid received by the digital unit, for example by controlling the volume of the digital unit, by controlling the hydrodynamic resistance of the digital unit, or by providing a defined receiving volume behind the digital unit (e.g., FIG. 8 left side, FIG. 9 left side, FIG. 10 left side). The delivered volume can be controlled by controlling the surface area of the digital unit.

Figure 3:
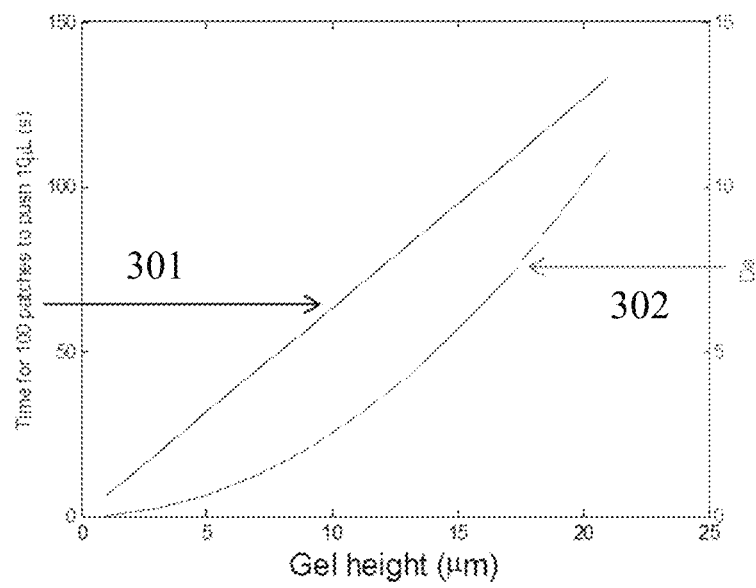
FIG. 3 shows exemplary values for simulated binding within capture regions.

The probability of a capture event can also be manipulated by changing the Damköhler number (Da), which represents the ratio of the reaction (binding) rate to the convection (flow) rate. For example, FIG. 3 shows the effect of gel height on time 301 and on Da 302. The number of capture, binding, or affinity agents in a given digital unit can be controlled. The capture probability or capture strength of capture agents in a given digital unit can be controlled. The volume of sample delivered to a given digital unit can be controlled. For example, set volumes of sample can be delivered to particular digital units, or digital units can have particular volumes and sample can be delivered to fill each digital unit. Digital units or capture regions can comprise different hydrodynamic resistances, affecting the proportion of sample encountering the digital units or capture regions. Multiple techniques for controlling the capture, trapping, or binding probability can be employed together. For example, both the number of capture, binding, or affinity agents in a given digital unit and the volume of sample delivered to that digital unit can be controlled. Different digital units can have different capture, trapping, or binding probabilities. Digital units organized into the same capture region or subset can have the same or different capture, trapping, or binding probabilities.

Figure 4A:
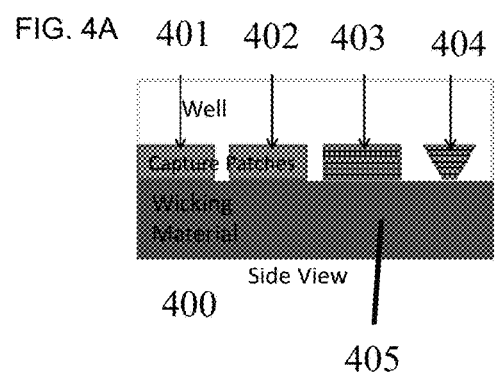
FIG. 4A shows exemplary side and top views of a schematic of a stacked multivolume element assay.
Figure 4B:
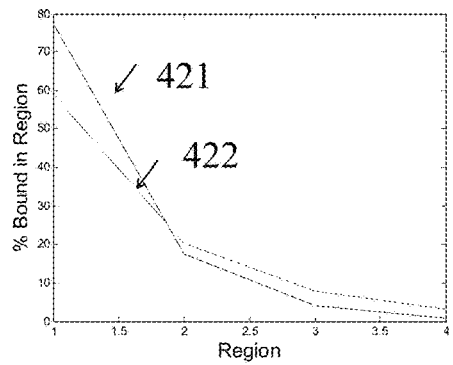
FIG. 4B shows an exemplary percentage of analyte expected to be bound in each capture region for two configurations of the stacked multivolume element assay of FIG. 4A.
Figure 5:
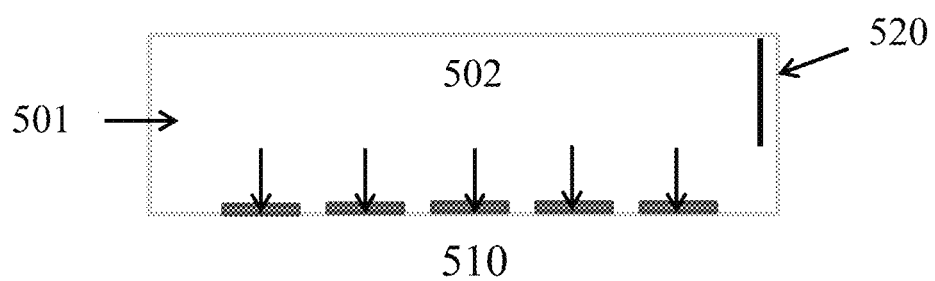
FIG. 5 shows an exemplary scheme of one capture region of digital units arranged in series, with parallel flow through the elements.
Figure 6A:
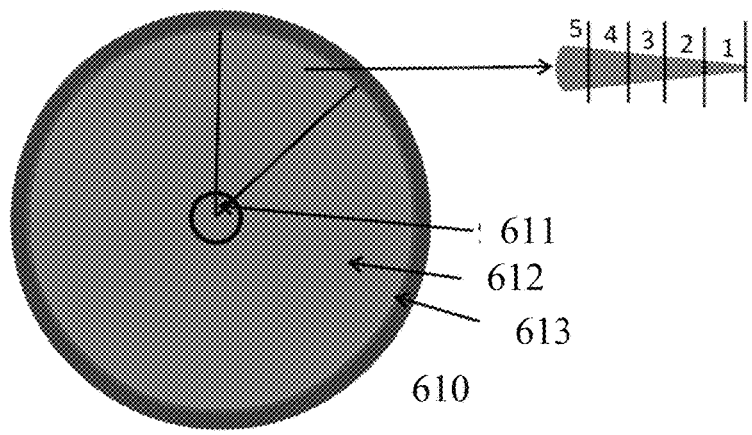
FIG. 6A shows an exemplary scheme of a circular capture matrix divided into wedges, with a wedge divided into capture regions.
Figure 6B:
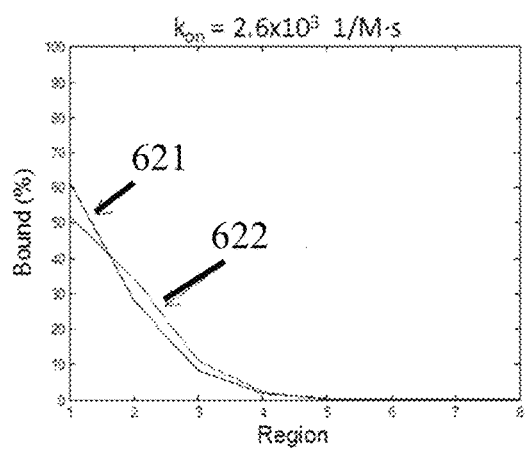
FIG. 6B shows an exemplary percentage of analyte expected to be bound in each capture region of a wedge of FIG. 6B for $k_{on}=2.6 \times 10^3$ 1/M·s.
Figure 6C:
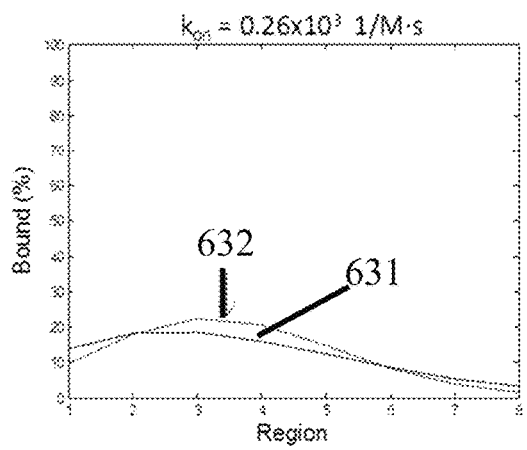
FIG. 6C shows an exemplary percentage of analyte expected to be bound in each capture region of a wedge of FIG. 6B for $k_{on}=0.26 \times 10^3$ 1/M·s.

Different digital unit or capture region geometries can be used. FIG. 4A shows an example device (side view 400 and top view 410) with both whole capture regions 401, 402 and subdivided (stacked) capture regions 403, 404. Decreasing the cross-sectional area of each capture region in the series (FIG. 4A, 404) can concentrate most of the analyte binding in the first (top) capture regions as the Da will decrease with the width. The analyte can deplete from the solution as it flows through the layers, but the amount of captured analyte in each region can further decrease as the Da decreases. This leads to a steep depletion curve as seen in FIG. 4B 421. If the stacked elements are the same size, then the depletion curve can be less steep 422. These depletion curves can also be correlated to a concentration, and can increase the resolution of the assay. The lower limit of detection can be determined by the maximum digital unit volume and flow rate, as well as the background signal (noise) of the assay. The dynamic range can be determined by the number and range of digital unit volumes and geometries. The digital unit and capture region geometry can vary by application. In some cases, digital units can be arranged simultaneously in series and parallel, either by creating an array of stacked capture regions (e.g. FIG. 4A) or by flowing a solution over digital units (e.g. FIG. 5). This could increase the throughput of an assay. As the sample passes over and simultaneously through the digital units or capture regions, it becomes more and more depleted with respect to analyte; a depletion curve can be plotted to analyze this relationship. The higher the concentration of the analyte, the more digital units or capture regions it takes to deplete the sample. A feature such as a pillar can optionally be added between capture regions of digital units to ensure the solution flowing over the digital units is well-mixed. In some examples, at least two capture regions are arranged in parallel to each other. In some instances, at least two capture regions are arranged perpendicular to each other. In some cases, at least two capture regions are stacked in parallel to each other. In some examples, at least two digital units are arranged in parallel to each other. In some instances, at least two digital units are arranged perpendicular to each other. In some cases, at least two digital units are stacked in parallel to each other. In some cases, digital units can be arranged in series and parallel in a circular depletion volume (e.g. FIG. 6, 610). This is equivalent to flow through a capture regions of increasing size, such as a wedge. Sample can be added in the center of the wedge 611, and can flow outward through digital units or capture regions 612 to the edge due to forces such as pressure in the center of the circle or a vacuum on the outer edge of the circle (FIG. 6A, 613). Due to the broadening of the wedge, the Da increases as the sample fluid moves towards the edge. This can create differential patterns of binding within the wedge, which can be seen if the wedge is broken into individual digital units (FIG. 6A, top right). The analyte can bind primarily in different regions depending on the affinity of the analyte to the capture agent and the geometry of the disc. A high affinity agent (e.g., $k_{on}$=2.6×10$^3$ 1/M s) can bind first (FIG. 6B, 621), where the flow can be too fast (Da is too low) for the low affinity reagent (e.g., $k_{on}$=0.26×10$^3$ 1/M s) to efficiently bind (FIG. 6C, 631). The profile of analyte binding can shift if the height of the disc linearly increases 622, 632, as the Da changes more sharply along the fluidic path. The wedges can be divided into digital units, and the number of digital units along the wedge with detectable bound analyte can be correlated to analyte concentration.

Signal can be generated from digital units. Signal generated from a digital unit can be binary, allowing that digital unit to be classified as positive (or on) versus negative (or off). A signal resulting in a digital unit being classified as positive can be referred to as a positive signal; a signal resulting in a digital unit being classified as negative can be referred to as a negative signal. Turn-on signals and turn-off signals can both be used; turn-off signals can be mathematically converted to turn-on signals and handled in a similar manner to turn-on signals. Classification of a digital unit can depend upon whether the signal from that digital unit exceeds a baseline or threshold value. Classification of a digital unit can depend upon whether the signal from that digital unit goes below a baseline or threshold value. The baseline value can be a predetermined value. The baseline value can be determined based on comparison to a reference digital unit or set of digital units. Signal generation is discussed further in this disclosure.

Analyte can be eluted from digital units. Elution can be performed by changing the surrounding chemical environment. For example, changing pH or salt conditions can lead to elution of DNA and RNA from charge switch or silica solid phases. The DNA or RNA can be single or double stranded. ChargeSwitch beads (Life Technologies, U.S. Pat. Nos. 6,718,742; 6,914,137; 7,319,004) can bind DNA at pH of 6.5 or less, and bound DNA can subsequently be eluted by raising pH to at most 8.5. The sample can be directly eluted into another section or layer of a device, or it can be eluted into a container (e.g. a well) or onto a substrate (e.g. a membrane or a gel) for removal and off-device analysis. Charge switch materials, having an ionizable group that changes charge based on ambient conditions, can be used. Such charge switch materials can be useful for ion exchange procedures to capture a target (e.g., a negatively charged target, such as a nucleic acid) with a charge switch material having positive charge at low pH (e.g., a pH of at most 6.0, or at most 6.5 or less; or a pH lower than or equal to the $pK_a$ of the ionizable group). Then, the target can be eluted by releasing it from the charge switch material, such as by elution at a raised pH (e.g., a pH of at least 8.5 or more, or a pH higher than the pKa of the ionizable group). Exemplary charge switch materials include those with an ionizable group selected from the group consisting of a biological buffer (e.g., -2-acetamido-2-aminoethanesulfonic acid (ACES); N-2-acetamido-2-iminodiacetic acid (ADA); amino methyl propanediol (AMP); 3-1,1-dimethyl-2-hydroxyethylamino-2-hydroxy propanesulfonic acid (AMPSO); N,N-bis2-hydroxyethyl-2-aminoethanesulfonic acid (BES); N,N-bis-2-hydroxyethylglycine (BICINE); bis-2-hydroxyethyliminotrishydroxymethylmethane (Bis-Tris); 1,3-bistrishydroxymethylmethylaminopropane (Bis-Tris Propane); 4-cyclohexylamino-1-butane sulfonic acid (CABS); 3-cyclohexylamino-1-propane sulfonic acid (CAPS); 3-cyclohexylamino-2-hydroxy-1-propane sulfonic acid (CAPSO); 2-N-cyclohexylaminoethanesulfonic acid (CHES); 3-N,N-bis-2-hydroxyethylamino-2-hydroxypropanesulfonic acid (DIPSO); -2-hydroxyethylpiperazine-N-3-propanesulfonic acid (EPPS); -2-hydroxyethylpiperazine-N-4-butanesulfonic acid (HEPBS); -2-hydroxyethylpiperazine-N-2-ethanesulfonic acid (HEPES); -2-hydroxyethylpiperazine-N-2-propanesulfonic acid (HEPPSO); 2-N-morpholinoethanesulfonic acid (MES); 4-N-morpholinobutanesulfonic acid (MOBS); 3-N-morpholinopropanesulfonic acid (MOPS); 3-N-morpholino-2-hydroxypropanesulfonic acid (MOPSO); piperazine-N—N-bis-2-ethanesulfonic acid (PIPES); piperazine-N—N-bis-2-hydroxypropanesulfonic acid (POPSO); N-trishydroxymethyl-methyl-4-aminobutanesulfonic acid (TABS); N-trishydroxymethyl-methyl-3-aminopropanesulfonic acid (TAPS); 3-N-trishydroxymethyl-methylamino-2-hydroxypropanesulfonic acid (TAPSO); N-trishydroxymethyl-methyl-2-aminoethanesulfonic acid (TES); N-trishydroxymethylmethylglycine (TRICINE); trishydroxymethylaminomethane (Tris); polyhydroxylated imidazoles; triethanolamine dimers and polymers; and di/tri/oligo amino acids, for example Gly-Gly, Ser-Ser, Gly-Gly-Gly, and Ser-Gly), a polyhydroxylated amine (e.g., TRIS or Bis-Tris), imidazole, histidine, and polyhistidine. In some embodiments, the charge switch material can include Bis-Tris, a Bis-Tris polymer (e.g., formed by attachment of Bis-Tris monomers to a polyacrylic acid (PAA) backbone), PAA, or a combination of Bis-Tris and PAA (e.g., where both Bis-Tris and PAA are in polymeric form and can formed as a copolymer or as layers including alternating Bis-Tris and PAA layers). In other embodiments, the charge switch material is a weakly basic polymer that has a cationic charge at acidic pH but has a neutral charge at basic pH. Such materials include poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(1-vinylimidazole-co-2-hydroxyethyl methacrylate), poly[N-(1,1-dimethyl-3-imidazolylpropyl) acrylamide], or poly(N-2-methyl-1-vinylimidazole. Additional charge switch materials include those that are pH-insensitive but targets charge changes. Further charge switch materials are described in U.S. Pat. Nos. 5,582,988, 6,914,137 and 7,319,004, each of which is incorporated herein by reference. Such materials and procedures are commercially available, such as in ChargeSwitch® Technology (available in numerous formats from Invitrogen Corp. or Life Technologies™ Corp., Carlsbad, Calif., such as in a ChargeSwitch® coated membrane, magnetic bead, or well plate). Further charge switch materials and/or ion exchange processes are described in U.S. Pat. Nos. 5,234,809, 6,718,742, 6,914,137, and 7,319,004; U.S. Pub. Nos. 2003/0008320, 2005/0053941, 2003/0054395, 2003/0173284, 2003/0130499, 2005/0053941, 2006/0154247, 2006/0263780, 2007/0122809, 2006/0024712, 2012/0196944, and 2012/0197009; and Int. Pub. Nos. WO 02/48164, WO 99/29703, WO 01/88185, WO 01/03149, WO 03/101494, WO 03/046177, WO 2005/012521, and WO 2006/004611, each of which is incorporated by reference in its entirety. The charge switch material can be combined with any useful format. In some instances, the charge switch material is combined with a magnetic particle (e.g., having a diameter between 20 micrometers and 1 mm) formed from any useful material (e.g., formed from magnetite, iron oxides, transition metal oxides, ferromagnetic materials, or paramagnetic materials). In some examples, the magnetic particles have an average diameter of at least about 20, 30, 40, 50, 60, 70, 80, 90, 100, 200, 300, 400, 500, 600, 700, 800, 900, 1000 micrometers or more. In some examples, the magnetic particles have an average diameter of at most about 20, 30, 40, 50, 60, 70, 80, 90, 100, 200, 300, 400, 500, 600, 700, 800, 900, 1000 micrometers or less. Exemplary charge switch materials include polymethacrylate carboxy ion-exchangers, silica particles coated with a negative charge, cellulose or agarose with phosphate or sulfate groups, or any negatively charged species. Exemplary magnetic particles are described in U.S. Pat. No. 6,718,742, which is incorporated herein by reference.

Assays

The present disclosure provides methods and devices for conducting assays. Digital units can be organized into capture regions, as described further in this disclosure, and sample comprising analyte can be contacted with the digital units. The number, identity, and/or location of digital units generating a positive signal can be used to determine the concentration and/or identity of the analyte, as discussed further in this disclosure.

Initial preparation can be performed in a well, a chamber, or a reservoir to remove potentially harmful components such as excessive protein, RNases, and DNases. For example, incubation with Proteinase K, Zygem reagent, or similar protease treatment can deactivate and digest unwanted proteins. After capture of the analyte from a large volume of fluid, amplification and detection can occur directly on the digital unit without the need for elution. Alternatively, analyte can be eluted prior to amplification or detection. Elution is discussed further in this disclosure.

An assay can comprise a flow-through digital assay, wherein sample can be flowed through digital units. Sample can be flowed entirely through the digital units. Sample can be flowed partly over or past the digital units 501 and partly through the digital units 502, for example as shown in FIG. 5. Some of the sample flow can be through the substrate, via the digital units 510. In some cases, the direction of fluid flow for sample entering digital units is not parallel to the substrate. A pillar or other obstruction 520 can optionally be located between sections or capture regions to facilitate mixing. Various configurations of digital unit can be used in conjunction with a flow-through assay, including but not limited to one or more filters, membranes, gels, beads, wells, pores, channels, or combinations thereof. In some cases, the digital units comprise distinct inlets and outlets for the sample and any assay reagents (e.g., labeling reagents).

The volume of sample delivered to each digital unit can be controlled. The delivered volume can be controlled by controlling the volume of fluid contacted with the digital unit, for example by pipette, microfluidic droplet, contact with wells of defined volume, actuation of a SlipChip device, or other fluid handling methods. The delivered volume can be controlled by controlling the volume of fluid received by the digital unit, for example by controlling the volume of the digital unit, by controlling the hydrodynamic resistance of the digital unit, or by providing a defined receiving volume behind the digital unit (e.g., FIG. 8 left side, FIG. 9 left side, FIG. 10 left side). The delivered volume can be controlled by controlling the surface area of the digital unit.

Flow-through of digital units can allow for concentration of analytes. As sample flows through the digital unit, analyte is captured by the digital unit, thereby concentrating it. In some cases, the concentration of analyte within a digital unit can be higher than the concentration of analyte in the original sample. The concentration of analyte in a digital unit can be at least about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times higher than in the original sample. Large volumes of sample can be delivered to digital units. The sample volume can be large compared to the volume of a digital unit, to the volume of reagent used, or to the volume of a device used. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times the volume of a digital unit. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000 or more times the reagent volume. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times the device volume. For example, a chitosan-coated membrane can isolate nucleic acids from samples with a concentrating factor of about 1000-fold (e.g., 5 milliliter (mL) to 5 microliter (µL)). This can allow isolation of analytes, such as free DNA or RNA, with concentrating factors of up to 1000-fold, without relying on resin slurries or filtration of cells.

Figure 29:
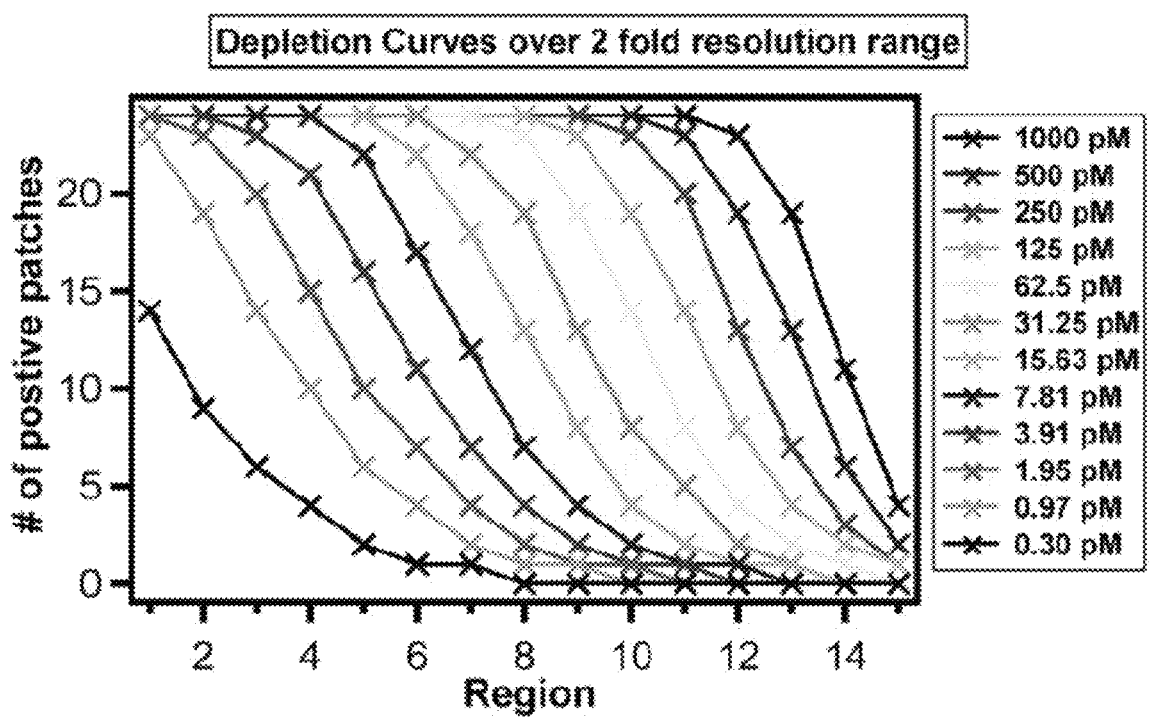
FIG. 29 shows exemplary simulated depletion curves over a two-fold resolution range from 0.30 picomolar (pM) to 1000 picomolar (pM) of analyte.
Figure 36:
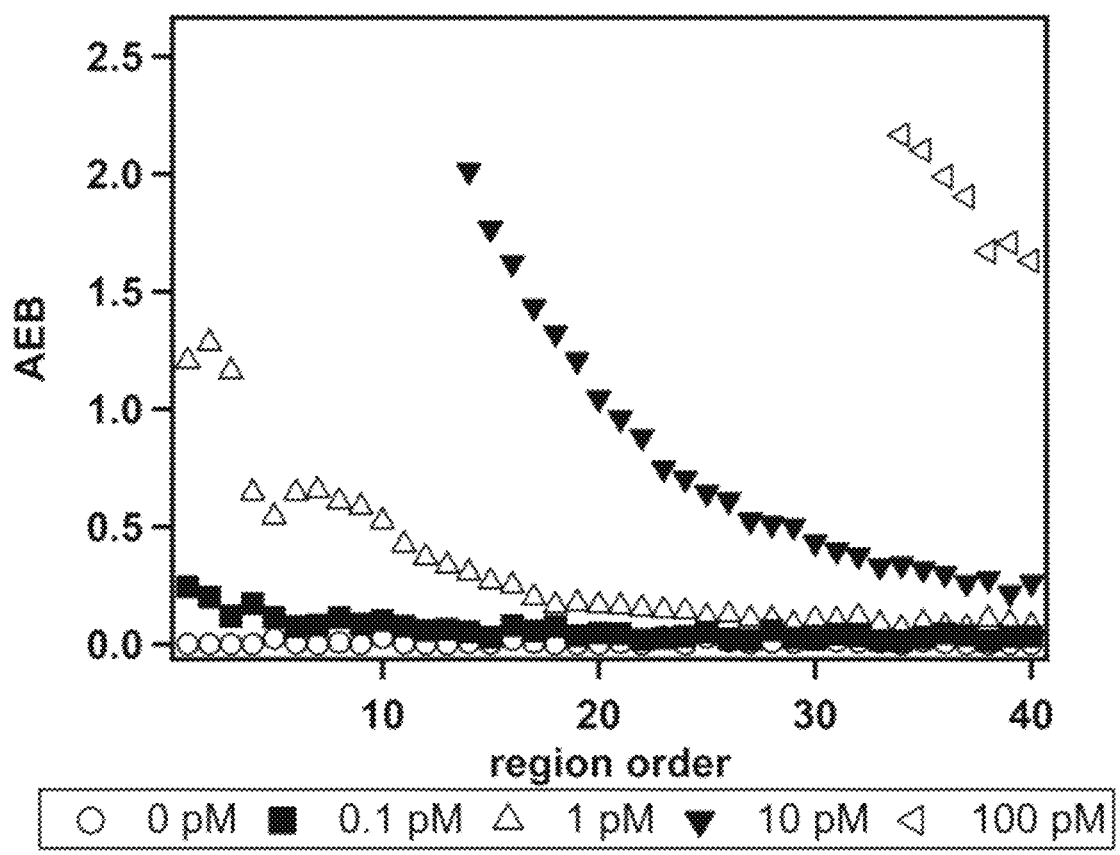
FIG. 36 shows exemplary experimental depletion curves for different concentrations (zero picomolar (pM), 0.1 pM, 1 pM, 10 pM, and 100 pM) of glial fibrillary acidic protein (GFAP).
Figure 37:
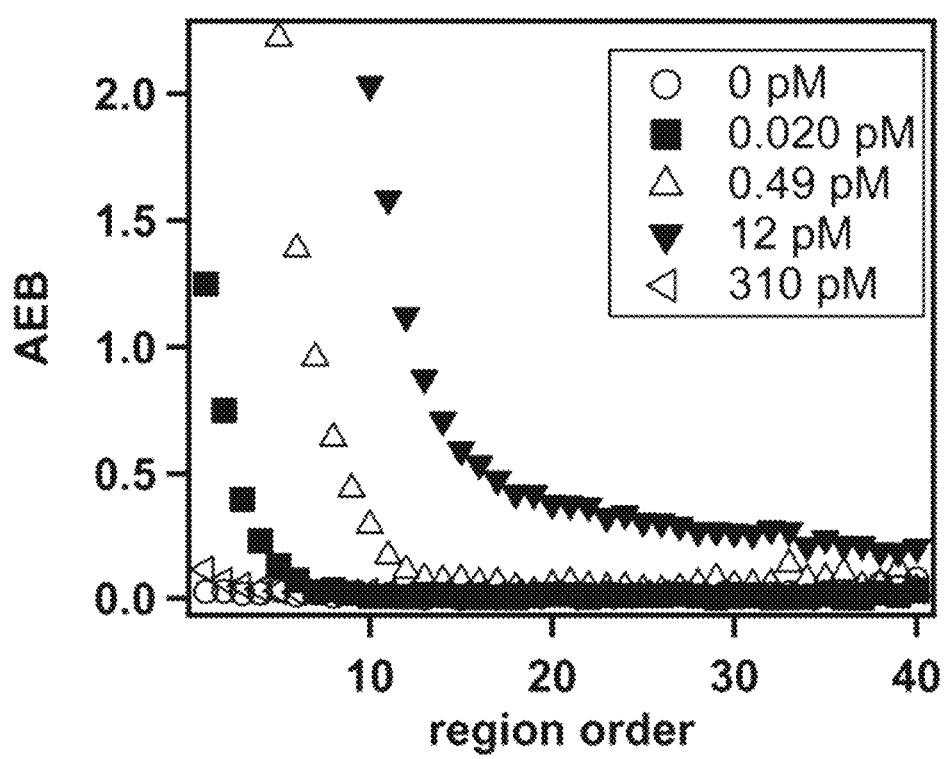
FIG. 37 shows exemplary experimental depletion curves for different concentrations (zero picomolar (pM), 0.020 pM, 0.49 pM, 12 pM, and 310 pM) of p24.
Figure 38A:
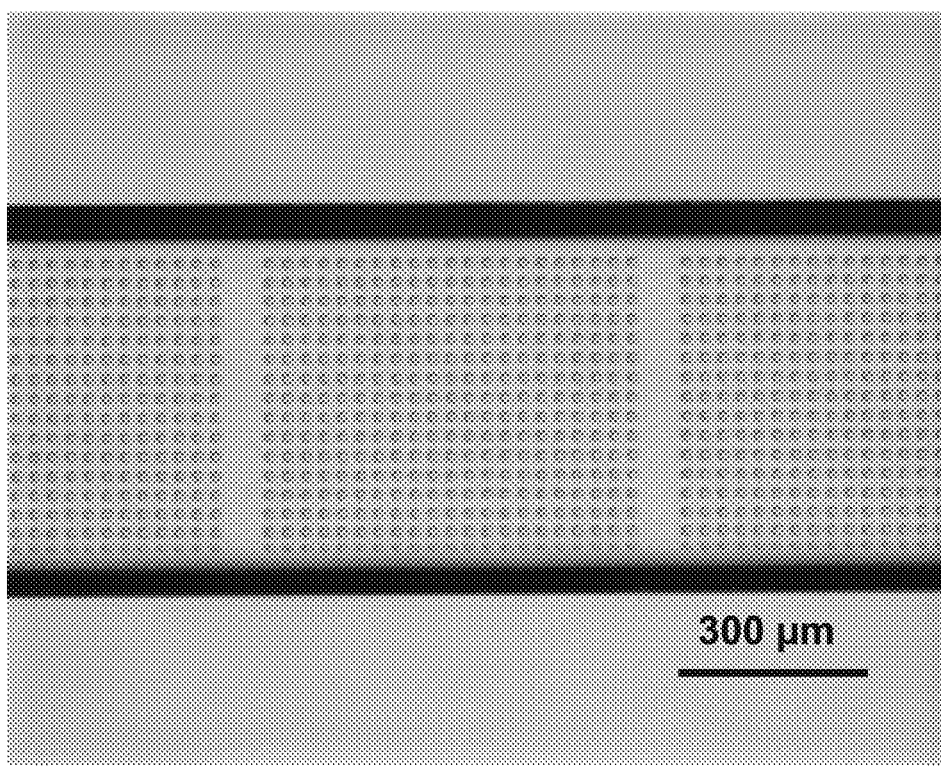
FIG. 38A shows an exemplary digital depletion assay using microwells as digital units.
Figure 38B:
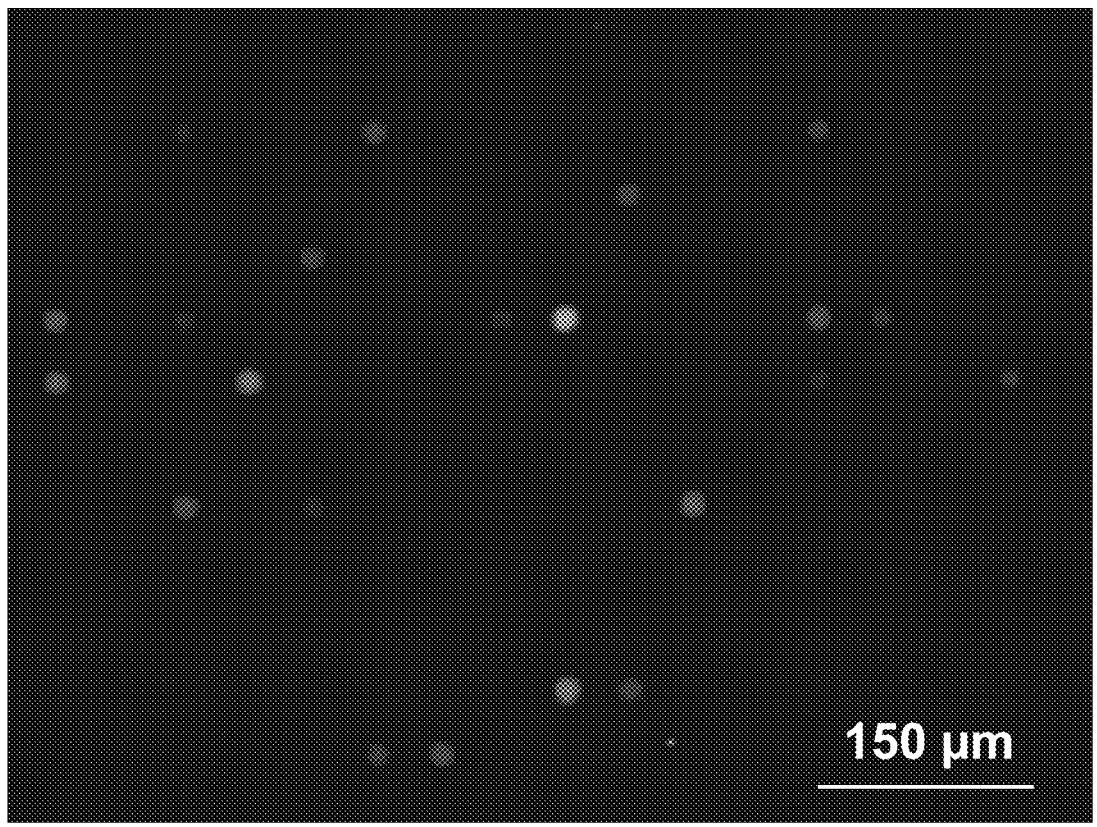
FIG. 38B shows an exemplary fluorescent image of positive and negative digital units.
Figure 38C:
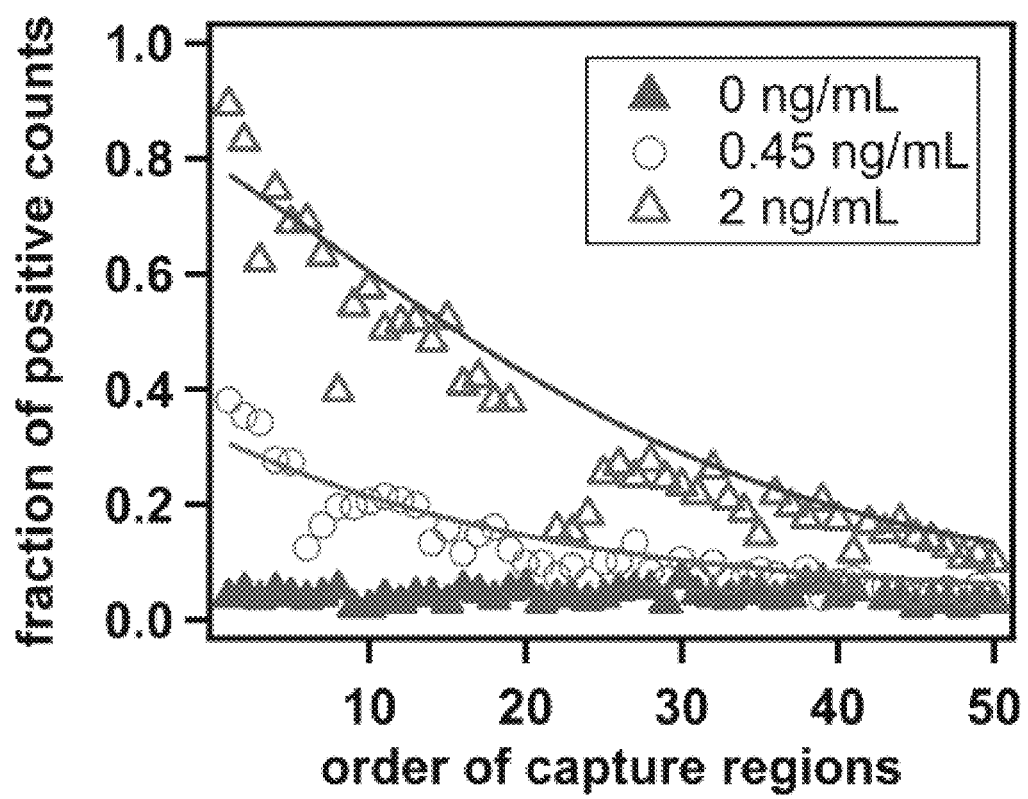
FIG. 38C shows exemplary experimental depletion curves for samples comprising zero nanograms per milliliter (ng/mL) (solid triangles), 0.45 ng/mL (empty circles), and 2 ng/mL (empty triangles) of GFAP.

An assay can comprise a depletion assay, wherein a sample comprising analytes contacts a series of digital units or capture regions. As the sample contacts subsequent digital units or capture regions, analytes can be captured from the sample and thereby depleted from the sample. A capture region can be classified as positive when a threshold number of digital units in that capture region are positive. Multiple thresholds can be used in analyzing the same assay results, which can improve the dynamic range of the assay, for example as described in Example 23. Example scheme of depletion assays are shown in FIG. 22A, FIG. 23, FIG. 24, and FIG. 25. Sample can be introduced to a series of capture regions, and the concentration or amount of analyte in the sample can determine the number of capture regions generating a positive signal. The depletion of analytes from the sample can be measured or characterized, for example by depletion curves showing the change in analyte number or concentration over successive digital units or capture regions. FIG. 29, for example, shows a simulation of depletion curves generated for a system comprising 15 depletion regions, each depletion region comprising 24 digital units (or patches); the number of positive digital units (or patches) per capture region is shown as a function of capture region number, for initial analyte concentrations of 1000 picomolar (pM), 500 pM, 250 pM, 125 pM, 62.5 pM, 31.25 pM, 15.63 pM, 7.81 pM, 3.91 pM, 1.95 pM, 0.97 pM, and 0.30 pM, in order from right to left on the figure. FIG. 36 shows experimental depletion curves for different concentrations of glial fibrillary acidic protein (GFAP), which can be used to diagnose traumatic brain injury (TBI); samples comprised various concentrations (0 pM, 0.1 pM, 1 pM, 10 pM, and 100 pM) of GFAP added to pooled human serum diluted with TPBS, using beads as digital units. FIG. 37 shows experimental depletion curves for different concentrations of p24, which can be used to diagnose HIV; samples comprised various concentrations (0 pM, 0.020 pM, 0.49 pM, 12 pM, and 310 pM) of p24 added to pooled human serum diluted with TPBS, using wells as digital units. FIG. 38 shows a digital depletion assay of GFAP using microwells as digital units. FIG. 38A shows a device comprising microwells with surface-immobilized capture agents. FIG. 38B shows a fluorescent image of positive and negative digital units. FIG. 38C shows depletion curves for samples comprising 0 ng/mL, 0.45 ng/mL, and 2 ng/mL of GFAP.

In some cases, the relationship between the number of positive capture regions and the concentration or amount of analyte can be linear or about linear. For example, a doubling in the concentration or amount of analyte can result in twice or about twice as many capture regions being classified as positive. In some cases, the relationship between the number of positive capture regions and the concentration or amount of analyte can be logarithmic or about logarithmic. For example, a doubling in the concentration or amount of analyte can result in one or about one additional capture region being classified as positive. In another example, to deplete $10^2$, $10^3$, $10^4$, and $10^5$ femtomolar (fM) analyte, the digital depletion assay can take 2, 4, 8.5, and 12 capture regions respectively, as shown in FIG. 34C. A logarithmic relationship can be achieved by providing an excess of digital units to prevent saturation of the assay or of individual capture regions with analytes.

In some cases, the concentration or amount of analyte can be measured by analyzing the signal from digital units in negative capture regions. For example, a sample introduced to a series of capture regions may be too low in concentration to cause even the first capture region to be classified as positive, but can still cause some digital units in that capture region to become positive; analysis of the positive digital units can be used to measure the concentration or amount of analyte. In another example, a sample introduced to a series of capture regions can result in some capture regions being classified as positive; the number of positive digital units in the first negative capture region or in the first few negative capture regions can still be used to measure the concentration or amount of analyte with more precision or detail than by using the number of positive capture regions only.

Figure 30:
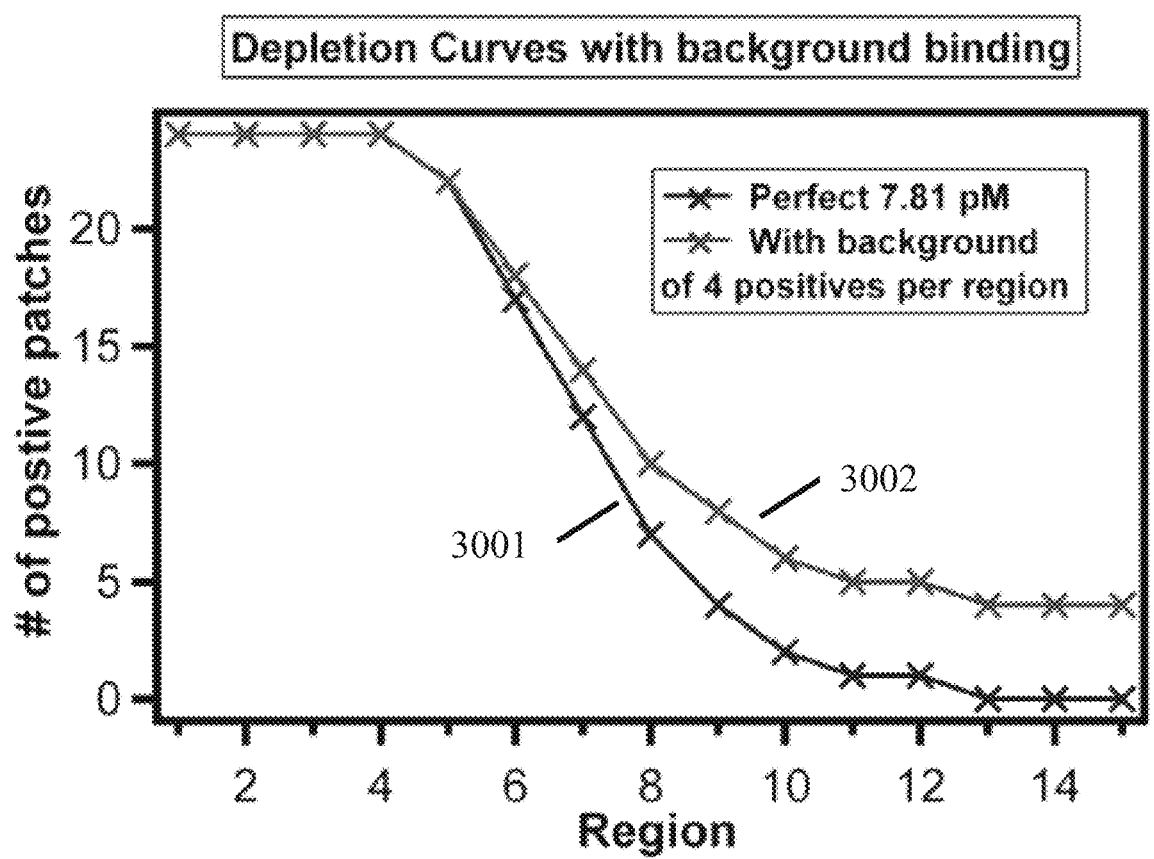
FIG. 30 shows exemplary simulated depletion curves with and without background positive signal.
Figure 31A:
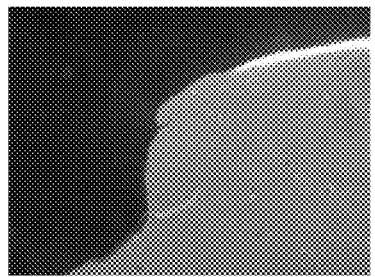
FIG. 31A shows exemplary fluorescent hydrogel for signal generation by quenching.
Figure 31B:
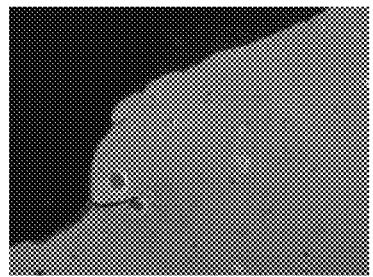
FIG. 31B shows exemplary fluorescent hydrogel for signal generation by quenching, after addition of one molar (1 M) of $H_2O_2$.
Figure 31C:
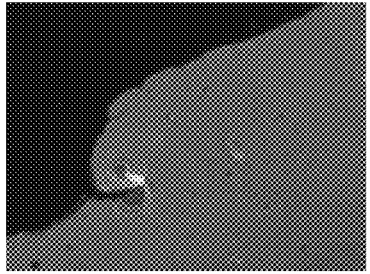
FIG. 31C shows exemplary fluorescent hydrogel for signal generation by quenching, after addition of catalase.
Figure 31D:
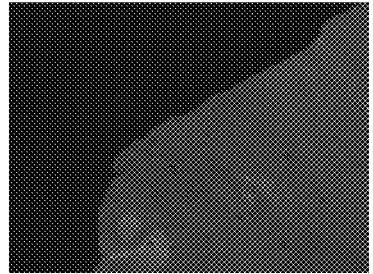
FIG. 31D shows exemplary fluorescent hydrogel for signal generation by quenching, after addition of triton X100.

Background signal can be generated by background levels of binding, such as non-specific binding. Background signal levels can be determined and calibrated for. The level of signal, such as the number of positive digital units, in capture regions downstream of the depletion zone can be measured and used as the background value. FIG. 30 shows a simulation of depletion without background nonspecific binding 3001 and with background nonspecific binding 3002 for a 7.81 pM sample, background can be measured and calibrated for. This can allow reduction or elimination of error from background signal. Calibration for background signal can improve the sensitivity of the assay.

Signal

The present disclosure provides for signal generation and analysis. Prior to signal generation, digital units can be washed. Washing can remove unbound or non-specifically bound labels, reagents, biproducts, contaminants, or other material. Sometimes, prior to signal generation, digital units can be neutralized. Neutralization can remove unbound or non-specifically bound labels, reagents, bi-products, contaminants, or other material.

A binary signal (e.g., positive/negative, yes/no, on/off) can be produced from digital units in response to the presence or absence of analytes. Turn-on signals and turn-off signals can both be used; turn-off signals can be mathematically converted to turn-on signals and handled in a similar manner to turn-on signals. Classification of a digital unit can depend upon whether the signal from that digital unit exceeds a baseline or threshold value. Classification of a digital unit can depend upon whether the signal from that digital unit goes below a baseline or threshold value. The baseline value can be a predetermined value. The baseline value can be determined based on comparison to a reference digital unit or set of digital units.

Generation of a positive signal from a digital unit can depend on the number or concentration of analytes captured, trapped, or bound by that digital unit. In some cases, a threshold number of analytes captured, trapped, or bound by a digital unit allows a positive signal to be generated from that digital unit. For example, FIG. 8 shows signal being generated from a digital unit with two captured analytes but not from a digital unit with only one captured analyte. The threshold number of analytes to allow positive signal generation can be at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more analytes. The threshold number of analytes to allow positive signal generation can be at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, the threshold number of analytes to allow positive signal generation can be from 1 to 19 analytes. In some cases, the threshold number of analytes to allow positive signal generation can be from 2 to 19 analytes. In some cases, the threshold number of analytes to allow positive signal generation can be from 3 to 19 analytes. In some cases, the threshold number of analytes to allow positive signal generation can be from 4 to 19 analytes. In some cases, the threshold number of analytes to allow positive signal generation can be from 5 to 19 analytes. In some cases, the threshold number of analytes to allow positive signal generation can be from 6 to 19 analytes. In some cases, the threshold number of analytes to allow positive signal generation can be from 7 to 19 analytes. In some cases, the threshold number of analytes to allow positive signal generation can be from 8 to 19 analytes. In some cases, the threshold number of analytes to allow positive signal generation can be from 9 to 19 analytes. In some cases, the threshold number of analytes to allow positive signal generation can be from 10 to 19 analytes. In some cases, a threshold concentration of analytes captured, trapped, or bound by a digital unit allows a positive signal to be generated from that digital unit. The threshold concentration of analytes to allow positive signal generation can be at least about zero zeptomolar (zM), 1 zM, 10 zM, 100 zM, 1 attomolar (aM), 10 aM, 100 aM, 1 femtomolar (fM), 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or more. The threshold concentration of analytes to allow positive signal generation can be at most about 1, fM, 10 fM, 100 fM, 1 pM, 10 pM, 100 pM, 1 nM, 10 nM, 100 nM, 1 µM, 10 µM, 100 µM, 1 mM, 10 mM, 100 mM, 1 M, or less. The threshold number or concentration of analytes to allow positive signal generation from a digital unit can be controlled. Inhibitors can be used with digital units to control the threshold number or concentration. For example, the number or concentration of analytes can be required to be higher than the number or concentration of inhibitors in a digital unit in order for a signal to be produced from that digital unit. FIG. 43 shows an example of an enzyme and an inhibitor for producing a colorimetric signal. FIG. 43A shows how, when its concentration overcomes the threshold concentration of syn-(S)-TZ2PIQ inhibitor, acetylcholinesterase (AChE) can convert acetylcholine to thiocholine, reducing a purple suspension of $I_3^-$/starch complex to a clear mixture. FIG. 43B shows parameters relating to the amount by which the threshold concentration is exceeded and the amount of signal output. FIG. 43C shows the increase in relative signal output as the threshold concentration is exceeded. FIG. 43D shows on (clear) and off (dark) digital units (e.g., wells).

In some cases, the probability of a positive signal being generated from a digital unit depends on the number or concentration of analytes captured, trapped, or bound by that digital unit. The probability of a positive signal being generated from a digital unit can be controlled. For example, the efficiency of a signal generating reaction can be controlled, thereby controlling the probability of signal generation; a lower efficiency reaction can result in a lower probability of signal generation for a given number or concentration of analytes.

Figure 42A:
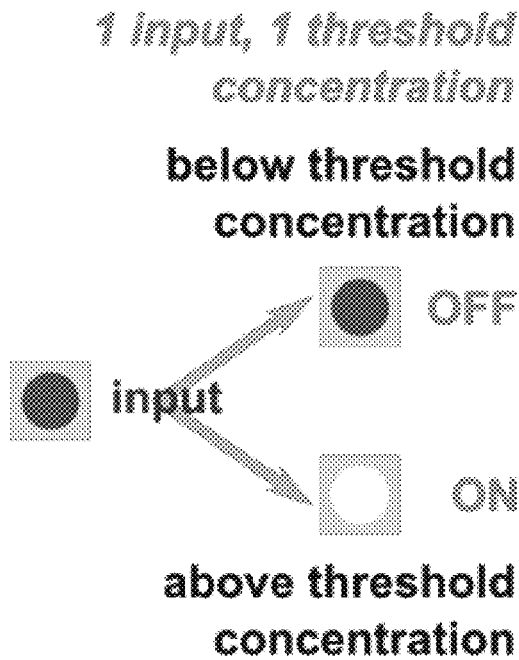
FIG. 42A shows an exemplary schematic of a threshold-based digital signal response.
Figure 42B:
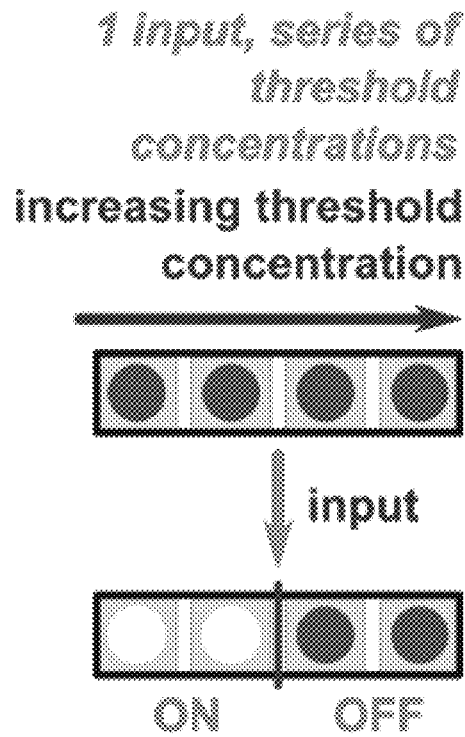
FIG. 42B shows an exemplary schematic of threshold-based digital signal response in a set of digital units with increasing thresholds.
Figure 42C:
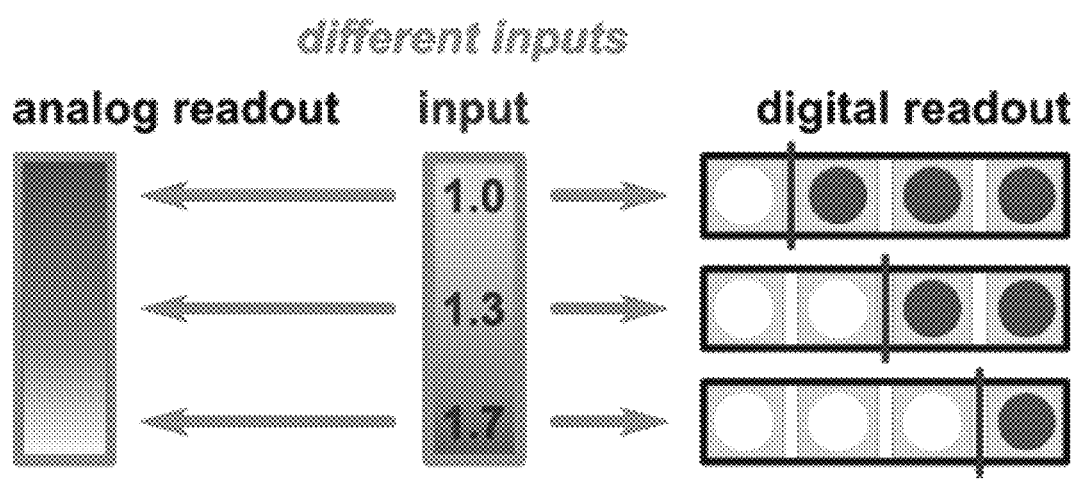
FIG. 42C shows an exemplary schematic of different input analyte concentrations resulting in different numbers of positive digital units on a digital readout with increasing thresholds.
Figure 44A:
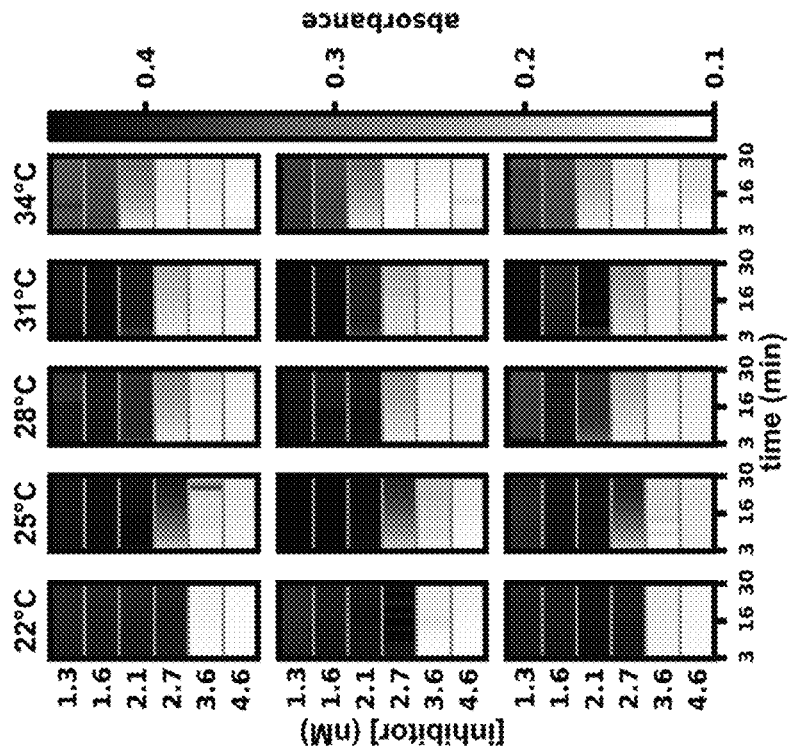
FIG. 44A shows exemplary false color maps demonstrating the robustness of threshold chemistry at different temperatures and readout times.
Figure 44B:
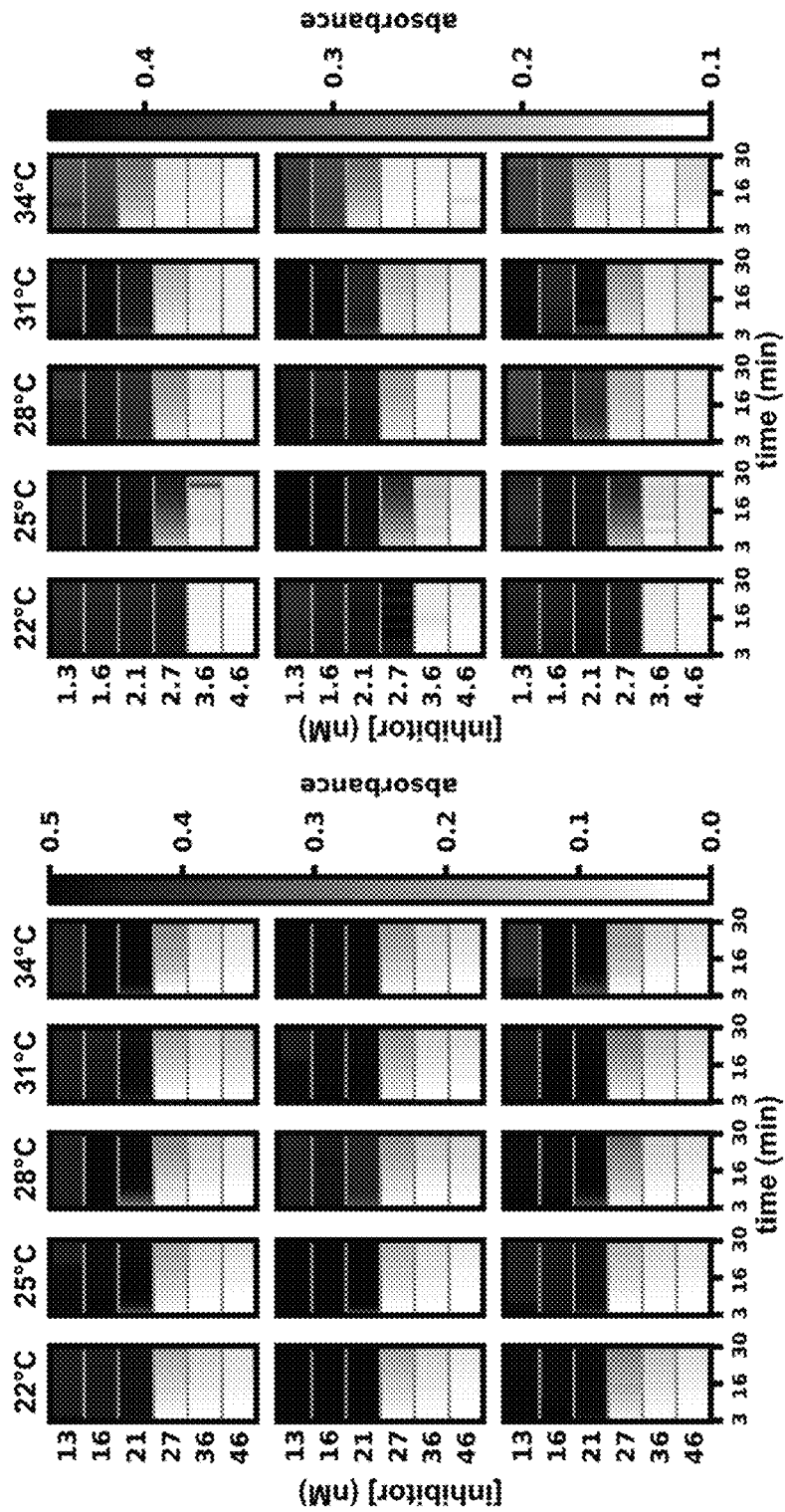
FIG. 44B shows exemplary false color maps demonstrating the robustness of threshold chemistry at different temperatures and readout times.
Figure 45:
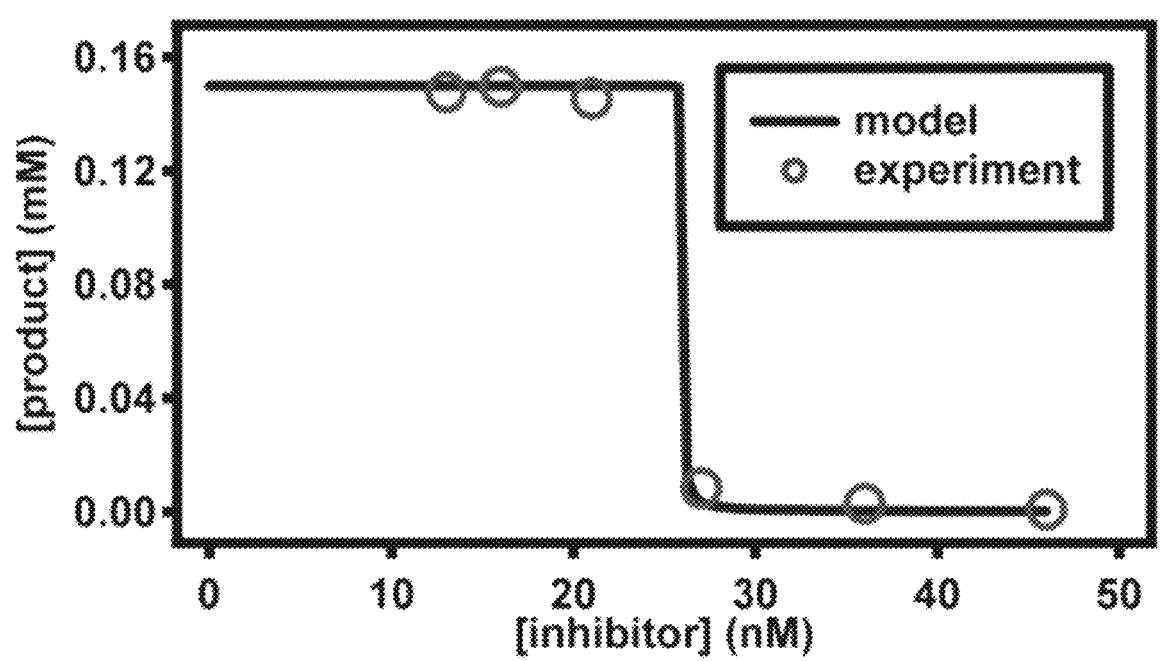
FIG. 45 shows an exemplary graph comparing model (line) and experimental (circles) results for signal generation versus inhibitor concentration.
Figure 47A:
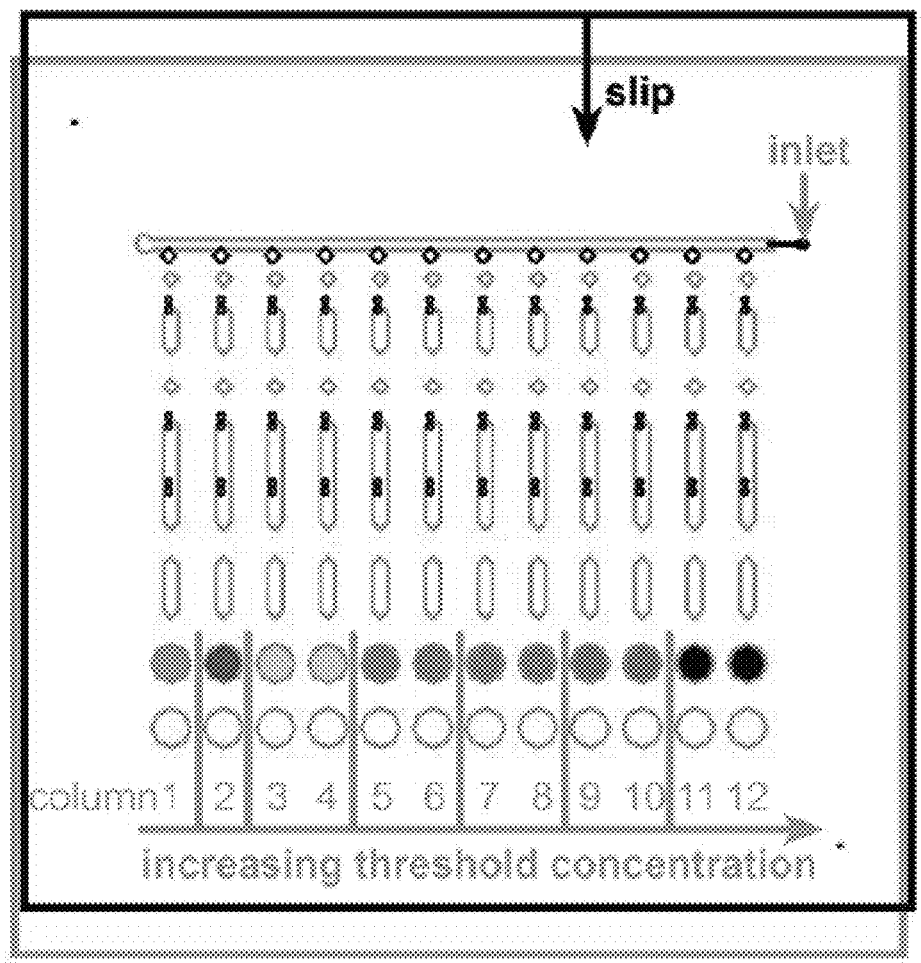
FIG. 47A shows an exemplary schematic of the arrangement of threshold concentrations on an assay device.
Figure 47B:
FIG. 47B shows exemplary photographs of an on to off transition for analysis.
Figures 48A, 48B:
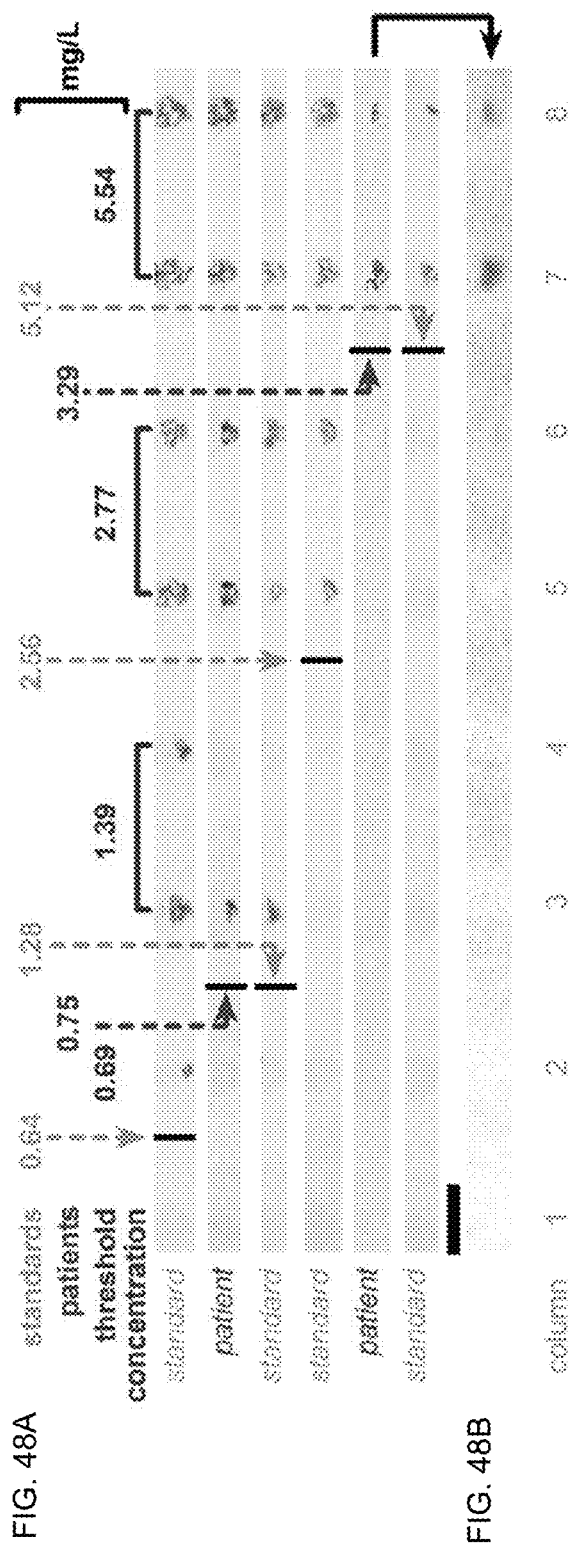
FIG. 48A shows exemplary photographs of assay results with multiple thresholds.
FIG. 48B shows an exemplary photograph of an assay result with multiple thresholds.

Different digital units can have the same threshold number, threshold concentration, or positive signal generation probability. Different digital units can have different threshold numbers, threshold concentrations, or positive signal generation probabilities. Digital units arranged into a given capture region or subset can have the same or different threshold number, threshold concentration, or positive signal generation probability. The use of digital units with different threshold numbers, threshold concentrations, or positive signal generation probabilities can provide a large dynamic range for the measurement of analyte number or concentration. For example, the threshold number or threshold concentration between digital units can be at least about 1, 2, 3, 4, 5, 6, 7, 8, 9, 10, 11, 12, 13, 14, 15, 16, 17, 18, 19, or 20 orders of magnitude. The use of digital units with different threshold numbers, threshold concentrations, or positive signal generation probabilities can allow for analog-to-digital conversion of an analyte number or concentration. For example, FIG. 42 shows an example of analog to digital conversion of concentration information. FIG. 42A shows an input analyte concentration which can generate a signal from a digital unit if it is above a threshold concentration. FIG. 42B shows a series of digital units with increasing threshold concentrations. FIG. 42C shows how different analog analyte concentration inputs can yield different digital readouts from the digital units, based on the thresholds. Mechanisms for generating a threshold response are further described in Patent Application Nos. PCT/US2008/071374, PCT/US07/02532, and PCT/US08/71370, each of which is hereby incorporated by reference in its entirety.

Figure 7A:
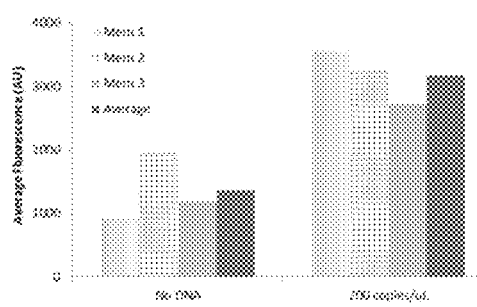
FIG. 7A shows an exemplary average fluorescence after PCR for three membranes to which was applied amplification mix containing either 200 or 0 copies of lambda phage DNA.
Figure 7B:
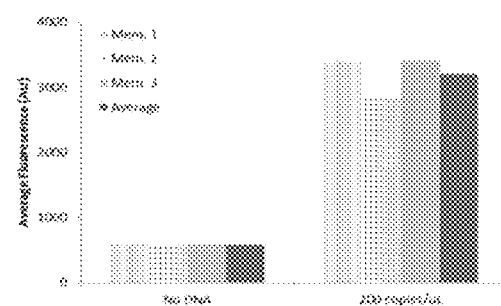
FIG. 7B shows an exemplary average fluorescence after LAMP for three membranes to which was applied amplification mix containing either 200 or zero copies of lambda phage DNA.

Dynamic range can be increased, for example in the devices in FIG. 4-6, by providing two measures of the concentration of a sample. The first measure can be the total number of digital units that generate a positive signal in each capture region, or it can be the total intensity of each capture region. The second measure can be the signal intensity or number of positive digital units in each capture region along the direction of flow. The analyte can depleted as it flows along or through the digital units, such that the number of digital units or capture regions that give a positive signal is related to the concentration of the analyte. A sample with initial high concentration of analyte can require a larger number of regions to deplete analyte from the sample, such that the first regions would saturate (FIG. 7). In the case of a device with expanding geometry, such as that seen in FIG. 6, the depletion curve can also be dependent on the binding affinity of the analyte, but the amount of digital units or capture regions required to deplete the sample would still be related to the concentration of the analyte. For low concentration analytes, the sample can deplete rapidly and the concentration of analyte in the sample could be related to the digital signal or signal intensity, while for a high concentration of analyte the sample can deplete more slowly and the concentration could be determined from where the bound concentration of analyte began to drop.

Signal generation can be conducted by a variety of methods, including but not limited to amplification reactions (e.g., PCR), sequencing or sequence determination, genotyping, hybridization, immunoassay (e.g. ELISA), antibody labeling, nucleic acid labeling, aptamer labeling, protein labeling, peptide labeling, protein mimic labeling, fluorescent labeling, metal labeling (e.g., gold or silver), Aldol® dyes (Biosynth®), colorimetric reactions, enzymatic reactions, contrast agent labeling, beads, and combinations thereof. The signal from digital units can be chosen from a range of signal used to detect progress of reactions, including but not limited to electrochemical signal, optical signal (e.g., fluorescence signal), chemiluminescence signal, lateral flow strips, and the generation of a heterogeneous substance (e.g., precipitation, air bubble).

Amplification reaction can include polymerase chain reaction (PCR), nucleic acid sequence based amplification (NASBA), self sustained sequence replication (3SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR or ligation mediated PCR. Amplification or detection methods for nucleic acids can include but are not limited to PCR, RT-PCR, or other methods including isothermal amplification methods. Isothermal nucleic acid amplification methods can include but are not limited to strand displacement amplification (SDA), transcription mediated amplification, nucleic acid sequence based amplification (NASBA), recombinase polymerase amplification (RPA), rolling circle amplification, ramification amplification, helicase-dependent isothermal DNA amplification, loop mediated isothermal amplification (LAMP), methods based on both signal amplification and target amplification such as branched-DNA-based detection methodologies, hybridization chain reaction, or nucleic acid-based logic gates and DNA circuits (e.g., [Qian and Winfree, Scaling Up Digital Circuit Computation with DNA Strand Displacement Cascades, Science 2011; 6034: 1196-1201]).

Sequencing, or sequence determination techniques, can be performed by using Sanger sequencing, Illumina (Solexa) sequencing, pyrosequencing, next generation sequencing, maxam-gilbert sequencing, chain termination methods, shotgun sequencing, bridge PCR. Next generation sequencing methodologies may comprise Massively parallel signature sequencing, Polony sequencing, SOLiD sequencing, Ion Torrent semiconductor sequencing, DNA nanoball sequencing, Heliscope single molecule sequencing, Single molecule real time (SMRT) sequencing, Nanopore DNA sequencing, Tunnelling currents DNA sequencing, Sequencing by hybridization, Sequencing with mass spectrometry, Microfluidic Sanger sequencing, Microscopy-based techniques, RNA Polymerase sequencing or In vitro virus high-throughput sequencing.

Immunoassay techniques include enzyme multiplied immunoassay technique (EMIT), enzyme-linked immunosorbent assay (ELISA), sandwich ELISA, competitive ELISA, IgM antibody capture ELISA (MAC ELISA), microparticle enzyme immunoassay (MEIA), capillary electrophoresis immunoassays (CEIA); radioimmunoassays (RIA), immunoradiometric assays (IRMA), fluorescence polarization immunoassays (FPIA), or chemiluminescence assays (CL).

Signal can be detected by a variety of techniques, including but not limited to optical techniques, electrical techniques or magnetic techniques. The signal can be optically detectable, for example fluorescent signal, phosphorescent signal, colorimetric signal, absorption signal, or scattering signal. For example, FIG. 38B shows a fluorescent image of positive and negative signals from digital units. The signal can be electromagnetic. The signal can comprise the presence or absence of a physical object, such as a bead. Captured analytes can be labeled with a fluorescent agent or a contrast agent. Analytes can be labeled with enzymes which can produce a fluorescent signal. Analytes can be labeled with enzymes which can produce a color change in a substrate, producing a colorimetric signal. In some cases, signal can be generated from reporter molecules that are bound to affinity molecules and applied to digital units to bind to captured analyte. In some cases, signal can be generated from molecules with reporter moieties and affinity moieties that are applied to digital units to bind to captured analyte. The reporter molecule or reporter moiety can be fluorescent. The digital units or capture regions can be washed to remove unbound reporter. In some cases, the reporter molecule can be calcein or calcein with cetyl trimethyl ammonium bromide (calcein-CTAB). In some cases, the reporter can be an intercalating dye. The intercalating dye can be berberine, ethidium bromide, proflavine, daunomycin, doxorubicin, thalidomide, YOYO-1, SYBR Green I, SYBR Green II, oxazole yellow (YO), thiazole orange (TO), PicoGreen (PG), and/or other dyes. Analytes can be labeled with enzymes which can produce an electrical signal, for example by electro-activating a substrate molecule which can be oxidized and reduced. Labeling can occur by binding with an affinity agent, for example as in a sandwich assay. Labeling can occur by intercalating dyes.

Signal can be generated by quenching an existing signal, such as a fluorescent or phosphorescence signal. For example, a gel material such as a hydrogel or and organogel can comprise chromophores, fluorophores, or materials emitting phosphorescence; as well as analyte binding agents. Oxygen-responsive chromophores, fluorophores, or materials emitting phosphorescence can be quenched by oxygen generated in the presence of an analyte. Analyte can be captured and labeled with catalysts or enzymes capable of producing oxygen. Generation of oxygen can quench the color, fluorescent or phosphorescence signal, with such quenching serving as signal for the presence of the analyte.

For example, FIG. 31 shows fluorescence in a hydrogel prepared by UV polymerization of a mixture of 700 µL of 2-hydroxyethyl methacrylate (HEMA), 21.8 µL ethylene glycol diacrylate (EGDA), 500 µL of 10 mg/ml solution of Tris(4,7-diphenyl-1,10-phenanthroline)ruthenium(II) dichloride (TDPR) complex in THF, and 300 µL and 20 mg of 2,2'-dimethylphenyl acetophenone (DMPA). FIG. 31A shows fluorescence at the edge of the hydrogel film directly after polymerization. FIG. 31B shows a slight decrease in fluorescence 3 to 5 minutes after the addition of a droplet containing 1 M $H_2O_2$. FIG. 31C shows a slight further decrease in fluorescence after addition of catalase to a concentration of 0.1 nM. FIG. 31D shows a larger decrease in fluorescence after addition of hexadecane saturated with triton 100×. Multiple linked fluorophores can be used to create color change by quenching. For example, two linked fluorophores can have overlapping emission and absorption spectra such that they can engage in FRET. One fluorophore can be quenched by oxygen, such that the FRET efficiency is changed by the presence of oxygen, resulting in a change in fluorescent wavelength and/or fluorescent lifetime.

Signal strength can be amplified. Signal amplification can occur by amplification of the signal or by amplification of signal generating molecules. For some analytes (e.g. nucleic acids), signal amplification can occur by amplification of the analyte, or by a combination of amplification of the signal, amplification of the signal generating molecule, and amplification of the analyte. In some cases, amplification of the analyte can occur by PCR. PCR can comprise standard PCR, digital PCR, hot start PCR, isothermal PCR, multiplex PCR, nested PCR, quantitative PCR (qPCR), reverse transcription PCR (RT-PCR), solid phase PCR, touchdown PCR, and/or other varieties of PCR. In some cases, amplification of the analyte can occur by helicase-dependent amplification (HDA). In some cases, amplification of the analyte can occur by recombinase polymerase amplification (RPA). In some cases, amplification of the analyte can occur by loop-mediated isothermal amplification (LAMP). LAMP can comprise standard LAMP, real-time LAMP (RT-LAMP), and/or other varieties of LAMP.

Prior to signal generation, digital units or capture regions can be compartmentalized or segregated from each other. Compartmentalization can reduce or prevent crosstalk or diffusion of signal between digital units or capture regions. Digital units or capture regions can be compartmentalized in a number of ways including, but not limited to, adding an immiscible fluid to break up diffusible communication among digital units or capture regions (e.g. covering microwells with oil, separating pillars with oil by displacing aqueous solution, aqueous two phase separated fluids such as PEG/Dextran), phase change such as de-swelling (induced by pH, temperature, ionic strength, addition of specific agents such as divalent metal ions, or other methods), spontaneous compartmentalization achieved by restricting diffusion (e.g. as in dense gels through which nucleic acids do not readily diffuse (e.g., polony PCR or RCA blobs), or by use of capture agents to bind and slow diffusion), and partitioning with walls. For example, FIG. 22A shows compartmentalization of digital units with an immiscible oil phase after capture of target analyte. The oil can comprise a carbohydrate, a fluorocarbon, or an aromatic moiety.

Figure 49A:
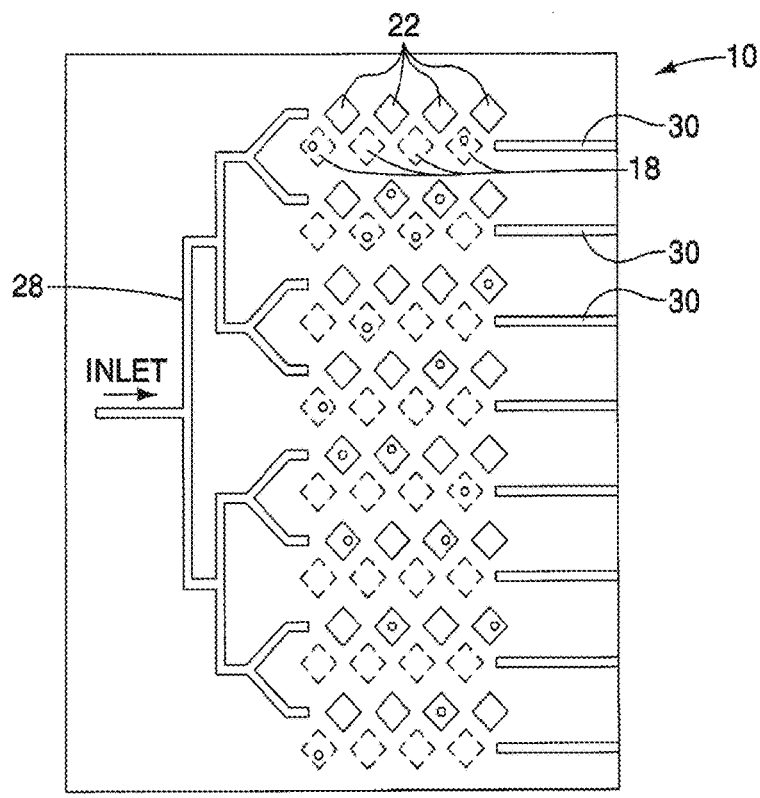
FIG. 49A is a top view of a slip chip device according to another embodiment of the invention in a first position
Figure 49B:
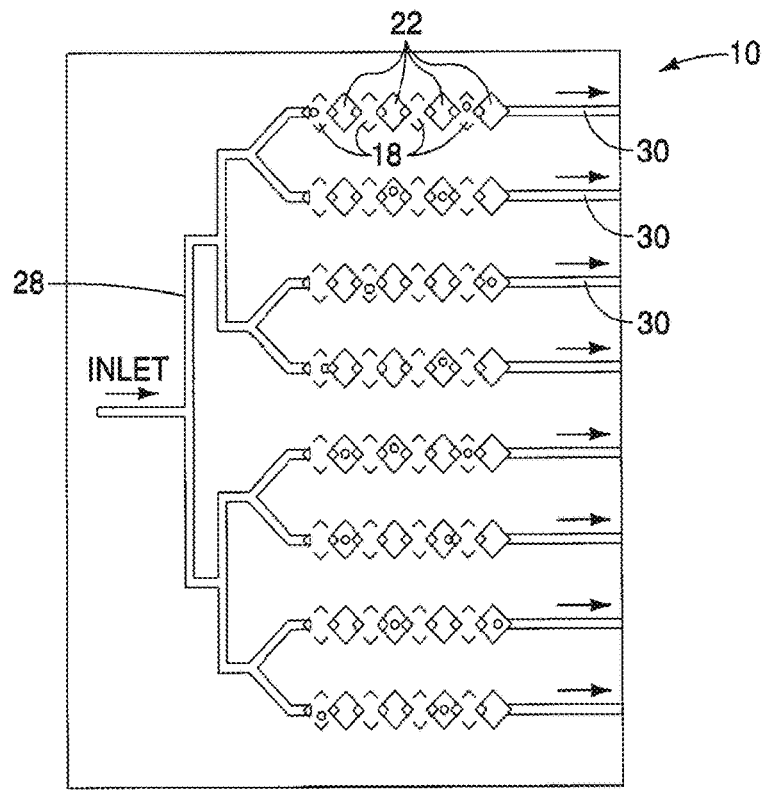
FIG. 49B is a top view of the slip chip device shown in FIG. 49A in a second position.

Compartmentalization can be conducted by physical motion of digital units or capture regions. The compartmentalization can be conducted by physical displacement of digital units or capture regions. The movement or displacement can be manually or electronically controlled. For example, digital units or capture regions can be moved to no longer be in fluidic communication with each other, such as by the actuation of a device (e.g., a SlipChip device, as described for example in U.S. patent application Ser. No. 13/257,811 or in PCT Application No. PCT/US2010/028361, each of which is hereby incorporated by reference in its entirety). As described in U.S. patent application Ser. No. 13/257,811 (i.e., U.S. Publication No. 2012/0028342 at Paragraphs [0107] and [0108]: In some embodiments, as shown in FIG. 49A and FIG. 49B the device comprises first and second areas [i.e., first and second digital units] 18, 22, with first areas formed within the first surface [i.e., first capture region] 16, and second areas formed within the second surface [i.e., second capture region] 20. The first and second surface are opposed to one another and can move relative to the other from a first position to a second position. The device 10 includes an inlet duct [i.e., an inlet] 28 formed along the second surface 20, and multiple outlet ducts [i.e., fluid receiving structures] 30 formed along the first surface 16. In the position shown in FIG. 49B, the first areas 18 and second areas 22 overlap to form a continuous flow path along the first and second areas 18, 22 connecting the inlet 28 and the fluid receiving structure 30. In the position shown in FIG. 49A, the first areas 18 and second areas 22 are isolated. The first and second surfaces are configured to slip relative to each other to move between the positions shown in FIG. 49A and FIG. 49B. Compartmentalization can be conducted by introduction of an isolation fluid. The isolation fluid can be immiscible with the sample fluid. The isolation fluid can prevent or reduce transport of analyte between digital units or capture regions. In some cases, the isolation fluid does not substantially enter the digital units. In some cases, the isolation fluid does not preferentially wet the digital units. In some cases, the device comprises a pattern (e.g., a surface pattern or a three-dimensional pattern) of regions that are wettable and non-wettable by the isolation fluid, which can cause the fluid to be preferentially maintained by the wettable parts of the pattern. Compartmentalization can be achieved by implementation of different hydrodynamic resistances. Digital units or capture regions can be initially in fluid communication with each other and compartmentalized during the assay, can be initially compartmentalized prior to conducting the assay, or can remain in fluid communication throughout the assay. Digital units or capture regions can be arranged in series, such that they are composed of smaller stacked elements which can be separated after the completion of the assay (e.g. FIG. 1). Compartmentalization can also be conducted by virtually dividing a substrate into capture regions or digital units, or a capture region into digital units, in the absence of physical separation. Signal can be generated while the analyte remains captured by the digital unit (e.g., FIG. 8B, FIG. 9B, FIG. 10B), or can be generated from analyte eluted or transferred into post-capture analysis units (e.g., FIG. 8A, FIG. 9A, FIG. 10A). Post-capture analysis units can comprise any structures or configurations described for digital units, and can be analyzed in the same ways. Analyte from a single digital unit can be transferred into a single post-capture analysis unit (e.g., FIG. 8) or into multiple post-capture analysis units (e.g., FIG. 9, FIG. 10).

In some cases, non-Brownian, non-diffusive or poorly diffusive chemistries can be used to reduce or prevent crosstalk or diffusion of signal between digital units or capture regions in a similar manner to compartmentalization. In some manifestations, Aldol® dyes (Biosynth®) partition preferentially into the digital units or capture regions (e.g., Spitz et al, "A Novel Indicator Platform." US 20120058503 A1). In some manifestations, gold or silver amplification of gold nanoparticles is employed (Method of detection by enhancement of silver staining, US 20040101889 A1, Letsinger.). In some cases, soluble metals can be deposited in the digital units or capture regions by reduction (e.g., enzymatic or chemical) (Moller et al. "Enzymatic Control of Metal deposition as Key Step for a Low-Background Electrical Detection for DNA Chips." Nano Letters (2005), Vol 5, No 7, 1475-1482. Bieniarz et al, "Enzyme-catalyzed metal deposition for the enhanced detection of analytes of interest." U.S. Pat. No. 7,642,064 B2. Hainfeld et al, "Site-Specific Enzymatic Deposition of Metal In Situ." US 20080213783. Powell et al, "Methods and reagents to increase the sensitivity of enzyme metallographic detection." US 20080318249. Bieniarz et al, "Enzyme-catalyzed metal deposition for the enhanced detection of analytes of interest." U.S. Pat. No. 8,329,401). In some cases, bubbles can be generated from a trigger, such as but not limited to vacuum, catalyst, chemical reaction, enzyme, or any combination thereof. In some manifestations, oxygen may be used to quench fluorescence. In some examples, the size of bubbles are at least 0.5, 1, 1.5, 2, 4, 6, 8, 10, 20, 30, 40, 50, 60, 70, 80, 90, 100, 120, 140, 160, 180, 200, 400, 600, 800, 1000 nanometers or more. In some examples, the size of bubbles are at most 1, 1.5, 2, 4, 6, 8, 10, 20, 30, 40, 50, 60, 70, 80, 90, 100, 120, 140, 160, 180, 200, 400, 600, 800, 1000 nanometers or less.

Figure 32:
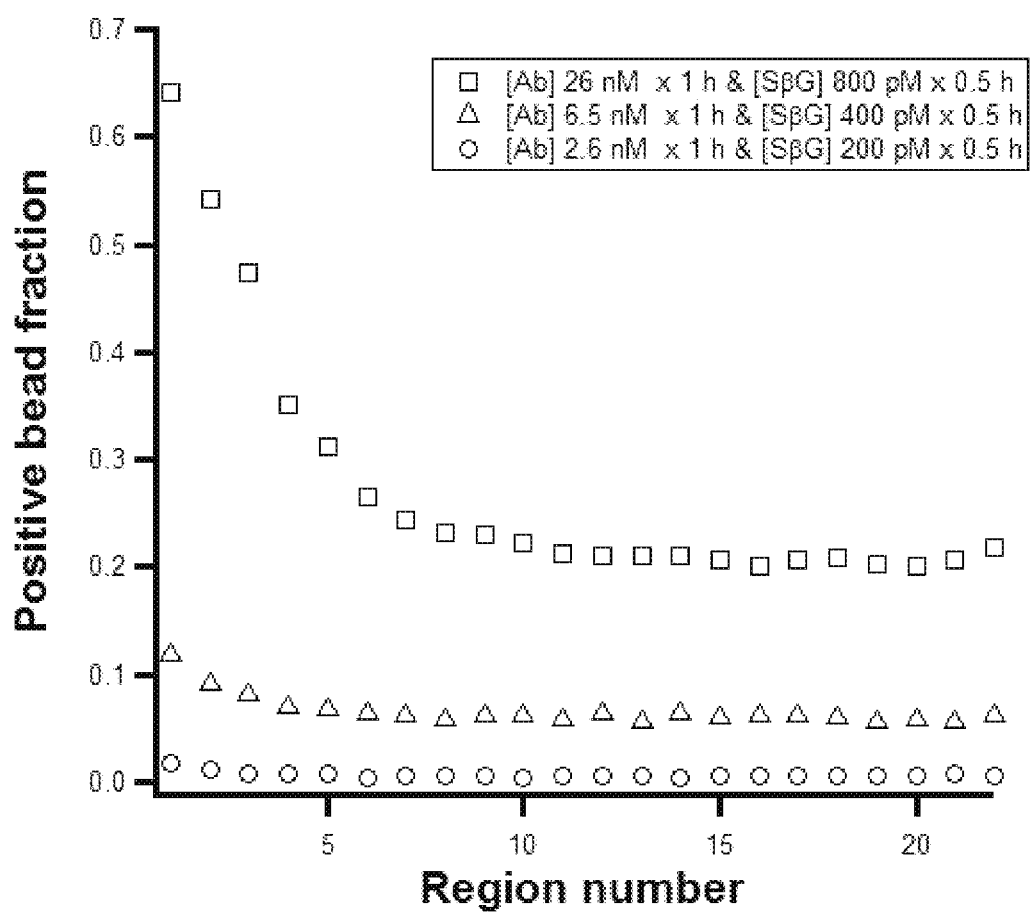
FIG. 32 shows exemplary experimental data comparing the effect on signal and background of labeling agent concentration.
Figure 33:
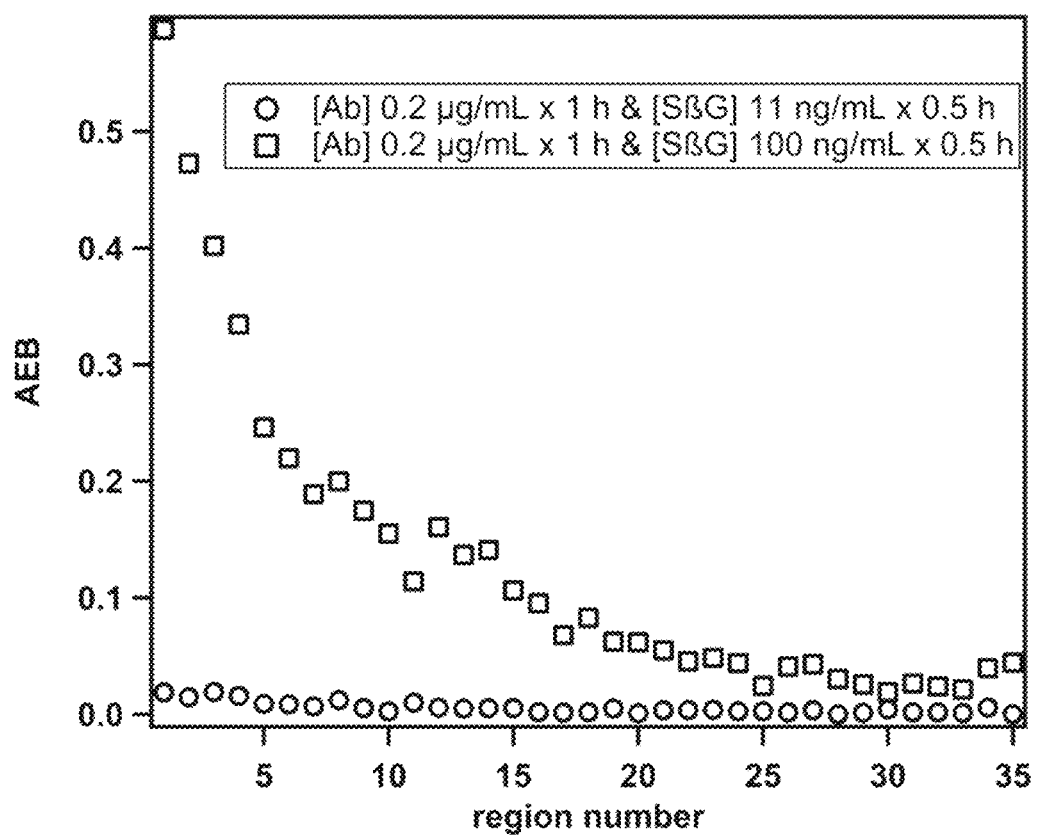
FIG. 33 shows exemplary experimental data comparing the effect on signal and background of labeling agent efficiency.

A background signal level can be determined and used for calibration. Background signal level can be pre-determined. Background signal level can be measured from digital units or capture regions without bound analyte. For example, in a depletion assay, the amount of analyte can be depleted from the sample by contact with digital units or capture regions; background signal can be determined from measuring digital units or capture regions which encounter sample fluid that is completely or substantially depleted of analyte such that the digital units or capture regions do not bind analyte. Background signal level can be affected by different assay conditions. Different concentrations of labeling agents (e.g., detection antibodies) can affect labeling efficiency of the analyte as well as the level of background signal. For example, as shown in FIG. 32, higher concentrations (e.g., square data points) of labeling agents (e.g., antibodies with streptavidin-conjugated beta-galactosidase) for the analyte (e.g., TNF-alpha) can result in higher positive digital unit (e.g. bead) fraction in both earlier capture regions as well as later, post-depletion zone capture regions. In another example, as shown in FIG. 33, increased labeling efficiency (e.g., square data points) can result in a higher average number of labeling agents (e.g., enzymes) per digital unit (e.g., bead) (or average enzymes per bead, AEB) in both earlier capture regions as well as later, post-depletion zone capture regions.

Signal generated from a digital unit can be binary, allowing that digital unit to be classified as positive (or on) versus negative (or off). A signal resulting in a digital unit being classified as positive can be referred to as a positive signal; a signal resulting in a digital unit being classified as negative can be referred to as a negative signal. Turn-on signals and turn-off signals can both be used; turn-off signals can be mathematically converted to turn-on signals and handled in a similar manner to turn-on signals. Classification of a digital unit can depend upon whether the signal from that digital unit exceeds a baseline or threshold value. Classification of a digital unit can depend upon whether the signal from that digital unit goes below a baseline or threshold value. The baseline value can be a predetermined value. The baseline value can be determined based on comparison to a reference digital unit or set of digital units. Capture regions or subsets of digital units can also be classified as positive or negative; such a classification can be based on the number or fraction of positive digital units in a given capture region or subset of digital units.

The number or concentration of analytes in a sample can be calculated based on the signal generated from the digital units. The number, location, type, or a combination thereof of positive digital units can be used to calculate the number or concentration of analytes in a sample. The number, location, type, or a combination thereof of positive capture regions can be used to calculate the number or concentration of analytes in a sample.

Figure 35B:
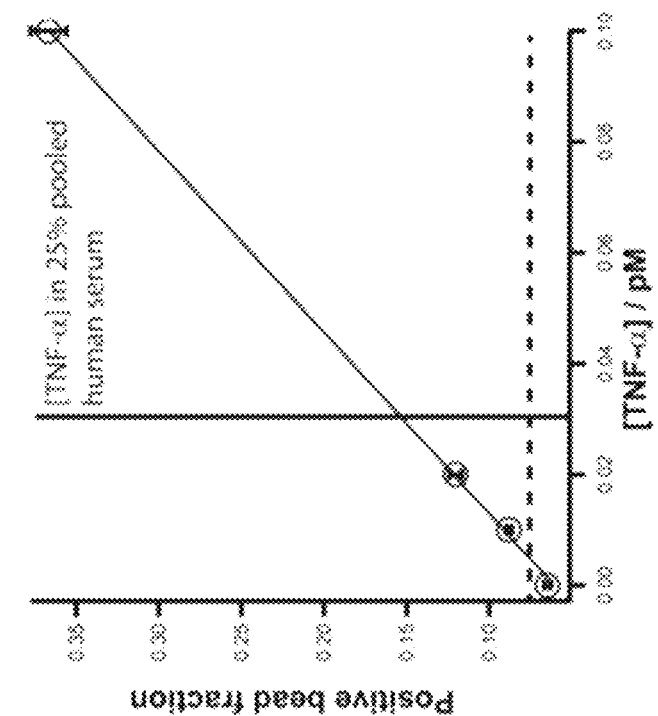
FIG. 35B shows an exemplary experimental lower concentration range of calibration curves with comparison to the concentration of TNF-alpha expected in 25% human serum.
Figure 35A:
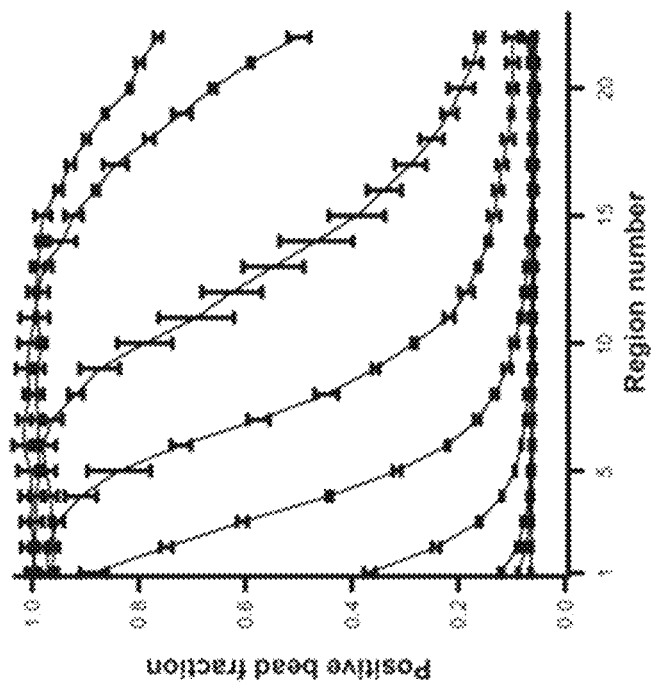
FIG. 35A shows exemplary experimental depletion curves for samples comprising, from bottom to top, zero picomolar (pM), 0.01 pM, 0.02 pM, 0.1 pM, 1 pM, 10 pM, 100 pM, 1000 pM, and 2000 pM of TNF-alpha, respectively.

Assay results can be determined by comparison of results to empirical correlations based on previous assays. For example, assays can be conducted using samples comprising known concentrations or amounts of analyte, and the results can be compiled to provide calibration information for future assays with unknown concentrations or amounts of analyte. Such results can comprise information about the number of positive digital units or capture regions, the identity of positive digital units or capture regions, the order or location of positive digital units or capture regions, or combinations thereof. For example, FIG. 34 shows experimental depletion curves for known concentrations of analyte (e.g., biotin-modified beta-galactosidase) captured by digital units (e.g., streptavidin coated beads). FIG. 34A shows a plot of the fraction of positive digital units per capture region for different analyte concentrations. FIG. 34B shows a plot of the fraction of positive digital units in the first capture region as a function of analyte concentration. FIG. 34C and FIG. 34D show the number of regions that deplete samples of different analyte concentrations, with a threshold for a positive capture region set at 0.8 fraction of positive digital units (FIG. 34C) and 0.07 fraction of positive digital units (FIG. 34D). FIG. 34E shows a logarithmic plot of the fraction of digital units (e.g., beads) with at least one captured analyte (e.g., enzyme) versus sample analyte concentration. In another example, FIG. 35 shows calibration and measurement of analyte (e.g. TNF-alpha) in a sample (e.g., 25% bovine serum), with all data are plotted as mean±standard deviation, n=3. FIG. 35A shows depletion curves for samples comprising, from bottom to top, zero picomolar (pM), 0.01 pM, 0.02 pM, 0.1 pM, 1 pM, 10 pM, 100 pM, 1000 pM, and 2000 pM of TNF-alpha, respectively. FIG. 35B shows the lower concentration range of calibration curves plotted, with comparison to the concentration of TNF-alpha expected in 25% human serum (0.03 pM; vertical line).

Assay results can be determined by comparison of results to theoretical models. For example, capture kinetics and Poisson distribution statistics can be used to analyze assay results. In some cases, a theoretical model divides a channel with the length of L (m) into a series of chambers on top of each capture region. Each capture region can be further divided into N digital units with a surface-bound capture reagent. A segment of the sample flow moving through the channel at the flow velocity of U (m/s) has a residence time within the chamber of t=L/U (s), and then moves forward to the next chamber of the channel. The Damköhler number (Da) can be used to characterize the analyte depletion in the flow within each region:

$$Da = \frac{\text{Rate of reaction}}{\text{Rate of convection}} = \frac{k_{on}[Ab] \cdot [Ag]V}{[Ag]Q} = k_{on}[Ab]t$$

where $k_{on}$ (M$^{-1}$·s$^{-1}$) is the binding rate, [Ab] (M) is the concentration of the active capture reagent (e.g., antibody), [Ag] (M) is the concentration of the analyte, V (L) is the volume of a chamber, and Q (L/s) is the volumetric flow rate, with desorption being negligible. If analyte is well-mixed in the channel and the capture reagent is in excess over the analyte, the capture efficiency for a region in a channel can be described as $1-e^{-Da}$, and $e^{-Da}$ can describe the fraction of analyte left in the flow and moved forward to the next capture region. As a result, the depletion curve can be described as $A_0(1-e^{-Da})e^{-(x-1)Da}$, where $A_0$ is the total initial number of copies of the analyte (M), and x is the order of the depletion region. Captured analyte $\theta_f$ (M) can be uniformly labeled with a labeling agent (e.g., detection antibody to form an immune sandwich complex), with labeling efficiency $L_f$. The labeling agent has a binding rate of $k_{on,1}$(M$^{-1}$·s$^{-1}$) and a concentration $L_0$, which can be in excess over the surface bound analyte. The labeling reaction can be can be described by the equation:

$$L(t) = \theta(1 - e^{-tk_{on,1}L_0})$$

The labeled analytes on the $x^{th}$ capture region $A_0L_f(1-e^{-Da})e^{-(x-1)Da}$ can statistically distribute into N digital units, which can be described by the Poisson distribution:

$$f(k;\lambda) = \frac{\lambda^k e^{-\lambda}}{k!},$$

with $$\lambda = \frac{A_0 L_f V A_v (1 - e^{-Da}) e^{-(x-1)Da}}{N}$$

where V is the total volume of sample contacted with the capture regions, N is the number of digital units in a region, and $A_v$ is Avogadro's number. In this equation, k is the number of analytes in a single digital unit and $\lambda$ is the average number of labeled analytes per digital unit in a capture region. When k=0, the digital unit has no labeled analyte; the fraction of these negative counts can be described as $f(0; \lambda)=e^{-\lambda}$. The fraction of positive counts can thus be described as $1-f(0; \lambda)=\Sigma f(k, k>0; \lambda)$. An experiment with known $k_{on}$, [Ab], t, $L_f$, and N, $A_0$ can be quantified by a depletion curve plotted with the fraction of positive counts versus the order of the depletion regions. Some labeling antibodies can non-specifically absorb to the digital units and create a background signal that is unrelated to the analyte. This background signal can be added to the expression above:

$$\lambda = \frac{A_0 L_f V A_v (1 - e^{-Da}) e^{-(x-1)Da} + B}{N}$$

where B is the number of non-specifically bound labeling agents. When x is large enough, $\lambda \approx B/N$ can be considered independent of x, which becomes the flat tail of the depletion curve, allowing the calculation of B for each sample.

Analytes and Samples

The devices and methods described in this disclosure can be used for detection, quantification, and analysis of various analytes and samples. Analytes can comprise a single analyte or a single copy of an analyte. Analytes can comprise multiple copies of the same analyte or type of analyte. For example, in a digital unit with a number of analytes captured, the analytes can comprise multiple copies of the same analyte. Analytes can comprise multiple copies of similar or related analytes or types of analytes. For example, in a digital unit with a number of analytes captured, the analytes can comprise multiple copies of the similar or related analytes. Analytes can comprise multiple copies of analytes with similar or related features. For example, in a digital unit with a number of analytes captured, the analytes can comprise copies of analytes with similar or related features. Analytes can comprise multiple different types or kinds of analyte. For example, in a digital unit with a number of analytes captured, the analytes can comprise different analytes.

Samples can comprise a variety of materials, including but not limited to, blood, saliva, urine, stool, sputum, mucus, vomitus, pleural fluid, amniotic fluid, cerebrospinal fluid, peritoneal fluid, cells (e.g., epithelial cells), cell suspensions, biopsies (e.g., bone marrow biopsy, brain biopsy, skin biopsy, liver biopsy, muscle biopsy), tissue swabs (e.g., throat swab), cell scrapings, tissue, tissue extract, or reaction (e.g., amplification) products. Samples can comprise liquids, solids, or suspensions. Samples can comprise analytes.

Analytes can comprise nucleic acid. Nucleic acids can be cell-free nucleic acids. Nucleic acids can be isolated from cells. Nucleic acids can be single or double stranded. Analytes can comprise DNA or RNA. In some cases, the RNA is tRNA, mRNA, rRNA, trRNA, snRNA, snoRNA, smY, scaRNA, gRNA, RNase P, RNase MRP, aRNA, crRNA, incRNA, miRNA, piRNA, siRNA, tasi RNA, rasiRNA, 7SK, vRNA or any combination thereof. The DNA may be ssDNA, dsDNA, cDNA, or any combination thereof. In some cases, the DNA comprises a gene or a gene fragment. The gene or gene fragment can comprise a mutation. The mutation can comprise point mutations, insertions, deletions, amplifications, translocations, inversions, copy number variations, and/or other mutations. In some cases, the DNA comprises a non-coding region. The noncoding region can comprise functional sequences, regulatory elements, introns, exons, pseudogenes, repeat sequences, transposons, viral elements, telomeres, genetic switches, transcription factor sites, operators, enhancers, silencers, promoters, insulators, and/or other regions. In some cases, the DNA comprises cDNA. In some cases, the DNA is from bacteria or viruses. In some cases, the DNA is collected from a cell. In some examples, the DNA is intracellular. In some cases, the DNA is extracellular.

Analytes can comprise RNA. In some cases, the RNA comprises mRNA. In some cases, the RNA comprises noncoding RNA (ncRNA). The noncoding RNA can comprise transfer RNA (tRNA), ribosomal RNA (rRNA), transfer-messenger RNA (tmRNA), small nucleolar RNA (snoRNA), microRNA (miRNA), small interfering RNA (siRNA), small nuclear RNA (snRNA), piwi-interacting RNA (piRNA), long ncRNA (lncRNA), and/or other types of ncRNA. In some cases, the RNA is from bacteria or viruses. In some cases, the RNA is collected from a cell. In some examples, the RNA is intracellular. In some cases, the RNA is extracellular.

Analytes can comprise proteins, fragments of proteins, or aggregates of proteins. The proteins can comprise TNF-alpha. The proteins can comprise glial fibrillary acidic protein (GFAP). The protein can comprise p24. In some cases, the proteins comprise enzymes. In some cases, the proteins comprise signaling proteins. In some cases, the proteins comprise membrane proteins. The membrane proteins can comprise receptor proteins, transport proteins, membrane enzymes, cell adhesion proteins, lipoproteins, and/or other membrane proteins. In some cases, the proteins comprise antibodies. The antibodies can comprise extracellular or membrane-associated proteins. In some cases, the proteins comprise ligand transport proteins. The ligand transport proteins can comprise haemoglobin, lectins, other ligand transport proteins, or any combination thereof. The ligand transport proteins can comprise transmembrane proteins, such as ion channels. In some cases, the proteins comprise structural proteins. The structural proteins can comprise fibrous proteins, including collagen, elastin, keratin, or any combination thereof. The structural proteins can comprise globular proteins, including actin and tubulin monomers. The structural proteins can comprise motor proteins, including myosin, kinesin, dynein, or any combination thereof. In some cases, the protein is from a bacterium or from a virus. In some cases, the protein is collected from a cell. In some examples, the protein is collected from the cell membrane. Sometimes, the protein is intracellular. In some cases, the protein is extracellular. In some cases, the proteins comprise lipoproteins, including but not limited to high density lipoproteins and low density lipoproteins. In some cases, the proteins comprise tau or phosphorylated tau proteins.

Analytes can comprise peptides. In some cases, the peptides comprise tachykinin peptides. The tachykinin peptides can comprise substance P, kassinin, neurokinin A, neurokinin B, eledoisin, other tachykinin peptides, or any combination thereof. In some cases, the peptides comprise vasoactive intestinal peptides. The vasoactive intestinal peptides can comprise vasoactive intestinal peptide (VIP), pituitary adenylate cyclase activating peptide (PACAP), peptide histidine isoleucine 27 (PHI 27), growth hormone releasing hormone 1-24 (GHRH 1-24), glucagon, secretin, other vasoactive intestinal peptides, or any combination thereof. In some cases, the peptides comprise pancreatic polypeptide-related peptides. The pancreatic polypeptide-related peptides can comprise neuropeptide Y (NPY), peptide YY (PYY), avian pancreatic polypeptide (APP), pancreatic polypeptide (PPY), other pancreatic polypeptide-related peptides, or any combination thereof. In some cases, the peptides comprise opioid peptides. The opioid peptides can comprise proopiomelanocortin (POMC) peptides, enkephalin pentapeptides, prodynorphin peptides, other opioid peptides, or any combination thereof. In some cases, the peptides comprise calcitonin peptides. The calcitonin peptides can comprise calcitonin, amylin, AGG01, other calcitonin peptides, or any combination thereof. In some cases, the peptides comprise other peptides. The other peptides can comprise B-type natriuretic peptide (BNP), lactotripeptides, other peptides, or any combination thereof. In some cases, the peptides can comprise Abeta. In some cases, the peptides are from a bacterium or from a virus. In some cases, the peptides are collected from a cell. Sometimes, the peptides are collected from the cell membrane. Occasionally, peptides are intracellular. In some cases, the peptides are extracellular. A peptide can be a protein.

Analytes can comprise antigens. In some cases, the antigens comprise exogenous antigens. In some cases, the antigens comprise endogenous antigens. The endogenous antigens can be xenogenic, autologous, idiotypic, allogenic, other antigens, or any combination thereof. In some cases, the antigens comprise autoantigens. In some cases, the antigens comprise tumor antigens. The tumor antigens can comprise tumor-specific antigens (TSAs) tumor-associated antigens (TAAs), or any combination thereof. In some cases, the antigens are from bacteria or from a virus.

Analytes can comprise cells or fragments of cells. In some cases, the cells are bacterial. The bacterial cells can be collected from a culture, from a patient, from a surface, from the environment, from a biofilm, or from another source. The cells can comprise spores. The cells can comprise endospores. The cells can comprise anthrax spores. The cells can comprise B. anthraces cells. In some cases, the cells are prokaryotic. In some cases, the cells are eukaryotic. In some cases, the eukaryotic cells are human cells, or animal cells. The eukaryotic cells can be mammalian. A mammal can include, but is not limited to, a primate, ape, equine, bovine, porcine, canine, feline or rodent. A rodent can include, but is not limited to, a mouse, rat, or hamster. In some cases, the cells are tumor cells. The tumor cells can be taken directly from a tissue biopsy or can be circulating tumor cells. The cells can be fetal cells. The cells can be immune cells. The cells can be fungal cells.

Analytes can comprise viruses or viral particles (virions). Viruses can include, but are not limited to, norovirus, HIV, hepatitis C (HCV), common cold, influenza, chicken pox, ebola, and SARS. Analytes can comprise viral fragments. Analytes can comprise prions.

Analytes can comprise metabolites. Analytes can comprise small molecules. Analytes can comprise carbohydrates. Analytes can comprise glycopatterns. Analytes can comprise specific glycopatterns on proteins. Analytes can comprise specific glycopatterns on cells. Analytes can comprise vesicles, including but not limited to exosomes, exosome-like vesicles, microvesicles, epididimosomes, argosomes, microparticles, promininosomes, prostasomes, dexosomes, texosomes, dex, tex, archeosomes, and oncosomes. Analytes can comprise platelets. Analytes can comprise coagulation factors, including but not limited to Factor I, Factor II, Factor III, Factor IV, Factor V, Factor VI, Factor VII, Factor VIII, Factor IX, Factor X, Factor XI, Factor XII, Factor XIII, von Willebrand factor, prekallikrein (Fletcher factor), high-molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, cancer procoagulant, or combinations thereof.

The sample volume can be between about 10 microliter (μL) and about 1000 mL. The sample volume can be between about 100 μL and about 1000 mL. The sample volume can be between about 100 μL and about 100 mL. The sample volume can be between about 100 μL and about 10 mL. The sample volume can be between about 1 mL and about 1000 mL. The sample volume can be at least about 10 μL, 20 μL, 30 μL, 40 μL, 50 μL, 60 μL, 70 μL, 80 μL, 90 μL, 100 μL, 200 μL, 300 μL, 400 μL, 500 μL, 600 μL, 700 μL, 800 μL, 900 μL, 1 mL, 2 mL, 3 mL, 4 mL, 5 mL, 6 mL, 7 mL, 8 mL, 9 mL, 10 mL, 20 mL, 30 mL, 40 mL, 50 mL, 60 mL, 70 mL, 80 mL, 90 mL, 100 mL, 200 mL, 300 mL, 400 mL, 500 mL, 600 mL, 700 mL, 800 mL, 900 mL, or 1000 milliliter (mL).

The sample volume can be large compared to the volume of a digital unit, to the volume of reagent used, or to the volume of a device used. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 times the volume of a digital unit. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 times the reagent volume. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 times the device volume.

Device

This disclosure provides devices or platforms for the analysis of samples and analytes. Devices can be used for implementing the analyses described herein. Devices can comprise microfluidic devices. Devices can comprise channels and flowpaths, such as microfluidic channels. Devices can comprise inlets, outlets, or any combination thereof. Devices can comprise wells, reservoirs, or any combination thereof. Devices can comprise digital units. Devices can comprise capture regions or subsets of digital units. Devices can comprise pre-loaded reagents. In some cases, the device comprises a continuous flow microfluidic device. In some cases, the device comprises a droplet microfluidic device. In some cases, the microfluidic device comprises a surface acousitc wave (SAW) microfluidic device. In some cases, the microfluidic device comprises a SlipChip device, as described for example in U.S. patent application Ser. No. 13/257,811, in PCT Application No. PCT/US2010/028361, in US Patent Publication No. 20120329038 A1, and in International Patent Publication No. WO 2013072069 A1, each of which is hereby incorporated by reference in its entirety. Devices can comprise flow generators, including but not limited to pumps (including pressure or vacuum pumps), wicking materials, absorbent materials (e.g., paper), syringe, or capillaries. Pressure pumps may include bellow pumps. In some example the pumps are microfluidic pumps.

Devices can be fabricated with a variety of substrates or materials. Devices can comprise materials including but not limited to glass, silicon, plastic (e.g., PMMA), PDMS, metal, piezoelectric material, and paper.

Flow can be generated into, out of, or within devices by a variety of methods. Flow generation methods can include but are not limited to diffusion, Brownian motion, convection, pumping, applied pressure, gravity-driven flow, density gradients, temperature gradients, chemical gradients, pressure gradients, gas-producing chemical reactions (e.g. decomposition of $H_2O_2$), centrifugal flow, capillary pressure, wicking, electric fields, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, or combinations thereof Concentration The methods and devices disclosed herein can be applied to or used with analyte concentration and/or purification from large dilute samples. Independent of conducting an assay, digital units and capture regions can be used for analyte concentration. Analyte concentration can also be used in conjunction with assays, such as those described further in this disclosure.

Flow-through of digital units can allow for concentration of analytes. As sample flows through the digital unit, analyte can be captured by the digital unit, thereby concentrating it. In some cases, the concentration of analyte within a digital unit can be higher than the concentration of analyte in the original sample. The concentration of analyte in a digital unit can be at least about 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times higher than in the original sample. Large volumes of sample can be delivered to digital units. The sample volume can be large compared to the volume of a digital unit, to the volume of reagent used, or to the volume of a device used. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times the volume of a digital unit. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times the reagent volume. The sample volume can be at least about 2, 3, 4, 5, 6, 7, 8, 9, 10, 12, 13, 14, 15, 16, 17, 18, 19, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, or more times the device volume.

For example, a chitosan-coated membrane has the capability to isolate nucleic acids from samples with a concentrating factor of 1000-fold (e.g., 5 milliliter (mL) to 5 microliter (µL)). This can allow isolation of analytes, such as free DNA or RNA, with concentrating factors of up to 1000-fold (inclusive), without relying on resin slurries.

Initial preparation can be performed in a well or chamber to remove potentially harmful components such as excessive protein, RNases, and DNases. For example, incubation with Proteinase K, Zygem reagent, or similar protease treatment can deactivate and digest unwanted proteins. After capture of the analyte from a large volume of fluid, amplification and detection can occur directly on the capture matrix without the need for elution.

Separation and Access of Material

This disclosure provides techniques for accessing or separating material or analytes from a separation conduit with an access structure (with or without digital units). Separation can be conducted by a variety of means, including but not limited to chromatography, immunochromatography, electrophoresis, gel electrophoresis, capillary electrophoresis, magnetophoresis, dielectrophoresis, acoustophoresis, chemical gradients, temperature gradients, shear forces, fractionation, filtration, lateral displacement, Brownian ratcheting, hydrophoretic separation, trap arrays, magnetic force, optical force, sedimentation, centrifugation, diffusion, Brownian motion, convection, pumping, applied pressure, gravity-driven flow, density gradients, pressure gradients, gas-producing chemical reactions (e.g. decomposition of $H_2O_2$), capillary pressure, wicking, electric fields, magnetic fields, magnetically driven flow, chemotaxis, phototaxis, surface tension gradient driven flow, Marangoni stresses, thermo-capillary convection, surface energy gradients, surface acoustic waves, electroosmotic flow, thermophoresis, electrowetting, or any combination thereof. Separation conduits can comprise separation media, which can comprise components including but not limited to one or more fluids, buffers, beads, nanoparticles, gels, affinity matrices, solid matrices, magnetic components, or any combination thereof. Separation conduits can comprise digital units or capture regions. In some cases, separation conduits can have a smallest dimension that is less than or equal to about 1 millimeter, 500 micrometer (µm), 300 µm, 100 µm, or 50 µm. In some cases, separation conduits can have a volume less than or equal to about 20 microliter (µL), 5 µL, 1 µL, or 100 nanoliter (nL).

Accessing or separating material in separation conduits can comprise the use of access structures. Access structures can comprise channels. Access structures can be microfabricated. Access structures can be formed in the same device as the separation conduit. In some cases, access structures remain within at most 30 mm, 20 mm, 10 mm, 3 mm, 1 mm, or less of the separation conduit prior to, during, and after the accessing or separation. In some cases, access structures can have a smallest dimension that is less than or equal to about 1 millimeter, 500 micrometer (µm), 300 µm, 100 µm, or 50 µm. In some cases, access structures can have a volume less than or equal to about 20 microliter (µL), 5 µL, 1 µL, or 100 nanoliter (nL). Access structures can comprise digital units or capture regions. In some cases, access structures, or the fluid contained therein, do not substantially change in volume during the accessing or separation.

Transfer of material into or out of the separation conduit via the access structures can occur by a variety of techniques. Transfer can be conducted by positive pressure-driven flow (e.g., via a pump), by an electric field (e.g., electrophoresis), by capillary pressure, by vacuum, or by gravity. Transfer can be conducted by methods including but not limited to diffusion, Brownian motion, convection, pumping, applied pressure, gravity-driven flow, density gradients, temperature gradients, chemical gradients, pressure gradients, gas-producing chemical reactions (e.g. decomposition of $H_2O_2$), centrifugal flow, capillary pressure, wicking, electric fields, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, or combinations thereof. Transfer of material can occur without exposing the separation conduit or separation media to the ambient environment. For example, access structures can be contacted with the separation conduit by the actuation of a SlipChip microfluidic device, as described further in this disclosure.

Material transferred from the separation conduit can include analyte, reagents (e.g. labeling agents), buffers, and separation media. Material transferred to the separation conduit can include analyte, reagents (e.g. labeling agents), buffers, and separation media. In an example, analyte can be separated in the separation conduit, and specific bands or regions of analyte can be accessed and removed via access structures. In another example, analyte can be separated in the separation conduit, reagent can be added to the separation conduit via the access structures, and a reaction can be performed in the separation conduit (e.g., labeling reaction, amplification reaction).

Figure 39A:
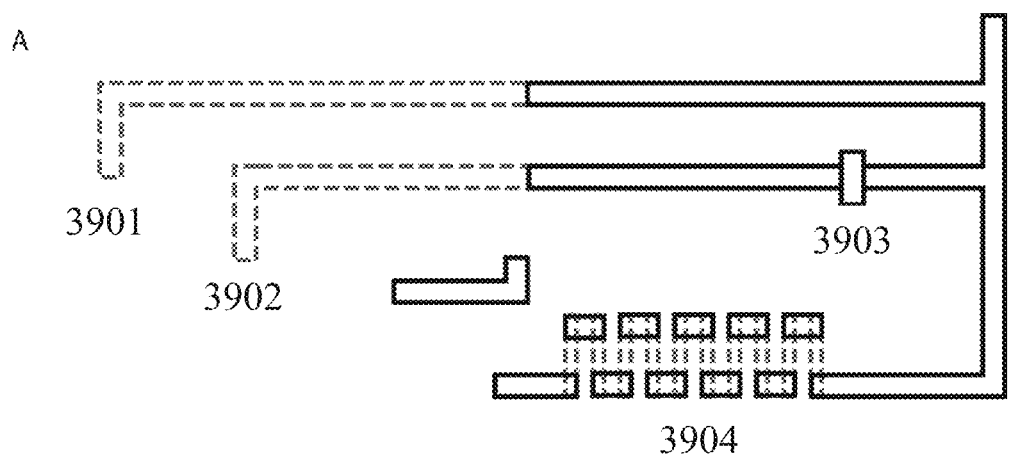
FIG. 39A shows an exemplary schematic of a device with a separation conduit.
Figure 39B:
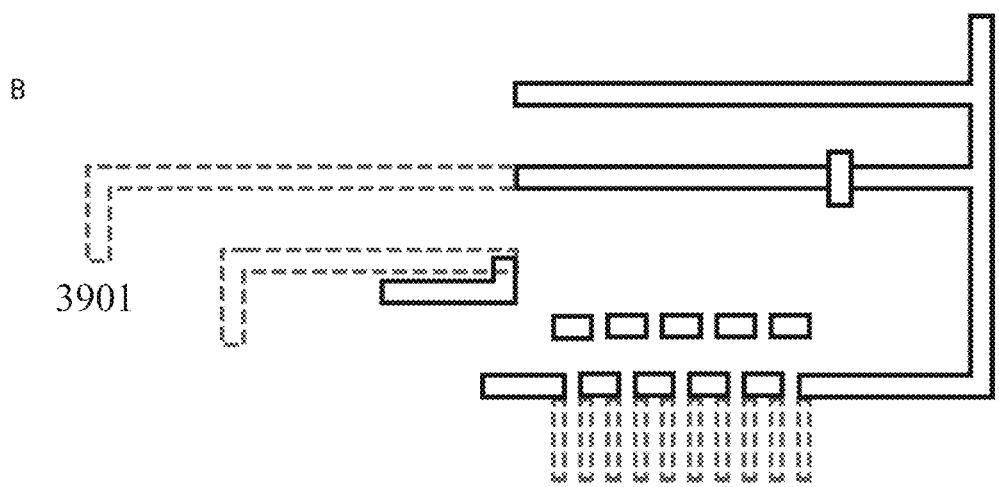
FIG. 39B shows an exemplary schematic of a device slipped to align the sample conduit with the separation conduit, so that sample can be loaded into the separation conduit
Figure 39C:
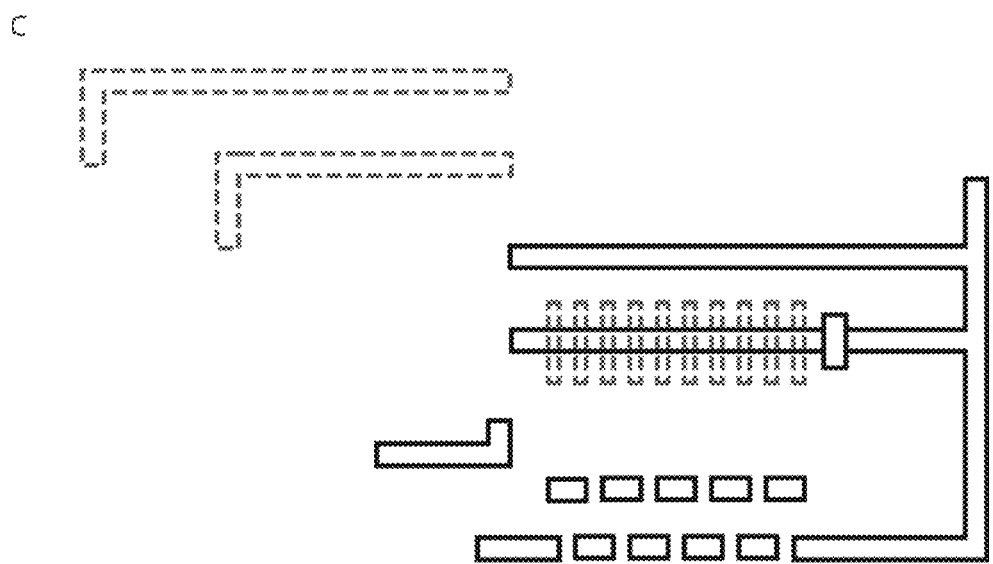
FIG. 39C shows an exemplary schematic of a device with two plates slipped to allow loading of separation media into access structures.
Figure 39D:
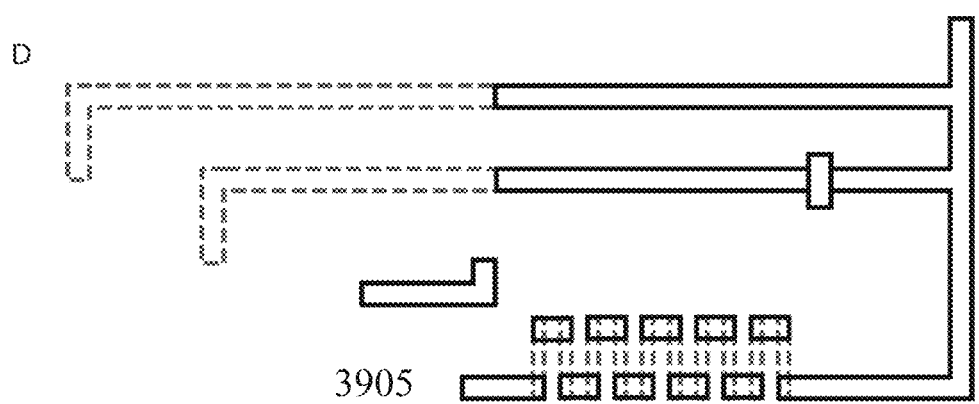
FIG. 39D shows an exemplary schematic of a device with two plates slipped to align the access structures with a reagent conduit, such as a labeling reagent conduit.
Figure 39E:
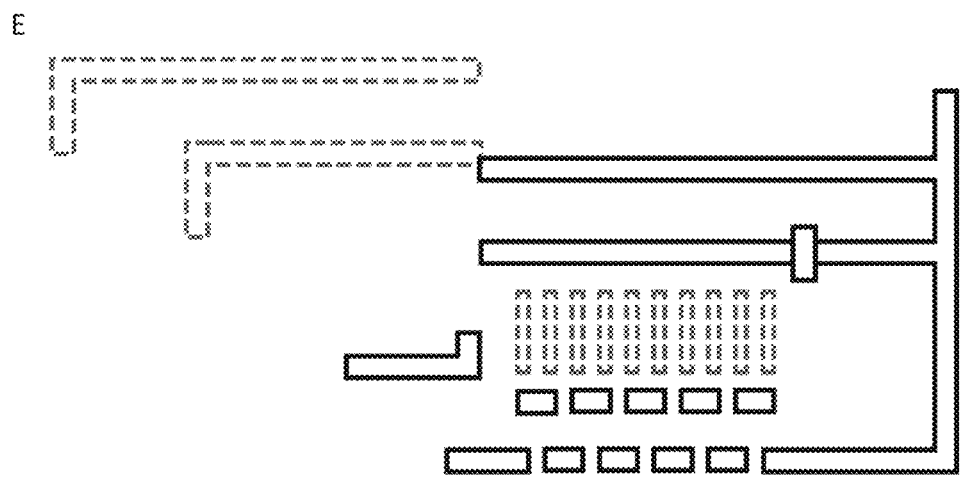
FIG. 39E shows an exemplary schematic of a device with access structures separated from the reagent conduit.
Figure 40A:
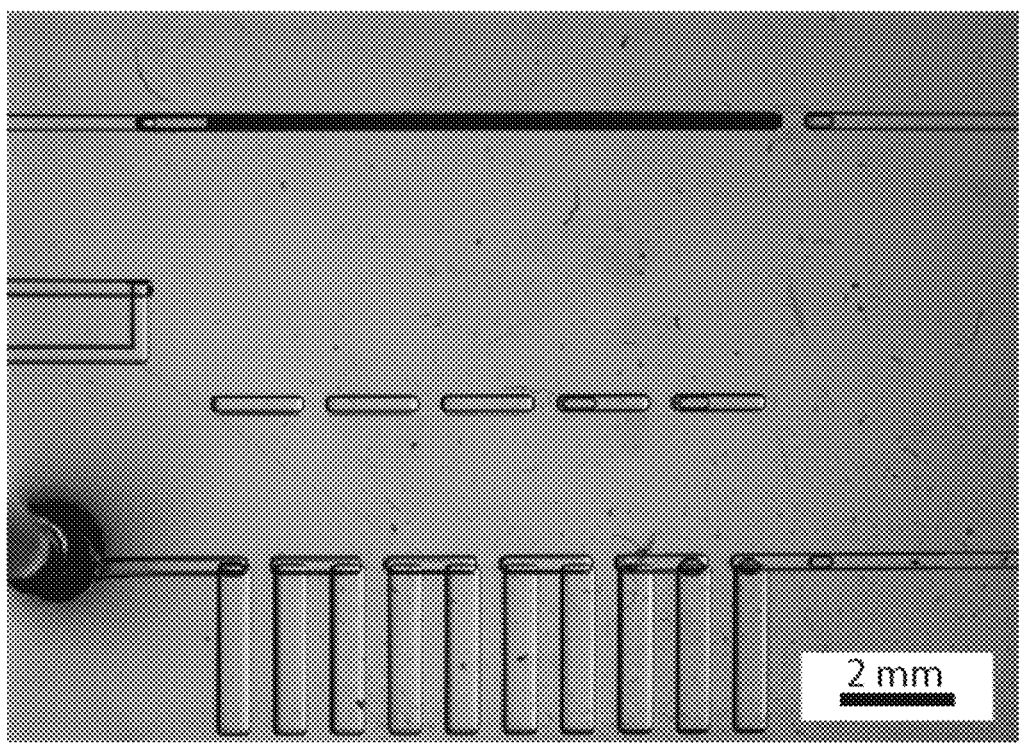
FIG. 40A shows an exemplary device with a separation conduit ready for sample loading (c.f.
Figure 40B:
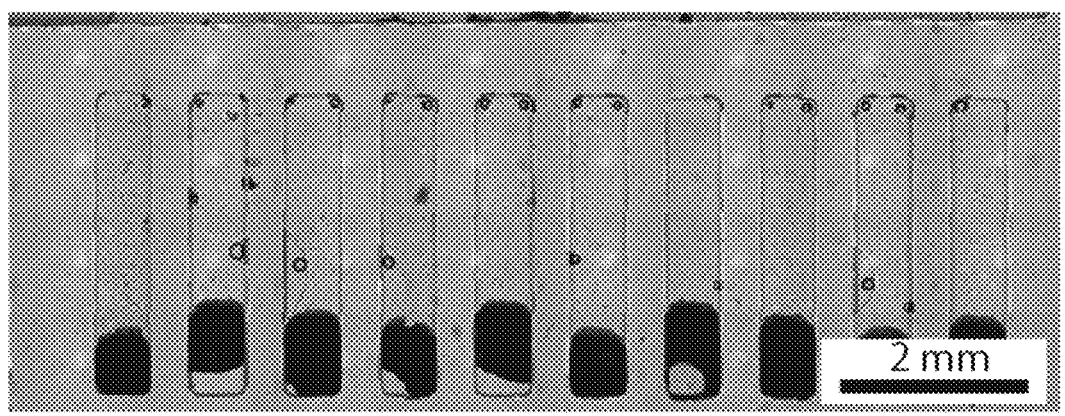
FIG. 40B shows an exemplary brightfield micrograph of access structures containing separation media with analyte.
Figure 40C:
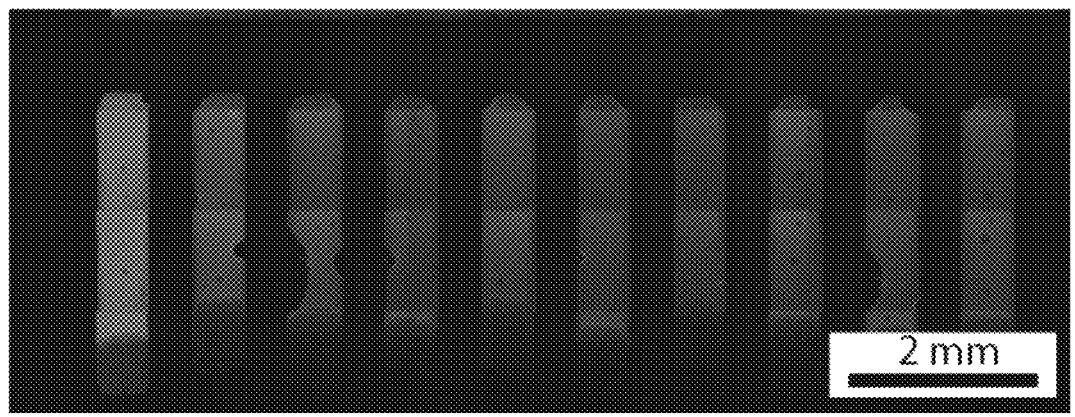
FIG. 40C shows an exemplary fluorescent micrograph of access structures containing separation media with analyte.

For example, FIG. 39 and FIG. 40 show a separation in separation media followed by accessing and separating separation media from the separation conduit. The operation is conducted in a SlipChip device, comprising two plates coupled together. Features in the top plate are shown in solid line, while features in the bottom plate are shown in dotted line. FIG. 39A shows a schematic of a device with a separation conduit, into which a bead slurry separation media can be injected 3902, with a dam structure 3903 to contain it. Sample can also be loaded into the device 3901. FIG. 39B and FIG. 40A show the two plates slipped to align the sample conduit with the separation conduit, so that sample can be loaded into the separation conduit. Analyte in the sample can then bind to separation media. FIG. 39C shows the two plates slipped to allow loading of separation media into access structures 3904. In some cases, the separation media can comprise magnetic beads, and motion of separation media with bound analyte into the access structures can be conducted with magnetic force. FIG. 39D shows the two plates slipped to align the access structures with a reagent conduit, such as a labeling reagent conduit 3905. After labeling, the separation media can be washed. FIG. 39E shows access structures separated from the reagent conduit, and FIG. 40B and FIG. 40C show images of labeled analyte in access structures.

Washing

This disclosure provides methods and devices for washing material, such as samples or analytes. Material to be washed can be coupled or bound to a transport material, such as beads, particles, microparticles, nanoparticles, cells, or any combination thereof. Transport material can then be moved, transporting the coupled material to be washed. Alternatively, material to be washed can be capable of being moved directly. Material to be washed can then be moved, directly or indirectly, through washing solution and into a receiving area.

For example, FIG. 46C shows material to be washed in a sample area 4611 contacted and coupled with magnetic beads 4601. The device can then be actuated 4602 to allow fluid communication between the sample area and a washing chamber 4612, and force (e.g., magnetic force) can be applied to move the magnetic beads and associated material to be washed through the washing chamber 4603, and to collect them in a receiving area 4613. Finally, the device can be actuated 4604 to isolate the receiving area from the washing chamber.

Transport material can comprise a range of material, including but not limited to beads, microparticles, nanoparticles, cells, magnetic material, paramagnetic material, material with a density greater than or less than that of water, and any combination thereof. Samples and analytes are further described elsewhere in this disclosure. Material to be washed that is capable of being moved directly can include analytes such as cells, nucleic acids, and proteins.

Transport methods can include but are not limited to diffusion, Brownian motion, convection, pumping, applied pressure, gravity-driven flow, density gradients, temperature gradients, chemical gradients, pressure gradients, gas-producing chemical reactions (e.g. decomposition of $H_2O_2$), centrifugal flow, capillary pressure, wicking, electric fields, electrophoresis, dielectrophoresis, magnetophoresis, magnetic fields, magnetically driven flow, optical force, chemotaxis, phototaxis, surface tension gradient driven flow, Marangoni stresses, thermo-capillary convection, surface energy gradients, acoustophoresis, surface acoustic waves, electroosmotic flow, thermophoresis, electrowetting, or combinations thereof.

Material can be isolated before or after washing. Isolation can occur by physical separation of chambers and areas, for example by actuation of a device (e.g., a SlipChip device). In some cases, isolation can occur without the use of pneumatic valves. In some cases, isolation can occur without substantial change to the volume of the chambers or areas. Chambers can be formed in the same or in different substrates from each other.

The washing chamber can comprise washing buffer. The washing chamber can comprise separation media. Transport of material through a washing chamber comprising separation media can be used to separate analytes. For example, similar analytes can bind to transport material and be transported into a washing chamber, and therein be separated based on a different property, such as binding affinity, size, electric charge, or a combination thereof. In another example, analytes can be moved into a washing chamber directly without transport material, and therein be separated based on a physical property, such as binding affinity, size, electric charge, or a combination thereof.

EXAMPLES

Example 1—Circular Rotational Assay

Figure 2A:
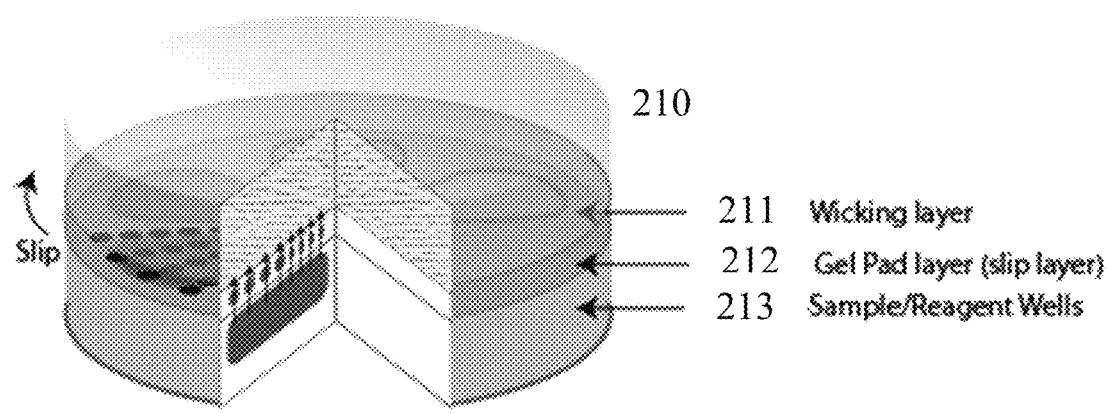
FIG. 2A shows an exemplary scheme for a rotational assay with sample/reagent wells, a gel pad layer, and a wicking layer.
Figure 2B:
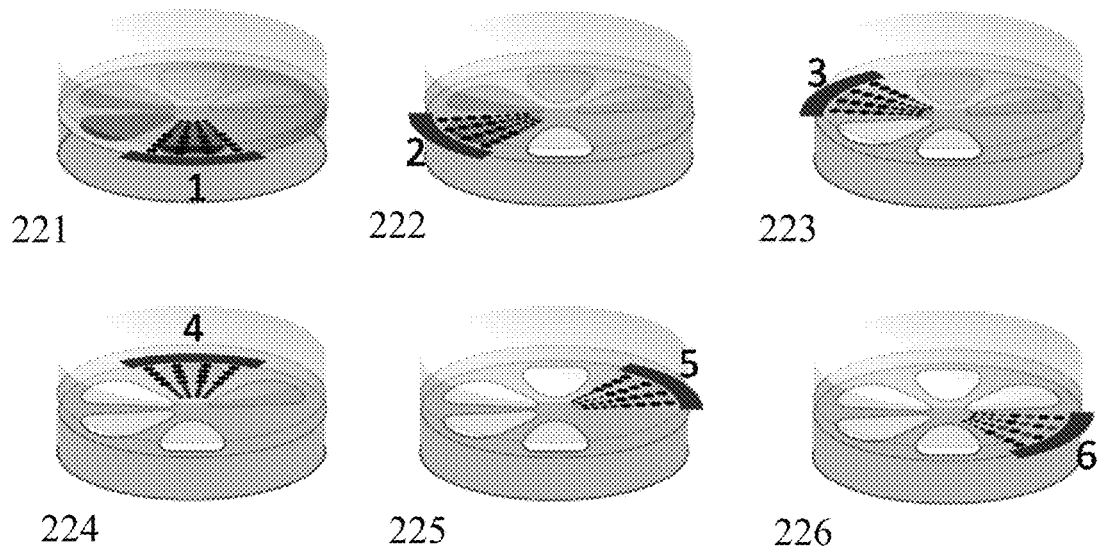
FIG. 2B shows exemplary steps for conducting the rotational assay in the device of FIG. 2A.

A potential device for flowing different volumes in milliliter (mL) to femtoliter (fL) range over digital units for capturing analyte can be a device as outlined below and depicted in FIG. 2. The consists of 3 stacked layers or plates that have dimensions of several millimeters to centimeters. The top layer 211 contains a substance capable of generating negative pressure, such as a wicking material made of, for example, nitrocellulose or cellulose acetate. The middle layer 212 of the device contains capture regions of different dimensions, each ranging from several mm to 1 µm in size. In some cases, no patterned capture regions are necessary. The bottom layer 213 consists of wells with larger dimensions than the digital units, but still in the several mm to microns range, that contain reagents and samples. The middle layer of the device can be rotated relative to the top and bottom layers that remain fixed in space. When the digital units of the middle layer are placed in between a reagent or sample in the bottom layer and the wicking material in the top layer, the reagent or sample will be transported through the digital units into the wicking material. The flow rates with which liquids are transported from the bottom layer into the top layer can for example be adjusted by tailoring the pore-size of the material that is used for wicking. Flow rates can be vary from 0.01 µL/min to 100 s of µL/min. Larger digital units will allow a larger volume of sample/reagent to be transported through the digital unit and will therefore have a higher probability of capturing a target molecule than smaller digital units. In subsequent steps, the middle layer containing the digital units is rotated to other sections in the bottom layer and hence to subsequent reagents such as labeling reagents, buffers, etc., which will flow through the digital units in those subsequent steps. In FIG. 2, 6 different liquids, which can be samples or reagents, are transported through the digital units in subsequent steps 221, 222, 223, 224, 225, 226 by rotating the digital units clockwise. Multiple regions of differently sized capture matrices allow quantification of the target molecule in the sample: the concentration of target molecule can be calculated based on the number of elements in each region that give a positive signal. These devices can be fabricated out of different materials such as injection molding or 3D printing, among others. After fabrication, the different layers of the device can be assembled placed in a plastic holster that ensures proper alignment.

Example 2—Hydrogel Capture Patches

One example of element design is shown in FIG. 3, which shows the Da 302 of 500 µm diameter cylindrical hydrogel patches and the corresponding time 301 required to pull 10 µL through 100 distinct parallel patches. A Da=10 within a patch or within one section of digital unit corresponds to ~90% of the analyte binding within that region. Using this method, 90% of the analyte can be capture from 10 µL of sample in 120 s using 100 patches (0.1 µL/patch). Hydrogel patches with a smaller cross-sectional area (width) but the same length will have the same Da, but have smaller volumes of fluid flowing through them. This will result in a smaller probability of containing enough bound analyte for downstream detection. Due to the high volumetric flow rate, this technique can concentrate the analyte from a large dilute sample solution.

Example 3—Signal Detection on Capture Matrix

Figure 7C:
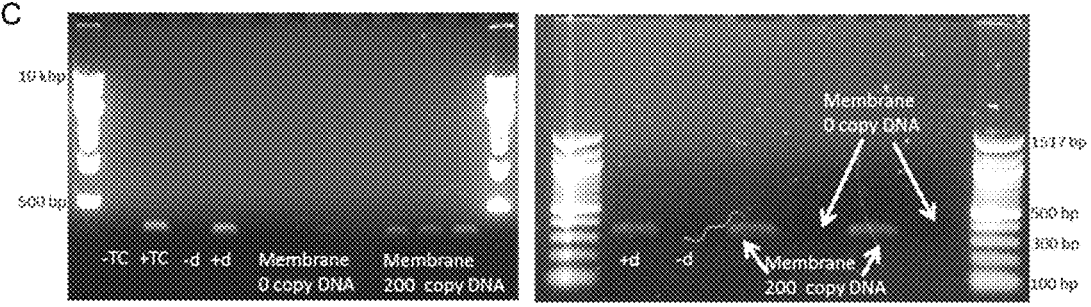
FIG. 7C shows an exemplary agarose gel separation of PCR product eluted from membranes, as well as positive and negative controls.

After capture of the analyte from a large volume of fluid, amplification and detection can occur directly on the capture matrix without the need for elution. For example, both LAMP (loop mediated isothermal amplification) and PCR (polymerase chain reaction) can be performed with 200 copies of lambda phage DNA on a polypropylene membrane functionalized with a charge-switch chitosan hydrogel, where the material charge can switch in response to pH changes. Membranes, as shown in FIG. 1, were cut into 2 mm diameter rounds and subjected to a mock purification process by introducing a low pH buffer (10 mM MES (i.e. 2-(N-morpholino)ethanesulfonic acid buffer)) through the membrane. A 1 µL amplification mixture droplet containing 200 copies of lambda phage DNA and either PCR with Evagreen for fluorescent readout or LAMP with calcein for a fluorescent readout was wicked into each membrane round. Negative controls contained no DNA. Amplification was then performed in situ under mineral oil, with 40 cycles for PCR and 60 minutes for LAMP. There is a clear increase in fluorescence in the presence of the lambda phage after amplification using either PCR (FIG. 7A) or LAMP (FIG. 7B) as the amplification chemistry. Additionally, DNA from in situ PCR reactions was eluted from the membrane and run on a 1.2% Agarose gel to confirm the correct 322 bp product was produced (FIG. 7C). Positive controls from PCR in 14 droplets under mineral oil (+d) and from PCR performed in a thermocycler (+TC) under the same reaction conditions also show the correct 322 bp product.

Example 4—Integrated Single Volume Device

FIG. 8 shows an example of an integrated single volume device for sample preparation, digital amplification, and detection of single molecules. A complex biological sample such as plasma containing nucleic acid or protein analytes (indicated by red stars) flows through a 3D capture matrix (blue mesh). Total volume is determined either by receiving wells below each set of membrane patches or by supplying wells; receiving wells are shown here. In an optional step, the membrane is slipped to wash away contaminants. A) Nucleic acids can be eluted into single volume wells for downstream amplification. B) Alternatively, reactants can be added directly to the digital 3D matrix elements, and amplification and readout can be performed directly in the 3D matrix to detect single protein or nucleic acid molecules. These functions can be performed on a SlipChip device. While these wells are fluidically connected, in some embodiments, that fluid connectedness may not be needed.

Example 5—Integrated Single Volume Device with Multiple Readout Units

FIG. 9 shows an example of an integrated single-volume device for sample preparation, digital amplification, and detection of single molecules. A complex biological sample such as plasma containing nucleic acid or protein analytes (indicated by red stars) flows through a 3D capture matrix (blue mesh). Total volume is determined either by receiving wells below each set of membrane patches or by supplying wells; receiving wells are shown here. In an optional step, the membrane is slipped to wash away contaminants. A) Nucleic acids can be eluted into single volume wells for downstream amplification. B) Alternatively, reactants can be added directly to the digital 3D matrix elements, and amplification and readout can be performed directly in the 3D matrix to detect single protein or nucleic acid molecules. These functions can be performed on a SlipChip device. While these wells are fluidically connected, in some embodiments, that fluid connectedness may not be needed. In some embodiments, a single volume can be divided into multiple digital units for readout (9 digital units per volume are shown here).

Example 6—Integrated Multi-Volume Device with Multiple Readout Units

FIG. 10 shows an example of an integrated multi-volume device for sample preparation, digital amplification, and detection of single molecules. A complex biological sample such as plasma containing nucleic acid or protein analytes (indicated by red stars) flows through a 3D capture matrix (blue mesh). Total volume is determined either by receiving wells below each set of membrane patches or by supplying wells; receiving wells are shown here. In an optional step, the membrane is slipped to wash away contaminants. A) Nucleic acids can be eluted into single volume wells for downstream amplification. B) Alternatively, reactants can be added directly to the digital 3D matrix elements, and amplification and readout can be performed directly in the 3D matrix to detect single protein or nucleic acid molecules. These functions can be performed on a SlipChip device. While these wells are fluidically connected, in some embodiments, that fluid connectedness may not be needed. In some embodiments, a single volume can be divided into multiple digital units for readout (9 digital units per volume are shown here).

Example 7—Integrated Digital Device

Figure 11:
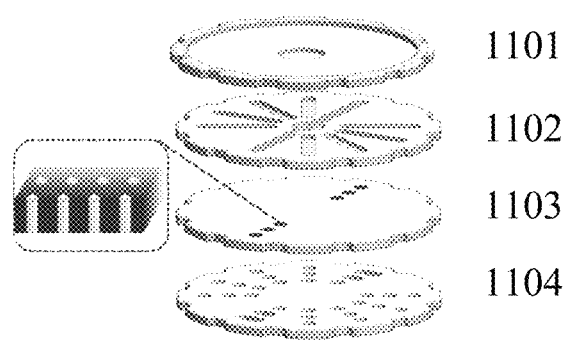
FIG. 11 shows an exemplary schematic of an integrated digital SlipChip device for capture and purification in 3D digital matrices.

FIG. 11 shows an integrated digital SlipChip device for capture and purification in 3D digital matrices. The sample is introduced in the top layer 1101, and the volume pushed through the 3D capture matrix (membrane/gel) 1103 is determined by the receiving wells on the bottom of the device 1104. The layer containing the digital 3D capture matrix elements are sequentially slipped under the reagents 1102 to wash away contaminants and amplify the target molecule.

Example 8—Chitosan-Functionalized Membranes and In Situ RT-LAMP

Figure 12:
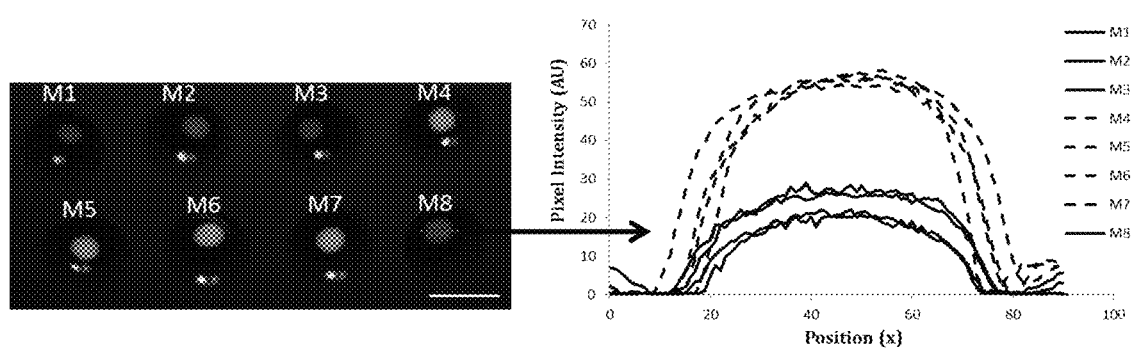
FIG. 12 shows exemplary chitosan-functionalized membranes after an in situ RT-LAMP reaction (left) and fluorescence intensity traces of the membranes (right).

FIG. 12 shows chitosan-functionalized membranes after an in situ RT-LAMP reaction. Membranes 2-8 contained 50 copies of HIV RNA, and membrane 1 contained 0 copies of HIV RNA. Membranes 4-7 contained amplified product as determined by real-time calcein fluorescence traces from a stereoscope, as well as positive fluorescence from epifluorescent microscope images. Membranes containing amplified products (dashed line trace) were clearly discernible from membranes containing no amplified products (solid line trace). The line in M8 shows where the fluorescence trace is located. Scale bar is 5 mm.

Example 9—Effect of Chitosan Concentration

Figure 13:
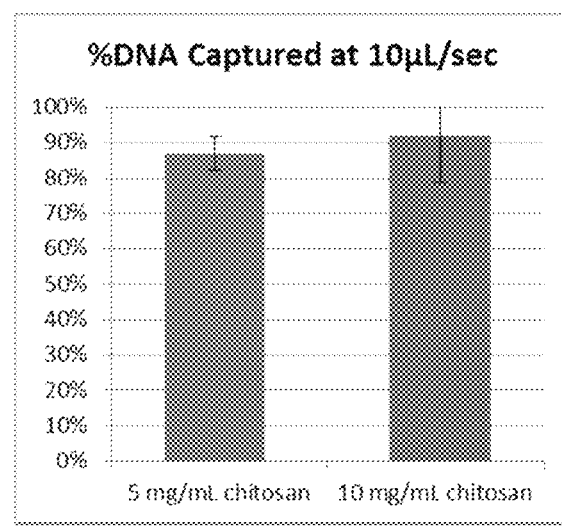
FIG. 13 shows an exemplary percentage of DNA captured for 3D matrices coated using 10 mg/mL and 5 mg/mL chitosan solutions, respectively.
Figure 14:
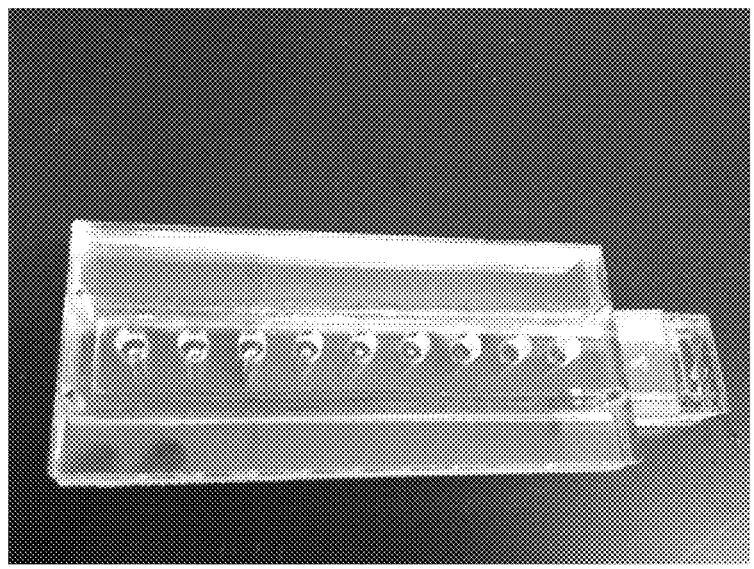
FIG. 14 shows an exemplary acrylic apparatus for conducting assays.
Figure 15:
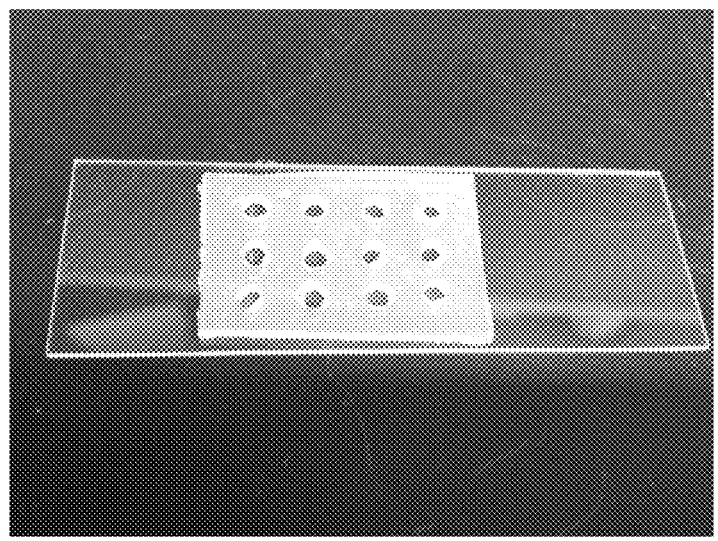
FIG. 15 shows an exemplary PDMS gasket system for conducting assays.

FIG. 13 shows a comparison of the percent of DNA captured for 3D matrices coated using 10 mg/mL and 5 mg/mL chitosan solutions, respectively. 100 µL of 100 ng/mL λ-phage DNA with 3 mg/mL BSA in 10 mM MES was flowed through a nucleic acid capture matrix for approximately 10 seconds. The outlet DNA concentrations were measured using PicoGreen dye. 4 experiments were performed for 5 mg/mL chitosan and 5 experiments for 10 mg/mL. The error bars are plus or minus (+/−) 1 standard deviation.

Example 9—Multivolume Capture and Amplification

An experiment is carried out according to the following procedure:

RT-LAMP mix is prepared, comprising 18 µL of reaction mix (RM), 1.44 µL of enzyme mix (EM), 0.9 µL of FD (calcein), 1.8 µL of primer mixture (20 µM BIP/FIP, 10 µM LooP_B/Loop_F, and 2.5 µM B3/F3), 3.6 µL of 100 ng/µL cRNA and enough nuclease-free (NF) water to bring the volume to 30 µL. To make the positive control mix (also called Positive LAMP mix or (+) RT-LAMP), 6 µL of RT-LAMP mix is removed and added to 1.2 µL HCV viral RNA (prepared from plasma with Maxwell machine). To make the negative control mix (also called Negative LAMP Mix, or (−) RT-LAMP), which also serves as the amplification mix, 4.8 µL of NF water is added to the remaining 24 µL of RT-LAMP mix.

Capture mixes are prepared. Solution A is prepared, comprising 1.42 µL of 300 copies/µL RNA added to 848.58 µL 10 mM MES to make 850 µL of 0.5 copies/µL RNA. Capture Mix 1 (CM1) is prepared, comprising 0.80 µL of 5 ng/µL cRNA added to 800 µL Solution A (approximately 1 ng cRNA and 100 copies HCV RNA per 200 µL). Capture Mix 2 (CM2) is prepared, comprising 1.00 µL of 5 ng/µL cRNA added to 50 µL Solution A (approximately 1 ng cRNA and 5 copies HCV RNA per 10 µL)

The experiment is then conducted as follows: 1) Punch 10 chitosan membranes (diameter is 2 mm) from a membrane sheet, which is fabricated as described in Example 12. Place one membrane in qPCR well plate. 2) Add 500 µL NF water to membranes. 3) Place 9 membranes on the bottom half of the acrylic apparatus and wick away water with Kimwipe™. 4) Line up membranes in holes. Put top half on and clamp. 5) Make sure flow-through is working with 50 µL water. While setting up LAMP mix, leave 50 µL MES over membranes to keep them wet. 6) Pipette out MES and immediately introduce capture RNA mix. 7) Connect acrylic apparatus to vacuum. 8) For the 9 membranes in the acrylic apparatus: a) add 200 µL CM1 to 4 membranes, b) add 10 µL CM2 to 4 membranes c) add 50 µL of 10 mM MES to 1 membrane, and d) wait for solution to flow through membranes. 9) Twice, add 100 µL 10 mM MES and wait for solution to flow through membranes. 10) Once, add 20 µL NF water and wait for solution to flow through membranes. 11) Disassemble acrylic apparatus, take membranes out. 12) Blot dry each membrane on Kimwipe™; place in qPCR well plate. 13) Place 2 µL (−) RT-LAMP mix with each of the 9 membranes that had capture mix flowed through. 14) Into three different wells, place 2 µL (−) RT-LAMP mix to set up three negative droplet controls. 15) Into two different wells, place 2 µL (+) RT-LAMP mix to set up two positive droplet controls and 2 µL in well with membrane from Step 2. 16) Amplify on Eco machine for 70 min at 63° C. while monitoring the reaction in real-time.

Example 10—Multi-Concentration Capture and Amplification

An experiment is carried out according to the following procedure:

RT-LAMP mix is prepared, comprising 18 µL of reaction mix (RM), 1.44 µL of enzyme mix (EM), 0.9 µL, of FD (calcein), 1.8 µL of primer mixture (20 µM BIP/FIP, 10 µM LooP_B/Loop_F, and 2.5 µM B3/F3), 3.6 µL of 100 ng/µL cRNA and enough nuclease-free (NF) water to bring the volume to 30 µL. To make the positive control mix (also called Positive LAMP mix, or (+) RT-LAMP), 6 µL of RT-LAMP mix is removed and added to 1.2 µL HCV viral RNA (prepared from plasma with Maxwell machine). To make the negative control mix (also called Negative LAMP Mix, or (−) RT-LAMP), which also serves as the amplification mix, 4.8 µL of NF water is added to the remaining 24 µL of RT-LAMP mix.

Capture mix is prepared, comprising 0.5 µL of 100 ng/µL cRNA added to 499.5 µL of 10 mM MES to make 500 µL of 0.1 ng/µL cRNA (Solution B). Capture Mix 1 comprises 1.33 µL of 300 copies/µL HCV RNA added to 198.67 µL Solution B (approximately 5 ng cRNA and 100 copies HCV RNA per 50 µL). Capture Mix 2 comprises 75 µL of CM1 is added to 75 µL Solution B (approximately 5 ng cRNA and 50 copies HCV RNA per 50 µL). Capture Mix 3 comprises 7.5 µL of CM1 is added to 142.5 µL Solution B (approximately 5 ng cRNA and 5 copies HCV RNA per 50 µL). Capture Mix 4 comprises 50 µL Solution B (approximately 5 ng cRNA and 0 copies HCV RNA per 50 µL)

The experiment is then conducted as follows: 1) Punch 10 chitosan membranes (diameter is 2 mm) from a membrane sheet, which was fabricated as described in Example 12. Place one membrane in qPCR well plate. 2) Add 500 µL NF water to membranes. 3) Place 9 membranes on the bottom half of the acrylic apparatus and wick away water with Kimwipe™. 4) Line up membranes in holes. Put top half on and clamp. 5) Make sure flow-through is working with 50 µL water. While setting up LAMP mix, leave 50 µL MES over membranes to keep them wet. 6) Pipette out MES and immediately introduce capture RNA mix. 7) Connect acrylic apparatus to vacuum. 8) For the 9 membranes in the acrylic apparatus: a) add 50 µL Capture Mix 1 to 2 membranes, b) add 50 µL Capture Mix 2 to 3 membranes, c) add 50 µL of Capture Mix 3 to 3 membranes, d) add 50 µL of Capture Mix 4 to 1 membrane, and e) wait for solution to flow through membranes. 9) Twice, add 100 µL 10 mM MES and wait for solution to flow through membranes. 10) Once, add 20 µL NF water and wait for solution to flow through membranes. 11) Disassemble acrylic apparatus, take membranes out. 12) Blot dry each membrane on Kimwipe™; place in qPCR well plate. 13) Place 2 µL (−) RT-LAMP mix with each of the 9 membranes that had capture mix flowed through. 14) Into three different wells, place 2 µL (−) RT-LAMP mix to set up three negative droplet controls. 15) Into two different wells, place 2 µL (+) RT-LAMP mix to set up two positive droplet controls and 2 µL in well with membrane from Step 2. 16) Amplify on Eco machine for 70 min at 63° C. while monitoring the reaction in real-time.

Example 11—Plasma Lysis

An experiment is carried out according to the following procedure: 1) 75 µL lysis buffer and 30 µL Proteinase K (NEB) are added to 270 µL plasma (George King) (lysis buffer comprises 7.5M urea, 25 mM EDTA, 0.5% TritonX). 2) Incubate 10 min at 63° C. 3) Add 41.74 binding buffer (binding buffer comprises 104 of 1M NaOAC with 90 µL 1M HOAc).

Reagents comprise: LoopAmp RNA amplification kit and Calcein fluorescence indicator kit from SA Scientific (Enzyme mix, reaction mix, 0.2% Tween, 1.6M betaine, 2.8 mM dNTP, 100 ng/pt carrier RNA, RNAse out (2 U/µL)); 2 mg/mL BSA (Roche Diagnostics); RNAse out (Invitrogen 10777-019); Mineral oil (Sigma M5904); PDMS gasket (McMaster Carr) with 3M adhesive on one side (orange, 5787T63); Dichlorodimethyl silane coated slides The experiment is then conducted as follows: 1) Punch 2 mm diameter membranes from a membrane sheet, which was fabricated as described in Example 13, and soak in 10 mM 2-(N-morpholino)ethanesulfonic acid (MES), pH~4.8. 2) Place membrane on cleanroom wipers, wick 10 µL NF water through. 3) Punch 4 mm holes in PDMS gasket; stick PDMS gasket on silanized glass slide. 4) Place membranes inside PDMS gasket holes. 5) Wick 1 µL LAMP amplification mix into each membrane, cover with ~20-30 µL mineral oil. 6) Image in real-time (1 image/min), cover with petri dish; lid heating at 63° C.; block heating 70 min at 63° C., 2 min at 85° C., then hold at 10° C. 7) Image on Leica DM6K, 40 s, 5×/0.15 NA, 0.63 coupler. 8) Image using Nokia cell phone. An example result is shown in FIG. 12.

Example 12—Membrane Fabrication—LoProdyne Membrane

A membrane is prepared according to the following procedure:

Step 1: activate LoProdyne membrane for attachment of amines from chitosan as described by membrane manufacturer (Pall Corporation). LoProdyne LP membrane has hydroxyl surface chemistry. The membrane binds very little protein in standard binding tests using IgG or BSA. The membrane can be activated for covalent attachment using N, N'-carbonyldiimidazole (CDI) in methylene chloride as follows: 1) Dissolve 0.49 g CDI in 45 mL MeCl2. 2) Add to a glass dish under a fume hood. 3) Immerse sheet of LoProdyne LP membrane in this solution for 15 minutes, RT. 4) Wash membrane 4× with 40 mL per wash $MeCl_2$, 5 minutes per wash. 5) Air dry at 60° C. for 3 minutes. 6) Store in vacuum desiccator until use.

Step 2: functionalize with chitosan. CDI is active at high pH (9-10) because amines should be deprotonated for the crosslinking chemistry to function optimally. This means that a lower concentration of active amines is optimal to avoid loss of all amine groups to crosslinking sites. With a pKa~6.3 for chitosan, only 15% of amines will be deprotonated at a pH of 5.5 (~4% at a pH of 5.1). 1) Determine pH of chitosan oligosacharride lactate (5-20 mg/mL) with added 1M NaOH, as shown in Table 1:

TABLE 1

| pH of chitosan oligosacharride lactate with added 1M NaOH | | | | | |
|---|---|---|---|---|---|
| 6.3 | pKa | | | µL 1M NaOH/mL to get pH | |
| pH desired | $NH_2$/$NH_3^+$ | % $NH_2$ | NH2/ chitosan | 5 mg/mL | 10 mg/mL |
| 5.2 | 0.079 | 0.074 | 1.693 | 2.81 | 4.76 |
| 4.9 | 0.040 | 0.038 | 0.881 | 2.04 | 3.73 |
| 4.7 | 0.025 | 0.025 | 0.564 | 1.57 | 2.84 |

Usually, <1 $NH_2$/chitosan is desired so the chitosan doesn't lay flat on the membrane and there are free amines floating around to grab nucleic acids. 2) Dissolve chitosan in nuclease-free water at desired concentration. 3) Add 1M NaOH to chitosan (adjust to desired pH) while vortexing to avoid precipitate. LiOH, KOH, RbOH or CsOH may be used instead of NaOH. 4) Incubate with membrane 1 hour room temperature (solution), or dry down for 20 minutes (dry). Note: the dry down membranes can give much better results (best results from 5-10 mg/mL, pH 4.7 dry down membranes). ("Dry down" comprises the following: place membrane on glass slide; wet membrane with chitosan solution; place second glass slide on top and squeeze solution out the edges; blot dry outside of membrane and place in dessicator to dry for 20 minutes.) 5) Rinse once in water and add 0.1M HCl. Mix well and incubate 2 minutes. 6) Rinse three times in nuclease free water. 7) Incubate in NF water for 30 minutes, agitated. 8) Rinse three times in water (running under water, having typically 18.2 MΩ·cm at 25° C.).

Example 13—Membrane Fabrication—Polypropylene Membrane

Reagents comprise: 1) 50 mM MES (i.e., 2-(N-morpholino)ethanesulfonic acid), pH~4.8, 2) EDC (i.e., 1-Ethyl-3-[3-dimethylaminopropyl]carbodiimide hydrochloride) (Pierce 22980), diluted to 100 mg/mL in MES (1); 5.8 mg in 58 µL, 3) Sulfo-NHS (i.e., Sulfo-N-Hydroxysuccinimide; Pierce 24510), diluted to 100 mg/mL in MES (1); 6.7 mg in 67 µL, 4) Chitosan oligosaccharide lactate (Sigma 523682, Mn~5000), 5) 8% Glutaraldehyde (Sigma G 7526), 6) 0.1M Borate buffer, pH~8-0.1M boric acid/0.025M Borax, 7) 0.1M HCl, 8) 70% Ethanol, and 9) DMF.

A membrane is prepared according to the following procedure: 1) Clean membrane for 15 min using a plasma cleaner; keep membrane taped flat onto a glass slide; maintain contact with glass over the entire membrane during plasma cleaning. 2) Mix EDC, Sulfo-NHS, and MES buffer in the following ratios as shown in Table 2:

TABLE 2

| EDC, Sulfo-NHS, and MES buffer ratios | | | | |
|---|---|---|---|---|
| Downstream [Chitosan] | µL EDC (2) | µL Sulfo-NHS (3) | µL MES (1) | µL DMF (9) |
| 12 mg/mL | 13.5 | 38.4 | 323 | 125 |

3) Incubate 500 µL of mix from step 2 per full membrane (125 µL per quarter membrane or half patterned membrane) 15 min at room temperature. Rinse in water and dry membranes. 4) Mix the Glutaraldehyde and 5 mM MES in the following ratios as shown in Table 3:

TABLE 3

| Glutaraldehyde and MES Ratios | | |
|---|---|---|
| Downstream [Chitosan] | µL GA (5) | µL 5 mM MES (1, dilute 1:10) |
| 12 mg/mL | 8.4 | 992 |

5) Dissolve chitosan in the above mixture and sonicate for 2 min. Apply to the membrane, and squeeze excess solution between two glass slides. 6) Place membranes in an excess (~3 mL) of borate buffer (6) for 33 min. 7) Rinse membranes in Milli-Q® water and incubate in 0.1M HCl for 2 min while sonicating. 8) Rinse membranes three times in running Milli-Q® water, blot dry. Rinse once in 70% ethanol, dry at room temperature.

Example 14—Multivolume Capture and Amplification Results

Multivolume capture and amplification. Capture mix containing HCV RNA was flowed through capture membranes described in Example 12, followed twice by 100 µL MES buffer, then once with 20 µL water. Then, 2 µL of RT-LAMP mix was added to each membrane. They were placed in an Eco well plate and incubated for 70 min at 63° C. inside the Eco real time instrument, and reactions monitored. The first column of Table 4 shows the number of positive reactions out of the total number of reactions, and the second column of Table 4 shows the time it took for the reaction to reach a threshold value. Capture mix 1 comprises approximately 1 ng cRNA and 100 copies HCV RNA per 200 µL in 10 mM MES; Capture mix 2 comprises approximately 1 ng cRNA and 5 copies HCV RNA per 10 µL in 10 mM MES. Experimental details are described in Example 9.

TABLE 4

| Multivolume capture and amplification | | |
|---|---|---|
|  | Positive wells/ total wells | time to positive |
| 0 copies flowed through (neg control) | 0/1 | N/A |
| 10 µL flowed through (5 copies total) with capture mix 1 | 2/4 | 18.2 |
| 200 µL flowed through (100 copies total) with capture mix 2 | 4/4 | 19.5 |
| Membrane with positive LAMP mix | 1/1 | 15.0 |
| Positive LAMP mix | 2/2 | 13.9 |
| Negative LAMP mix | 0/3 | N/A |

Example 15—Multi-Concentration Capture and Amplification Results

Capture mix was flowed through capture membranes described in Example 12, followed by 100 µL MES buffer (twice), then 20 µL water. Then, 2 µL of RT-LAMP mix was added to each membrane. They were placed in an Eco well plate and incubated for 70 min at 63° C. inside the Eco real time instrument, and reactions were monitored. The first column of Table 5 shows the number of positive reactions out of the total number of reactions, and the second column of Table 5 shows the time it took for the reaction to reach a threshold value. Capture mix 1 comprises approximately 5 ng cRNA and 0 copies HCV RNA per 50 µL in 10 mM MES; capture mix 2 comprises approximately 5 ng cRNA and 5 copies HCV RNA per 50 µL in 10 mM MES; capture mix 3 comprises approximately 5 ng cRNA and 50 copies HCV RNA per 50 µL in 10 mM MES; capture mix 4 comprises approximately 5 ng cRNA and 100 copies HCV RNA per 50 µL in 10 mM MES. Experimental details are described in Example 10.

TABLE 5

| Multi-concentration capture and amplification | | |
|---|---|---|
|  | Positive wells/ total wells | time to positive |
| 0 copies flowed through with capture mix 1 | 0/1 | N/A |
| 50 µL flowed through (5 copies total) with capture mix 2 | 2/3 | 19.9 |
| 50 µL flowed through (50 copies total) with capture mix 3 | 3/3 | 20.9 |
| 50 µL flowed through (100 copies total) with capture mix 4 | 1/1 | 21.9 |
| Positive LAMP mix | 2/2 | 22.7 |
| Negative LAMP mix | 0/3 | N/A |

Example 16—Plasma Lysis Results

Row 1 of Table 6 shows results from testing the Loprodyne membranes for amplification only (as opposed to amplification and capture). After wicking through 20 μL NF water, 1 μL of RT-LAMP mix with 10 copies of HCV RNA was wicked into the membrane. Membranes were then incubated for 70 min at 63° C. Incubation happened either in the PDMS gasket system described for FIG. 12 or in an Eco real-time machine well plate. Row 2 of Table 6 shows results from testing the Loprodyne membranes for capture and amplification. Capture mix (10c HCV RNA and 1 ng carrier RNA per 100 μL 10 mM MES buffer) was flowed through the membranes, followed by 100 μL 10 mM MES, and then 20 μL NF water. 1 μL RT-LAMP mix was added to each membrane and they were incubated for 70 min at 63° C. Incubation happened either in the PDMS gasket system described for FIG. 12 or in an Eco real-time machine well plate. Row 3 of Table 6 shows results from testing the Loprodyne membranes to see if exposure to 50 μL of plasma affects amplification. Plasma was lysed as explained in Example 11 before the membranes were exposed to it. After exposure to plasma, 50 μL of 10 mM MES was wicked through the membrane twice, then 10 μL of NF water was wicked through the membrane. 1 μL RT-LAMP mix was added to the membranes and they were then incubated for 70 min at 63° C.

TABLE 6

Plasma Lysis

| Experiment | Positive wells/total wells |
| --- | --- |
| Membrane, 10c HCV RNA added | 24/29 |
| Membrane, 10c HCV RNA/100 μL buffer captured | 20/25 |
| Membrane, Exposed to plasma, 10c HCV RNA added | 5/6 |

Example 17—DNA Capture and Amplification in Large Volume (5 mL) Results

Capture mix containing lambda-phage DNA was flowed through 3.2 mm diameter capture membranes described in Example 12, followed twice by 100 μL MES buffer. Then, 5 μL of PCR mix was added to each membrane. The membranes with PCR mix were placed in an Eco well plate inside the Eco real time instrument and thermal cycled as follows: 1 cycle of 3 min at 98° C., followed by 41 cycles of 20 sec at 95° C./20 sec at 62° C./15 sec at 72° C. The capture mix consisted of 5 mL of 10 mM MES buffer containing 5 copies of lambda-phage DNA and 100 ng carrier DNA; after flowing through the membrane, the DNA was captured and amplified with 5 μL PCR mix. After thermal cycling, correct lambda-phage product was verified with a gel. One membrane received this treatment and was positive for lambda-phage product. One negative control was performed identically as described, except the 5 copies of DNA were omitted and no lambda-phage product was formed.

Example 18—DNA Capture and Amplification in Large Volume (5 mL) Results

Capture mix containing HCV RNA was flowed through 3.2 mm diameter capture membranes described in Example 12, followed twice by 100 μL MES buffer. Then, 5 μL of RT-PCR mix was added to each membrane. They were placed in an Eco well plate inside the Eco real time instrument and thermal cycled as follows: 1 cycle of 15 min at 50° C., 1 cycle of 3 min at 98° C., then 45 cycles of 20 sec at 95° C./20 sec at 62° C./15 sec at 72° C. The capture mix consisted of 5 mL of 10 mM MES buffer containing 3 copies of HCV RNA and 100 ng carrier RNA; after flowing through the membrane, the RNA was amplified with 5 μL RT-PCR mix. After thermal cycling, correct HCV product was verified with a gel. Two membranes received this treatment and both were positive for HCV product. Two negative controls were performed identically as described except the 3 copies were omitted and both showed no HCV product formed.

Example 19—DNA Capture and Amplification in Lysed Plasma Results

Lysed plasma containing lambda-phage DNA was flowed through 3.2 mm diameter capture membranes described in Example 12, followed three times by 100 μL MES buffer. Then, 5 μL of PCR mix was added to each membrane. They were placed in an Eco well plate inside the Eco real time instrument and thermal cycled as follows: 1 cycle of 3 min at 98° C., then 40 cycles of 20 sec at 95° C./20 sec at 62° C./15 sec at 72° C. Plasma was lysed as follows: 1 mL of "modified Zymo buffer" is made by adding 5 μL 2-mercaptoethanol to 955 μL Zymo buffer; 100 μL of "acidification buffer" is made by adding 15.4 μL 1M sodium acetate to 84.6 μL acetic acid; then, 300 μL modified Zymo buffer and 10 μL acidification buffer are added for every 100 μL of plasma. The lysed plasma which was flowed through the membrane consisted of 100 μL George King pooled plasma, 300 μL modified Zymo buffer, 10 μL acidification buffer, and 5 copies lambda-phage DNA; after flowing through the membrane, the DNA was amplified with 5 μL PCR mix. Correct lambda-phage product was verified with a gel. Two membranes received this treatment; one was positive for lambda-phage product and one was negative. One negative control was performed identically as described, except the 5 copies of DNA were omitted and no lambda-phage product was formed.

Example 20—DNA Capture and Amplification in Lysed Plasma Results

Capture mix containing lambda-phage DNA was flowed through capture membranes described in Example 12, followed twice by 100 μL MES buffer. Then, 5 μL of PCR mix was added to each membrane. They were placed in an Eco well plate inside the Eco real time instrument and thermal cycled as follows: 1 cycle of 3 min at 98° C., then 40 cycles of 20 sec at 95° C./20 sec at 62° C./15 sec at 72° C. Correct lambda-phage product was verified with a gel. The multi-volume experiment was set up as follows: zero copies of DNA and 100 ng carrier DNA in 1 mL 10 mM MES buffer was flowed through one membrane and no lambda-phage product was formed. 2 copies of DNA with 20 ng carrier DNA in 200 μL 10 mM MES buffer was flowed through two membranes; the gel showed one membrane positive for lambda-phage product and the other membrane exhibited a faint band. 5 copies of DNA with 50 ng carrier DNA in 500 μL 10 mM MES buffer was flowed through one membrane; it was positive for lambda-phage product. 20 copies of DNA with 200 ng carrier DNA in 2 mL 10 mM MES buffer was flowed through two membranes; both were positive for lambda-phage product.

Example 21—Multivolume Capture and Amplification Results

Figure 16:
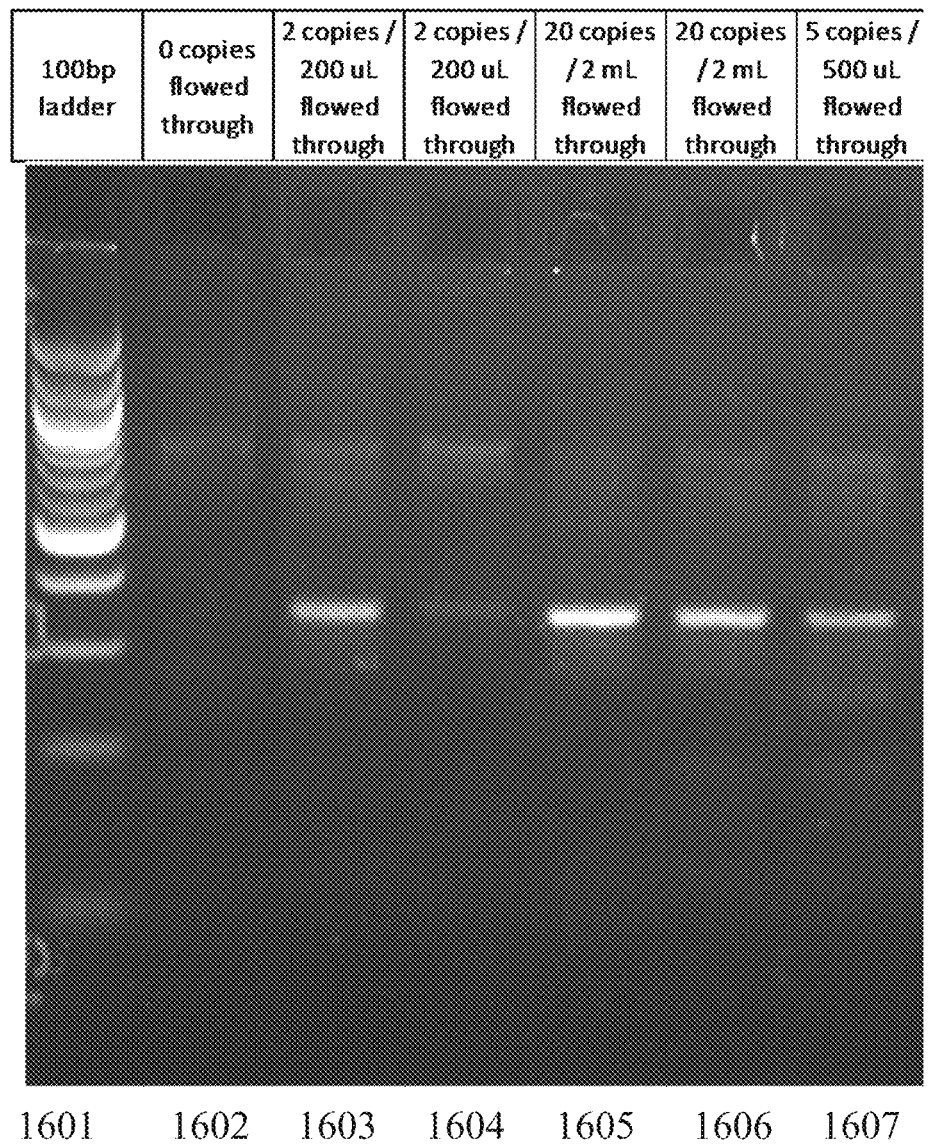
FIG. 16 shows exemplary results from using chitosan-coated membranes to capture and amplify DNA from different volumes.

Capture mix containing lambda-phage DNA was flowed through capture membranes described in Example 12, followed twice by 100 µL MES buffer. Then, 5 µL of PCR mix was added to each membrane. They were placed in an Eco well plate inside the Eco real time instrument and thermal cycled as follows: 1 cycle of 3 min at 98° C., then 40 cycles of 20 sec at 95° C., 20 sec at 62° C., 15 sec at 72° C. Correct lambda-phage product was verified with a gel. The multivolume experiment was set up as follows: 0 copies of DNA and 100 ng carrier DNA in 1 mL 10 mM MES buffer was flowed through one membrane and no lambda-phage product was formed. 2 copies of DNA with 20 ng carrier DNA in 200 µL 10 mM MES buffer was flowed through two membranes; the gel showed one membrane positive for lambda-phage product and the other membrane exhibited a faint band. 5 copies of DNA with 50 ng carrier DNA in 500 µL 10 mM MES buffer was flowed through one membrane; it was positive for lambda-phage product. 20 copies of DNA with 200 ng carrier DNA in 2 mL 10 mM MES buffer was flowed through two membranes; both were positive for lambda-phage product. Example results are shown in FIG. 16 for 0 copies flowed through 1602; 2 copies in 200 µL flowed through 1603, 1604; 20 copies in 2 mL flowed through 1604, 1605; and 5 copies in 500 µL flowed through 1607; with a 100 bp ladder 1601.

Example 22—Depletion Immunoassay on Packed Bead Column with Analyte Access

Figure 41:
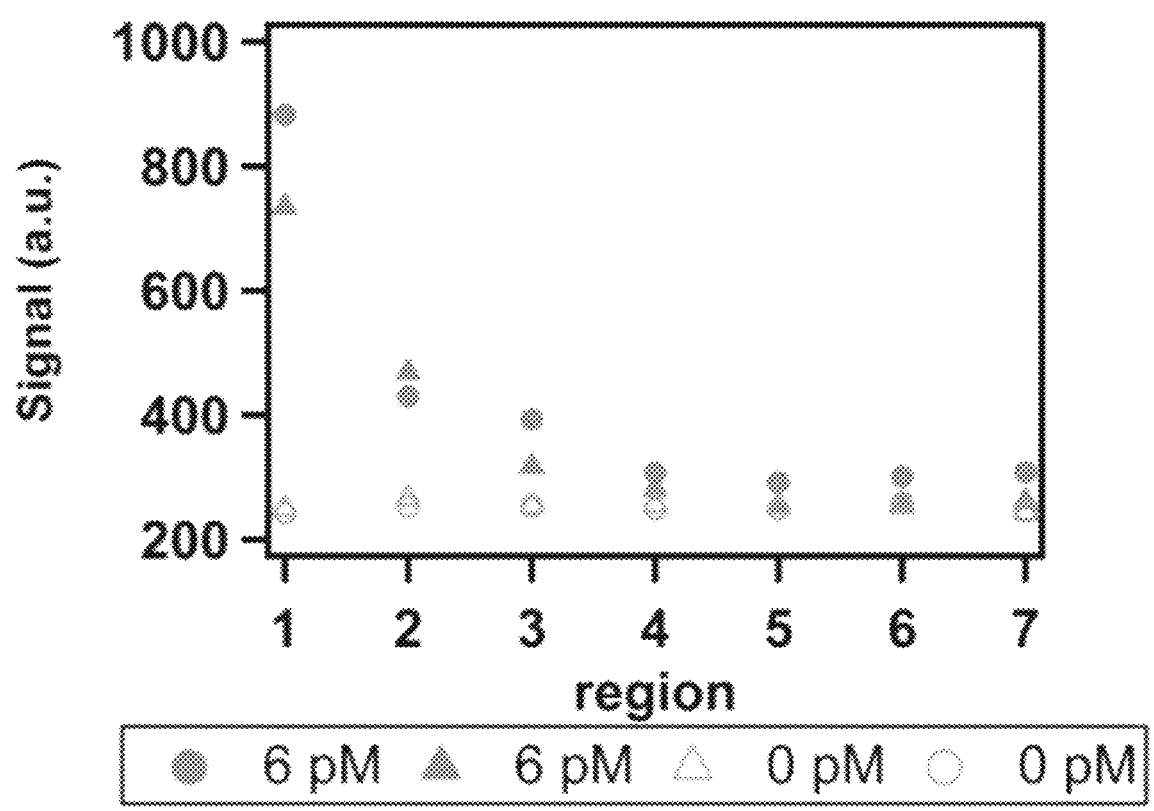
FIG. 41 shows exemplary experimental results of depletion curves from a depletion assay conducted with access structures.

A microfluidic SlipChip device was prepared for a depletion immunoassay using a packed bead column. Glass channels (300 µm wide and 100 µm deep) and 10 vertical glass slots (400 µm long, 1000 µm wide and 100 µm deep spaced at 600 µm) were etched into glass slides using hydrofluoric acid. The dam structure was etched to 5 µm in depth to block the beads. All surfaces were rendered hydrophobic using (Tridecafluoro-1,1,2,2,-tetrahydrooctyl) Trichlorosilane except the dam structure. The surface of the dam structure was unmodified and remained hydrophilic to facilitate the flow of aqueous solution through the column. Glass slides were assembled and aligned under FC40 oil (i.e. Fluorinert™ FC-40). GFAP (Glial fibrillary acidic protein) capture antibody was coated onto 7.4-µm carboxyl-polyethyleneglycol-coated magnetic beads, the beads were loaded into the device, and sample was injected to prime the sample channel (FIG. 39A, FIG. 39A). The top glass plate was slipped to connect the sample channel to the bead column. Sample solution was pushed through the column using a syringe pump (FIG. 39B). The column was slipped to align with vertical glass slots and the beads were spread out to the slots using a magnet (FIG. 39C). The slots were connected, and beads were washed and then labeled with primary (0.5 µg/ml, 30 min) and horseradish peroxidase-conjugated secondary detection antibodies (0.15 µg/ml, 30 min) (FIG. 39D). Following incubation with labeling reagent, fluorescent substrate solution containing 10 µM Amplex UltraRed was loaded into the wells and the glass plates were immediately slipped to achieve well isolation, compartmentalizing the vertical slots for readout (FIG. 39E, FIG. 40B, FIG. 40C). Imaging was conducted with a standard fluorescent microscope, and experimental results of depletion curves were generated (FIG. 41).

Example 23—Fabrication of Device with Bead in Well Digital Units

Sodalime and borofloat glass plates coated with Cr and photoresist (Telic Company, Valencia, Calif.) were used as a substrate for the device. Standard photolithographic methods were used to transfer the designed pattern, including the microwells and channels, onto the glass plates. The photomask was designed using AutoCAD and then printed on a transparent film (CAD/Art Services, Bandon, Oreg.) or a Cr mask (Photo sciences, Torrance, Calif.) (FIG. 26). A PDMS/glass adapter was used to connect the tubing to the device.

To fabricate the channels in the top plate of the device, a wet-etching method with hydrofluoric acid was used. The back and side of the plate were taped to protect the bare glass from HF etching. Then the glass plates were immersed in HF etching solution at 40° C. with continuous shaking. Photoresist/Chrome served as the etching mask. All channels were etched to a depth of 50 µm. Typical etching rate under these conditions was 1.3 µm/min. After etching, plates were rinsed thoroughly with water to remove residual HF and blown dry with nitrogen. Remaining photoresist and the chromium layer were removed by acetone and chrome etchant. Through holes were drilled at both ends of the channels and then the plate was thoroughly cleaned with piranha solution. Finally, the plate was air plasma treated for 100 seconds and subjected to gas-phase silanization using trichlorosilane (Tridecafluoro-1,1,2,2-tetrahydrooctyl; Gelest Inc., Morrisville, Pa.). The vacuum in a glass desiccator was pumped down to 0.4 Torr at room temperature to facilitate the vaporization of fluorosilane, and then the chamber was closed for 1 hour. Next, the plate was baked at 95° C. overnight and rinsed by FC3283 to remove unbound silane. The plate was further baked for at least 30 minutes to complete the fluorosilanization procedure.

To fabricate micro-wells in the bottom half of the device for single bead confinement, borofloat glass plates and a fluorine-based dry etching method with C4F8-based plasma were used. After the photolithography, the photoresist was removed from the glass plate using acetone. The remaining Cr layer served as the dry etching mask. The glass plate was mounted on a 6-inch carrier wafer using thermogrease (Fomblin) and subjected to C4F8-based plasma etching (Plasmalab 100, Oxford Instruments) under the following conditions: chamber pressure 10 milliTorr, $C_4F_8$ flow rate 40 standard cubic centimeters per minute (sccm), ICP power 3000 watts. Typical etching rate under these conditions was 0.2-0.3 µm/min. To improve etching uniformity across the plate, a two-step etching protocol was adopted. At the end of the first half of the etching step, the plate was removed from the chamber and subjected to a sonication-assisted wash to remove non-volatile residuals, such as sodium fluoride. Then the plate was rinsed by isopropanol and blown dry using nitrogen. The second half the etching step was performed with the plate rotated 180° C. to increase etching uniformity.

Fluorine-based dry-etching was used to create microwells in a glass substrate for single bead confinement, with a design such as that shown in FIG. 26A. To achieve uniform single bead loading per microwell for downstream digital readout and data interpretation using Poisson statistics, the anisotropic etching process was precisely controlled to yield microwells with nearly vertical side walls. The dimensions of the etched microwells were approximately 3 µm in diameter and 3 µm in depth; just enough to accommodate a single 2.7 µm microparticle (see FIG. 27A-B). Over-etched microwells will trap more than one microparticle (see FIG.

27C-D) and thus should be avoided. The microwell surface was functionalized with PEG-silane to render it hydrophilic, to ensure successful particle loading. The surface outside of the microwells was functionalized with fluorinated silane to render it fluorophilic as is commonly employed in SlipChip designs (see, for example, Weishan Liu, Delai Chen, Wenbin Du, Kevin P. Nichols, and Rustem F. Ismagilov, "SlipChip for Immunoassays in Nanoliter Volumes," Analytical Chemistry 2010 82:3276-3282; Wenbin Du, Liang Li, Kevin P. Nichols, and Rustem F. Ismagilov, "SlipChip," Lab Chip 2009 9: 2286-2292). This combination of hydrophilic and fluorophilic surface chemistry allows the microwells to be easily compartmentalized for downstream digital readout by simply flowing fluorocarbon oils over the microwells.

Figure 22B:
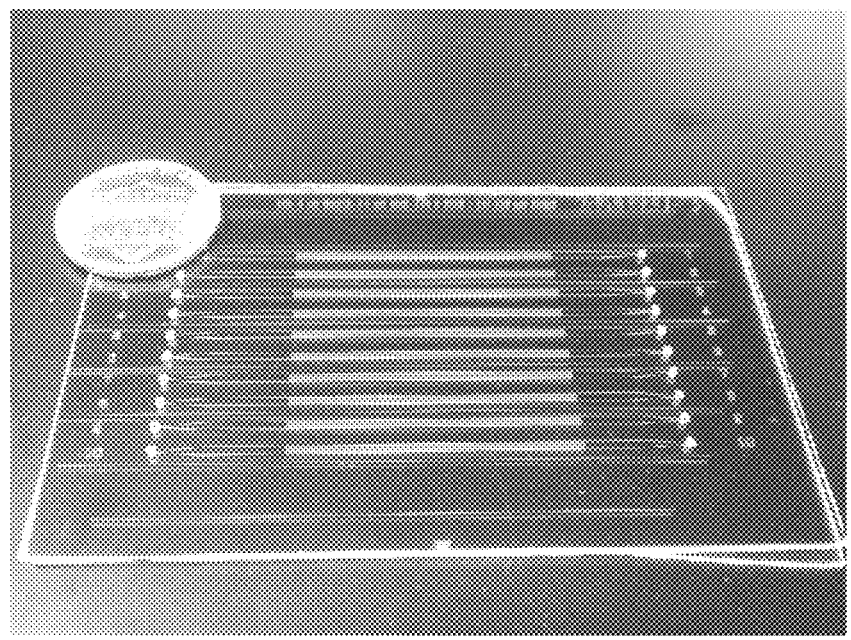
FIG. 22B shows an exemplary microfluidic device comprising channels with digital units.
Figure 22C:
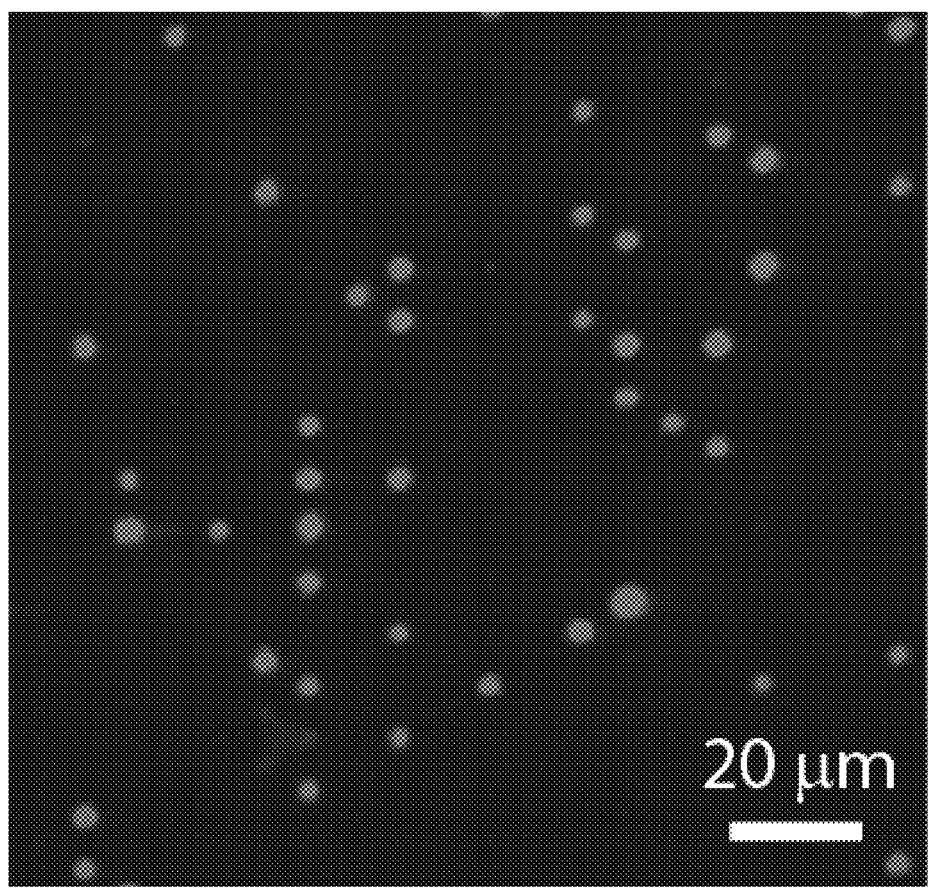
FIG. 22C shows exemplary positive signal being generated from digital units.
Figure 23:
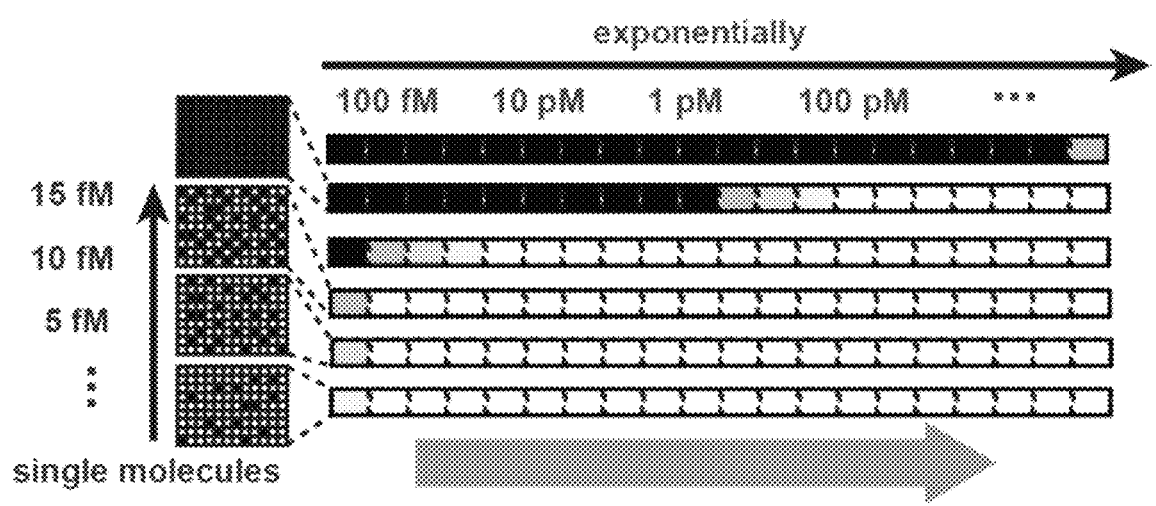
FIG. 23 shows an exemplary design of a depletion assay using digital units and capture regions to measure the concentration of analyte in a sample.
Figure 24:
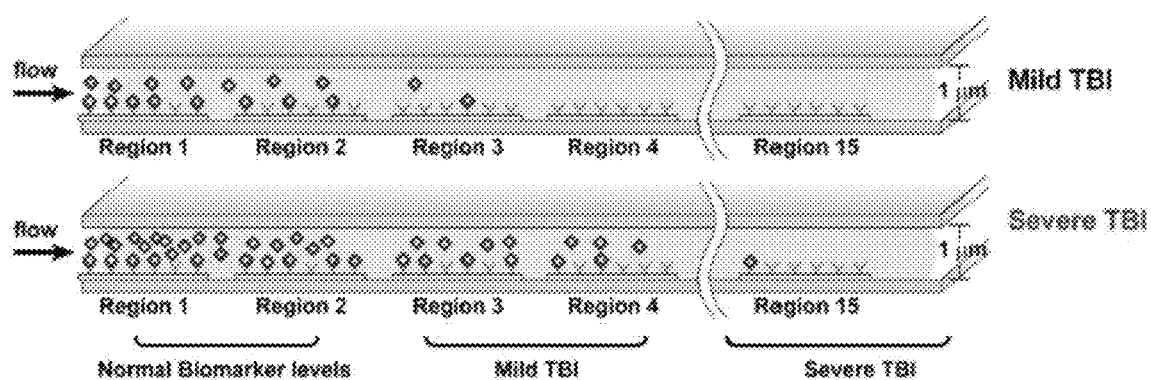
FIG. 24 shows an exemplary design of a depletion assay using digital units and capture regions to measure the concentration of analyte (e.g., biomarker for traumatic brain injury) in a sample.
Figure 25:
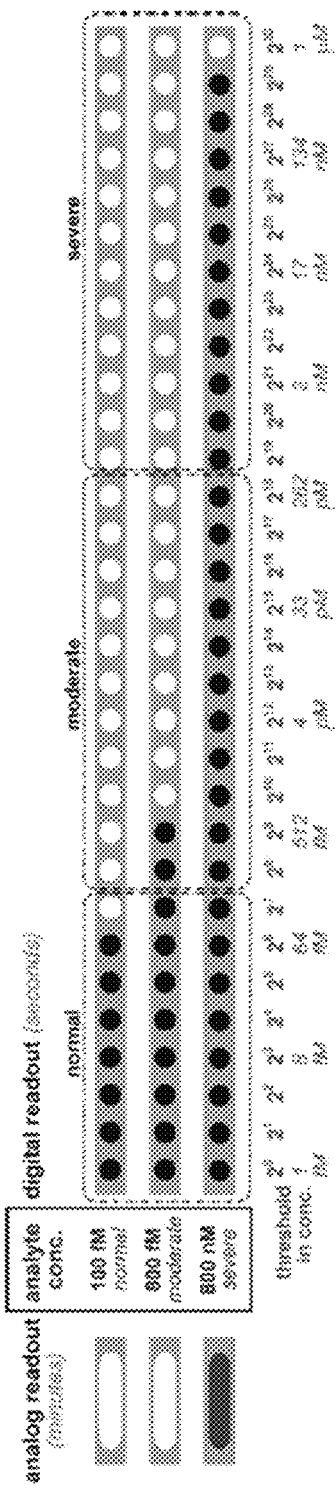
FIG. 25 shows an exemplary design of a depletion assay using digital units and capture regions to measure the concentration of analyte in a sample.

Next, a bead loading protocol is used to achieve uniform and high singlet bead loading across the chip with an area of ~3 cm×3 cm (FIG. 22B). Here, simple slipping motion on SlipChip devices was used to enhance bead loading. Magnetic microparticles were injected into the channel and then pulled to the side wall using a magnet. Then, the top plate was slipped to physically scrape the microparticles against the magnetic force to load the microwells. Both the concentration of the microparticles and the number of slipping motions would influence the bead loading efficiency. A loading efficiency approaching unity can be achieved when both factors are maximized.

Example 24—Digital Depletion Assay with Streptavidin and Biotin

A device with streptavidin-coated beads in wells as digital units was fabricated as described in Example 23. A 3 µL sample of analyte, in this case biotin-modified beta-galactosidase, was loaded into the device and incubated for 1 hour. The PEG surface in the microwells can suppress non-specific binding. Fluoro-surfactant was incorporated into the FC40 oil to suppress non-specific adsorption of proteins on multiphase interfaces. All protein solutions were prepared in commercial blocking buffers to minimize protein loss. Next, a solution of fluorogenic substrate resorufin β-D-galactopyranoside (RGP) was injected into the channel, immediately followed by a flow of FC40 to compartmentalize the beads in the microwells. Fluorescence images were acquired in TexasRed and GFP channels on an inverted microscope equipped with a 0.63× camera adapter and a digital CCD camera using the autofocus function. Positive bead count and total bead count were analyzed based on threshold fluorescence intensity and morphological criteria. The image acquisition, processing and analysis were all performed using metamorph. FIG. 34E shows a log-log plot of the fraction of beads that contained at least one enzyme (positive fraction of beads) as a function of enzyme concentration in this stationary assay. As the positive fraction of beads increases, the Poisson distribution deviates from linearity, leading to a greater imprecision of concentration determination (see, for example, David M. Rissin, David R. Fournier, Tomasz Piech, Cheuk W. Kan, Todd G. Campbell, Linan Song, Lei Chang, Andrew J. Rivnak, Purvish P. Patel, Gail K. Provuncher, Evan P. Ferrell, Stuart C. Howes, Brian A. Pink, Kaitlin A. Minnehan, David H. Wilson, David C. Duffy Simultaneous Detection of Single Molecules and Singulated Ensembles of Molecules Enables Immunoassays with Broad Dynamic Range Anal Chem. 2011. 83(6): 2279-2285.). In some cases, digital measurements with a positive fraction below 0.8 are preferred. The limit of detection was determined by extrapolating the concentration from the signal equal to background signal+3 standard deviations of the background signal. The calculated dynamic range in this stationary assay ranged from 0.02 femtomolar (fM) to 0.5 picomolar (pM), demonstrating a response of ~20,000 fold, with a sensitivity of ~30 molecules in 3 microliter (µL).

Example 25—Digital Depletion Assay with Streptavidin and Biotin

A device with streptavidin-coated beads in wells as digital units was fabricated as described in Example 23. 3 µL of an enzyme solution was flown over the beads through the channel at a velocity of 17 µm/s for 1 hour, and the capture molecules were detected. Fluorescence images were acquired in TexasRed and GFP channels on an inverted microscope equipped with a 0.63× camera adapter and a digital CCD camera using the autofocus function. Positive bead count and total bead count were analyzed based on threshold fluorescence intensity and morphological criteria. The image acquisition, processing and analysis were all performed using metamorph. FIG. 34A shows a plot of the positive fractions of beads as a function of capture regions; in this plot, each curve represents one enzyme concentration. Enzyme molecules concentrate at the beginning of the capture regions. As enzyme concentrations increase, more molecules are captured in the farther-away, high-order regions. To relate the positive fractions of beads to the concentration of enzymes at a range of low concentrations, enzyme concentration is plotted against the positive fraction of beads at the first capture region, where the positive fraction is the highest in all capture regions (FIG. 34B). The calculated dynamic range in this plot ranged from 9 aM to 20 fM. To quantify the concentration of enzymes at a range of high concentrations, the enzyme concentration was plotted against the number of capture regions that can deplete the sample to generate a positive fraction lower than 0.8, which is the preferred upper limit of digital readout in some embodiments (FIG. 34C). This extends the dynamic range up to beyond 0.3 nanomolar (nM). The range of mediate concentrations can be quantified by plotting enzyme concentration against the number of capture regions that can deplete the sample to generate a lower positive fraction, such as 0.07 in FIG. 34D. The combined dynamic range demonstrates a response of ~40,000,000 fold, an improvement of more than three orders of magnitude compared to the stationary assay, while maintaining a sensitivity of ~20 molecules in total.

Example 26—Digital Depletion ELISA with TNF-Alpha (TNF-α)

Figure 28A:
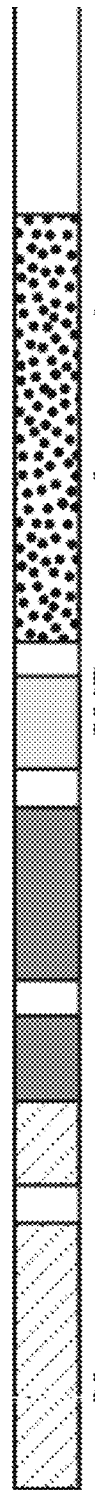
FIG. 28A shows an exemplary schematic of a sequence of solutions used to conduct an assay.
Figure 28B:
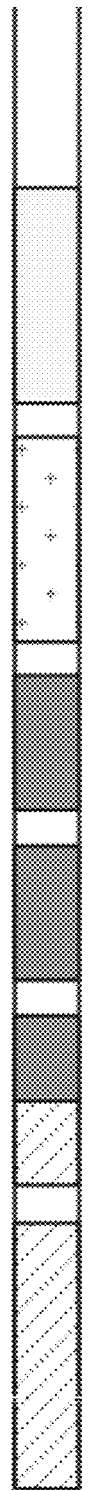
FIG. 28B shows an exemplary schematic of a sequence of solutions used to conduct an assay.
Figure 28C:
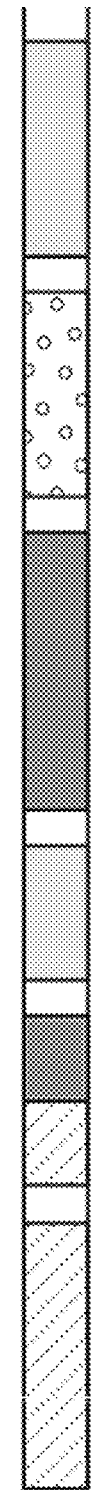
FIG. 28C shows an exemplary schematic of a sequence of solutions used to conduct an assay.

A device with beads in wells as digital units was fabricated as described in Example 23. Assay reagents including sample solution, detection antibody solution, labeling solution of enzyme, washing buffer and FC40 were loaded into Teflon tubing with air spacers and then infused into the channels using a syringe pump at a controlled flow rate (FIG. 28). As a dozen of air-aqueous, air-oil and aqueous-oil interfaces migrate through the microparticle-loaded regions, the device was kept on a magnet throughout the assay to minimize microparticle loss. Typically, 10-20% of microparticle loss was observed. Because the digital readout is inherently ratiometric, this loss is not detrimental to the assay performance. Fluorescence images were acquired in TexasRed and GFP channels on an inverted microscope equipped with a 0.63× camera adapter and a digital CCD camera using the autofocus function. Positive bead count and total bead count were analyzed based on threshold fluorescence intensity and morphological criteria. The image acquisition, processing and analysis were all performed using metamorph.

FIG. 35 shows experimental curves obtained from a model protein system, human TNF-α. The calibrator molecules were spiked to 25% bovine serum solution. TNF-alpha molecules concentrate at the beginning section of the sensing regions. As sample concentrations increase, more TNF-alpha molecules migrate further to the high-order regions. To read out the captured TNF-alpha molecules, they were labeled with an enzyme tag by sequentially incubating with biotinylated detection antibody and streptavidin-galactosidase. The overall labeling efficiency can determine the sensitivity and the dynamic range of the digital depletion ELISA. While the labeling efficiency can be experimentally tuned from 0.4% to 23.8% by adjusting labeling conditions (FIG. 32), a medium labeling efficiency 3.6% was used to work with a manageable background at 6%. Poisson statistics predicts the theoretical limit is 1.7 femtomolar (fM) if statistical counting error dominates the system error. Experimentally, a sensitivity of ~6 fM was obtained. The observed loss in sensitivity can be caused by experimental errors such as incomplete washing and imperfect oil sealing. The experimentally demonstrated dynamic range is approximately 5.5 logs from 6 fM to 2 nM based on a 3 mm long sensing region. The high sensitivity allows the endogenous concentration of TNF-α in human serum samples to be determined (FIG. 35B). The estimated concentration is 0.031±0.001 pM in 25% serum samples, which translates to 0.125±0.004 pM in 100% serum sample. This value is consistent with the ones determined previously using digital ELISA and other single-molecule approaches. The concentration of TNF-alpha in the bloodstream can go as high as double digital picomolar (pM) range in certain medical conditions, which is well within the measurable dynamic range reported herein.

Example 27—Folded Membrane Flow-Through Depletion Assay

A membrane, comprising hydrogel-filled pores as digital units, is folded into a series of capture regions, as shown in FIG. 17. A sample comprising analytes is flowed through the membrane at flow rates from about 0.01 µL/min to about 100 µL/min. Analytes bind to digital units in the membrane, with more analyte binding to digital units in upstream capture regions than to those in downstream capture regions. The membrane is unfolded, signal is generated from digital units and imaged, and the number of positive digital units in each capture region is measured to produce a depletion curve. The number of analytes in the sample is determined from the depletion curve and the profile of positive capture regions.

Example 28—Membrane Flow-Through Depletion Assay

A flat membrane, comprising hydrogel-filled pores as digital units, placed inside a channel structure, as shown in FIG. 18. The channel structure divides the membrane into capture regions, and allows sample to be flowed sequentially through the capture regions. A sample comprising analytes is flowed through the membrane at flow rates from about 0.01 µL/min to about 100 µL/min. Analytes bind to digital units in the membrane, with more analyte binding to digital units in upstream capture regions than to those in downstream capture regions. Signal is generated from digital units and imaged, and the number of positive digital units in each capture region is measured to produce a depletion curve. The number of analytes in the sample is determined from the depletion curve and the profile of positive capture regions.

Example 29—Capture Efficiency as a Function of Flow Rate

A PEG hydrogel was polymerized into a Whatman Nucleopore track-etched hydrophilic polycarbonate membrane with pore radius of approximately 10 microns and thickness of 10 microns. The PEG hydrogel pre-polymer solution contained the following reagents: 13.3 µM acrylated Anti-TNF-alpha mouse antibody, 20% v/v Diacryl-PEG 700 MW, 40% v/v of a solution of 30% wt/v 3550 molecular weight PEG porogen, 5% v/v 2-hydroxy2-methylpropiophenone, and 35% v/v 3×Tris EDTA. Gel was polymerized from a height of 20 mm for 0.4 seconds, using a Lesco Super Spot Max UV lamp with output of 10.8 W/cm$^2$ at the tip of the fiber optic. Following polymerization, the membranes with immobilized gel were soaked in Phosphate Buffered Saline with Tween® 20 (PBST) for at least ten minutes to remove porogen before performing the assay. An example can be seen in FIG. 20.

Figure 19:
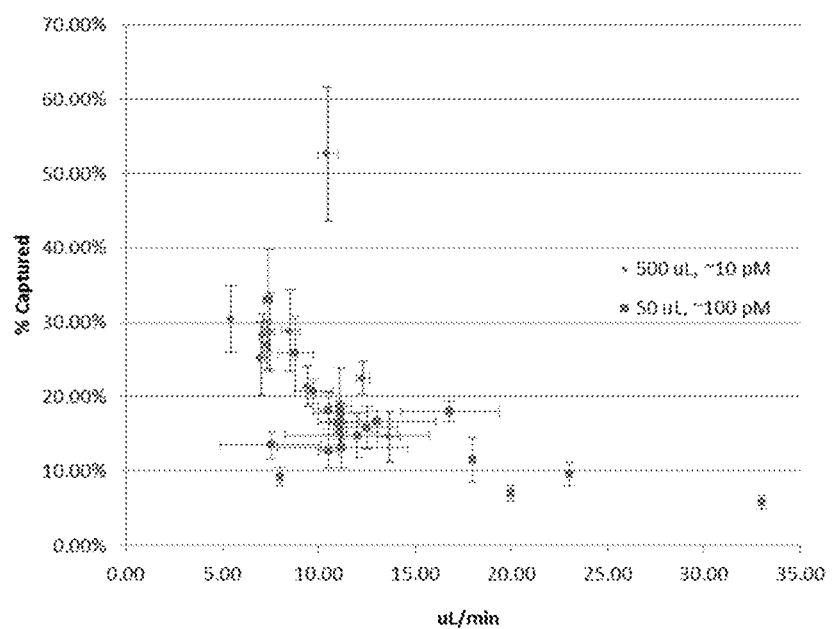
FIG. 19 shows exemplary capture efficiencies versus flow rate for digital units.

In the assay, anti-mouse phycoerythrin conjugated antibody was flowed through the membrane with gel at varied concentrations and volumes, using a fixed pressure drop of 0.1 atmosphere. Flow rate was measured by quantifying the volume of effluent every minute. The amount of anti-species antibody captured in the gel was quantified by fluorescence microscopy against a solution of known concentration in a microchannel. The remaining, unbound antibody in the effluent was quantified using the fluorescence mode of a plate reader against a standard curve. Capture efficiencies versus flow rate are shown in FIG. 19 for two samples, 500 µL of approximately 10 pM (circles) and 50 µL of approximately 100 pM (squares).

Example 30—Porogen and Available Antibody Concentration in Membrane-Bound Gels

Figure 21:
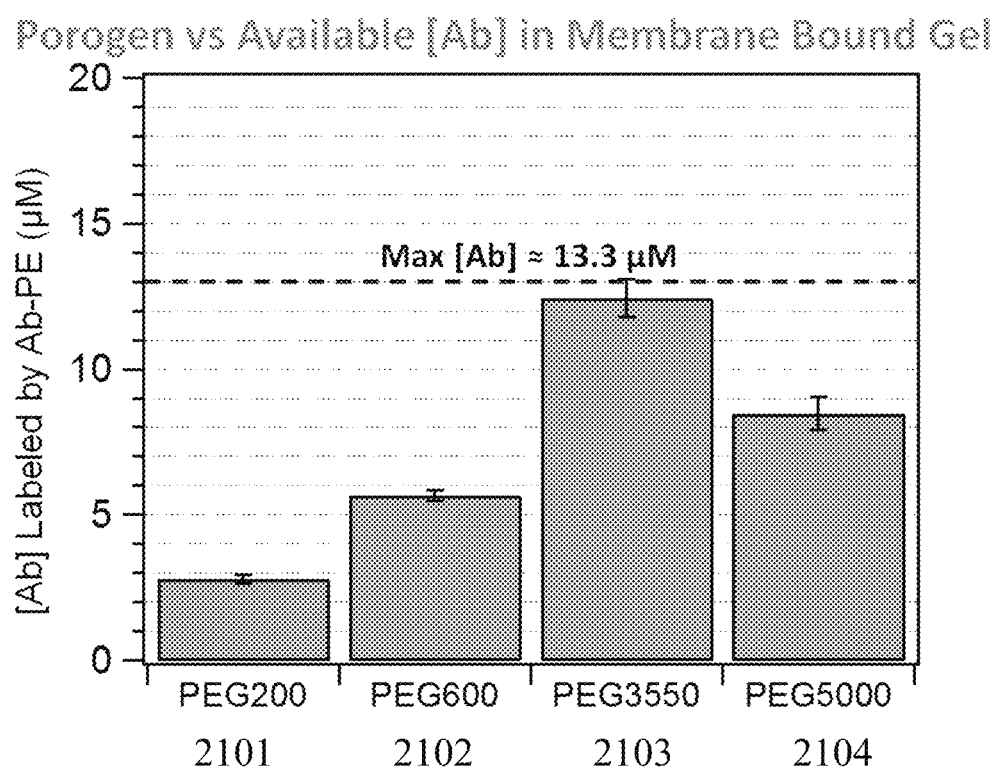
FIG. 21 shows exemplary amounts of available capture agent versus porogen type.

Capture agent is immobilized at high concentrations in hydrogel digital units in a membrane, and labeled by anti-species antibody. Different species of PEG are used as shown in FIG. 21, including PEG200 (2101), PEG600 (2102), PEG3550 (2103), and PEG5000 (2104). The maximum antibody immobilized in this scenario, based on concentration, is 13.3 micromolar and is achieved with PEG3550 porogen. In some cases, capture agent is immobilized from 2 to 14 micromolar, or 1 micromolar to 1 molar, or 1 micromolar to 1 millimolar. In some cases, a hydrogel with capture agent is polymerized. Porogen molecular weight can be varied to increase or decrease the amount of capture agent accessible to analyte and/or detection and/or labeling reagents. In some cases, porogen molecular weight ranges from 200 to 5000 atomic mass units or from 100 to 100000 atomic mass units. In some cases, porogen is removed from the gel. In some cases, porogen is globular, spherical, rod-like, or amorphous in nature. In some cases, porogen is comprised of polymers. In some cases, porogen is a mass of particles within the matrix. In some cases, porogen is an individual particle within the matrix. In some cases, porogen molecules interact with each other.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for analyzing a fluid sample, comprising:
providing a device comprising
a fluid inlet,
a fluid receiving structure,
a fluid path connecting the fluid inlet and the receiving structure,
a plurality of digital units arranged in capture regions located in the fluid path, each digital unit capable of capturing at least one analyte comprising nucleic acid, wherein the capture regions comprises
a first capture region comprising a first digital unit, and
a second capture region opposed to the first capture region, wherein the second capture region comprises a second digital unit, and wherein the first capture region or the second capture region is configured to slip relative to the other;
introducing a fluid sample into the device via the fluid inlet, the fluid sample comprising analytes;
flowing the fluid sample in the fluid path from the fluid inlet to the fluid receiving structure;
depleting analytes from the fluid sample by capturing analytes with the digital units as it flows through the array of capture regions;
slipping the first capture region or the second capture region relative to the other to isolate the first digital unit from the second digital unit;
performing digital amplification of the analytes in the isolated digital units, wherein the digital amplification generates a signal in response to presence of the at least one analyte; and
detecting the presence or absence of a signal generated from each of the digital units to determine the concentration or identity of the analytes in the fluid sample.

2. The method of claim 1, wherein the slipping comprises actuating a portion of the device.

3. The method of claim 1, wherein the determining comprises identifying the number of positive signals or negative signals generated from said digital units isolated from said fluid path.

4. The method of claim 1, wherein said first digital unit generates a positive signal, and wherein said second digital unit does not generate a positive signal, and wherein a relative location of said first and second digital units along said fluid path before isolation is used to determine said concentration.

5. The method of claim 1, wherein the flowing comprises flowing the fluid sample through the digital units.

6. The method of claim 1, wherein the digital amplification comprises polymerase chain reaction (PCR).

7. The method of claim 1, wherein the digital amplification comprises isothermal amplification.

8. The method of claim 3, comprising classifying a digital unit as positive based on presence of detected signal in the digital unit.

9. The method of claim 3, comprising classifying a digital unit as negative based on absence of detected signal in the digital unit.

10. The method of claim 3, comprising generating a background signal in a negative control digital unit.

11. The method of claim 10, comprising classifying a digital unit as positive if the detected signal in the digital unit exceeds the background signal.

12. The method of claim 10, comprising classifying a digital unit as negative if the generated signal in the digital unit does not exceed the background signal.

13. A method for analyzing a sample, comprising:
providing a device comprising
a fluid inlet,
a fluid receiving structure,
a fluid path connecting the fluid inlet and the receiving structure,
a plurality of digital units located in the fluid path, each digital unit capable of capturing at least one analyte comprising nucleic acid, wherein the plurality of digital units comprise, in the direction from the fluid inlet towards the fluid receiving structure,
a first digital unit, and
a second digital unit;
introducing a fluid sample into the device via the fluid inlet, the fluid sample comprising analytes;
flowing a fluid sample in the fluid path from the fluid inlet to the fluid receiving structure;
depleting analytes from the fluid sample by capturing analytes with the digital units as it flows from the fluid inlet to the fluid receiving structure;
isolating the digital units;
performing digital amplification of the analytes in the isolated digital units, wherein the digital amplification generates a signal in response to presence of the at least one analyte; and
detecting the presence or absence of a signal generated from each of the digital units to determine the concentration or identity of the analytes in the fluid sample.

14. The method of claim 13, wherein the isolating comprises actuating a portion of the device.

15. The method of claim 13, wherein the determining comprises generating a profile of each digital unit in the flow path, wherein the profile comprises
a positive or negative classification of the digital unit based on presence or absence detected signal in the digital unit, and
location of the digital unit in the fluid path.

16. The method of claim 13, wherein the determining comprises counting a number of the digital units along the fluid path up to a location in the fluid path where one or more of the digital units exhibit an absence of the signal.

17. The method of claim 13, wherein the flowing comprises flowing the fluid sample through the digital units.

18. The method of claim 13, wherein the digital amplification comprises polymerase chain reaction (PCR).

19. The method of claim 13, wherein the digital amplification comprises isothermal amplification.

20. The method of claim 15, comprising classifying a digital unit as positive based on presence of detected signal in the digital unit.

21. The method of claim 15, comprising classifying a digital unit as negative based on absence of detected signal in the digital unit.

22. The method of claim 13, wherein a total number of binding sites contained within the fluid path, the binding sites capable of binding the at least one analyte, exceeds a total number of analytes in the fluid sample.

23. The method of claim 1, wherein a total number of binding sites contained within the fluid path, the binding sites capable of binding the at least one analyte, exceeds a total number of analytes in the fluid sample.

* * * * *